(12) United States Patent
Limnios

(10) Patent No.: US 12,116,594 B2
(45) Date of Patent: Oct. 15, 2024

(54) METHODS FOR DIFFERENTIATING CELLS

(71) Applicant: BOND UNIVERSITY LTD, Gold Coast (AU)

(72) Inventor: Ioannis Jason Limnios, Varsity Lakes (AU)

(73) Assignee: BOND UNIVERSITY LTD, Gold Coast (AU)

( * ) Notice: Subject to any disclaimer, the term of this patent is extended or adjusted under 35 U.S.C. 154(b) by 211 days.

(21) Appl. No.: 17/455,334

(22) Filed: Nov. 17, 2021

(65) Prior Publication Data
US 2022/0177836 A1 Jun. 9, 2022

Related U.S. Application Data

(62) Division of application No. 15/781,330, filed as application No. PCT/AU2016/000390 on Dec. 5, 2016, now abandoned.

(30) Foreign Application Priority Data

Dec. 4, 2015 (AU) ................................. 2015905049

(51) Int. Cl.
  *C12N 5/071* (2010.01)
  *C12N 5/079* (2010.01)

(52) U.S. Cl.
  CPC ........ *C12N 5/0621* (2013.01); *C12N 2500/32* (2013.01); *C12N 2500/98* (2013.01); *C12N 2501/385* (2013.01); *C12N 2501/727* (2013.01); *C12N 2501/998* (2013.01); *C12N 2501/999* (2013.01); *C12N 2506/02* (2013.01); *C12N 2506/45* (2013.01); *C12N 2533/52* (2013.01); *C12N 2533/90* (2013.01)

(58) Field of Classification Search
  CPC .............. C12N 5/0621; C12N 2500/98; C12N 2501/998; C12N 2501/999; C12N 2506/02; C12N 2506/45
  See application file for complete search history.

(56) References Cited

U.S. PATENT DOCUMENTS

| | | |
|---|---|---|
| 2015/0159134 A1 | 6/2015 | Choudhary et al. |
| 2015/0175964 A1 | 6/2015 | Clegg et al. |
| 2016/0243285 A1 | 8/2016 | Zhang et al. |

FOREIGN PATENT DOCUMENTS

| | | | |
|---|---|---|---|
| WO | WO 2015/054526 A2 | * | 4/2015 |
| WO | WO 2015/087231 A1 | | 6/2015 |
| WO | WO 2015/175783 A1 | | 11/2015 |
| WO | WO 2017/044483 | | 3/2017 |

OTHER PUBLICATIONS

International Search Report issued in corresponding International Application No. PCT/AU2016/000390, Mar. 14, 2017, 6 pages.
Leach, L.L., et al., "Canonical/β-Catenin Wnt Pathway Activation Improves Retinal Pigmented Epithelium Derivation From Human Embryonic Stem Cells", Investigative Ophthalmology & visual Science, Feb. 2015, vol. 56, pp. 1002-1013.
Leach, L.L., et al., "Concise review: making stem cells retinal: methods for deriving retinal pigment epithelium and implications for patients with ocular disease", Stem Cells, Mar. 2015, vol. 33, pp. 2363-2373.
Maruotti, J., et al., "Small-molecule-directed, efficient generation of retinal pigment epithelium from human pluripotent stem cells," Proceedings of the National Academy of Sciences of the United States of America, Sep. 2015, vol. 112, pp. 1095-10955.
Osakada, F., et al., "In vitro differentiation of retinal cells from human pluripotent stem cells by small-molecule induction," Journal of Cell Science, 2009, vol. 122, pp. 3169-3179.
Ou, Q., et al., "High-effect induction of human iPS cells into retinal pigment epithelial cells with small molecules", Investigative Ophthalmology & Visual Science, Jun. 2015, vol. 56 (Annual Meeting of the Association-for-Research-in-Vision-and-Ophthalmology (ARVO), Denver, USA, May 2015), Meeting Abstract [BIOSIS Document ID: PREV201600025143].
Supplementary European Search Report issued in connection with corresponding EP Patent Application No. 16869396.8, mailed on Aug. 29, 2019, 14 pages.
Surmacz, B., et al., "Directing differentiation of human embryonic stem cells toward anterior neural ectoderm using small molecules," Stem Cells, 2012, vol. 30, pp. 1875-1884.
Vaajasaari et al., "Toward the Defined and Xeno-Free Differentiation of Functional Human Pluripotent Stem Cell-Derived Retinal Pigment Epithelial Cells," Molecular Vision, 17:558-575, Feb. 22, 2011.
Westenskow, P., et al., "Efficient derivation of retinal pigment epithelium cells from stem cells", JoVE (Journal of Visualized Experiments), Mar. 2015, vol. 97, e52214.

(Continued)

*Primary Examiner* — Shin Lin Chen
(74) *Attorney, Agent, or Firm* — Knobbe Martens Olson & Bear LLP

(57) ABSTRACT

A method for producing eyefield progenitor cells, including: (a) obtaining a starting population comprising human pluripotent stem cells (hPSCs) that are dissociated to essentially single cells; (b) culturing said hPSCs to a contact-inhibited monolayer; (c) contacting said hPSC monolayer in a primary differentiation medium to generate a homogeneous, contact-inhibited monolayer of anterior neuroectodermal cells (ANECs); (d) dissociating said homogeneous ANECs from (c) into essentially single cells; (e) forming dissociated ANECs into size-controlled and homogeneous 3D aggregates (ANEBs), wherein the ANEBs are 3D aggregates of anterior neuroectodermal cells that are distinct from embryoid bodies; and (f) culturing said ANEBs in a primary differentiation medium in suspension to further differentiate them to Eyefield Progenitor Cells (EFPCs).

20 Claims, 31 Drawing Sheets

(56) References Cited

OTHER PUBLICATIONS

Written Opinion of the International Searching Authority issue din corresponding International Application No. PCT/AU2016/000390, Mar. 14, 2017, 9 pages.
Zhou, S., et al., "Differentiation of human embryonic stem cells into cone photoreceptors through simultaneous inhibition of BMP, TGFβ and Wnt signaling," Development, Oct. 2015, vol. 142, pp. 3294-3306.

* cited by examiner

A

B

Mel1　　　　　　　G2　　　　　　　G15

Scale = 50μm

METHODS FOR DIFFERENTIATING CELLS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

This invention relates to methods for generating retinal cells from pluripotent stem cells.

Description of the Related Art

Millions of people suffer from retinal diseases, disorders and conditions around the world that relate to dysfunction, injury, or loss of the retinal pigment epithelium (RPE), the cells of the neural retina (including rod and cone photoreceptors, bipolar cells, amacrine cells, retinal ganglion cells, muller cells and horizontal cells), the bruch's membrane, and/or the choroid. Disease progression often involves the destabilisation of the photoreceptor/RPE/Bruch's membrane/Choroid complex, and the subsequent dysfunction and death of both the RPE and the neural retinal layer. In the case of age-related macular degeneration (AMD), the location of cell death is in the macula, leading to the impairment of central vision. Specific disorders associated with a degeneration or deterioration of the retina itself and of the RPE are AMD, hereditary macular degenerations including Best disease (the early onset form of vitelliform macular dystrophy), subtypes of retinitis pigmentosa (RP), and macular dystrophies such as Stargardt's and Stargardt's-like disease.

There is a need to produce RPE cells (RPECs) from human stem cells that can be used for the treatment of retinal degenerative diseases and injuries. Similarly there is a need in some disease conditions to replace photoreceptors (PhR) which depend on RPECs for their survival and function. A potential treatment for such diseases is the transplantation of RPECs into the retina of those affected with the disease, disorder or condition. It is now known that the addition of healthy transplanted RPE cells in the retina of the subject may delay, halt or reverse degeneration, improve retinal function and prevent blindness that may be caused by the above-mentioned diseases, disorders, or conditions. In cases of AMD, or in cases of photoreceptor specific degeneration, it is likely that the, RPEC, photoreceptor cells, or both, may need to be replaced in order to provide therapeutic benefit.

An important part of the retina, that being the macula, is located centrally in the retina and is responsible for fine visual detail and colour perception, and is crucial for many daily activities such as facial recognition and reading. Within the disease process the macula can be deleteriously affected, such as in retinitis pigmentosa (RP), age-related macular degeneration (AMD) and Best disease. Quite often, the RPE lose their function or even fail when these diseases take hold. This can be devastating since the RPECs support photoreceptor function which is crucial in retinal renewal and vision. The failure can lead to distorted vision, and ultimately, blindness.

There have been previous efforts in obtaining RPECs through differentiation of human embryonic stem cells (hESCs) cells, however, these differentiation processes tend to be inefficient, time-consuming, and utilise exogenous growth factors and/or animal-derived sera.

The inventor of the present invention has found an efficient and compatible method for differentiating pluripotent stem cells into RPECs through components and culture systems that better reflect the natural series of signals that cells receive when being directed to become RPECs in vivo. Advantages of the method over other methods are (1) high efficiency and rapidness, (2) only requires small molecule chemical compounds, (3) compatible for human clinical trials, (4) rapid and extensive expansion of the hESC-RPECs produced by the method, (5) maturation of the hESC-RPECs in vitro without cytokines. In a further protocol that falls within the scope of the invention, eye field progenitor cell (EFPC) intermediates produced in the initial step of the three step differentiation procedure described below, can be induced towards rapid, efficient differentiation of PhR cells (PhRCs) using a modified small molecule, xeno-free culture system. All methods of cell culture, differentiation, expansion, and maturation, contained herein are performed under xeno-free, feeder-free and defined culture conditions, unless stated otherwise.

SUMMARY

In accordance with a first aspect, the invention provides an in vitro method for the rapid and efficient generation of mammalian eye field progenitor cells (EFPCs) comprising: (a) culturing mammalian SCs under defined, feeder-free, and/or xeno-free culture conditions, and (b) culturing said mammalian SCs in the presence of one or more antagonists to each of the TGF-β, BMP and WNT signalling pathways, and under defined, feeder-free, and/or xeno-free culture conditions, such that they differentiate to mammalian EFPCs.

In accordance with a second aspect, the invention provides an in vitro method for the rapid and efficient generation of mammalian eye field progenitor cells (EFPCs) comprising: (a) culturing mammalian PSCs under defined, feeder-free, and/or xeno-free culture conditions, and (b) culturing said mammalian PSCs in the presence of one or more antagonists to each of the TGF-β, BMP and WNT signalling pathways, under defined, feeder-free, and/or xeno-free culture conditions, such that they differentiate to mammalian EFPCs. In one embodiment, the PSCs are ESCs or IPSCs.

In accordance with a third aspect, the invention provides an in vitro method for the rapid and efficient generation of mammalian retinal pigment epithelial cells (RPECs) from mammalian SCs comprising: (a) culturing said mammalian SCs under defined, feeder-free, and/or xeno-free culture conditions, (b) culturing said mammalian SCs in the presence of one or more antagonists to each of the TGF-β, BMP and WNT signalling pathways, and under defined, feeder-free, and/or xeno-free culture conditions, such that they differentiate to mammalian EFPCs, and (c) culturing said mammalian EFPCs in the presence of agonists of one or more of Activin-A like and WNT signalling agonists, under defined, feeder-free, and/or xeno-free culture conditions, such that they differentiate to mammalian SC-derived RPECs.

In accordance with a fourth aspect, the invention provides an in vitro method for the rapid and efficient generation of mammalian retinal pigment epithelial cells (RPECs) from mammalian PSCs comprising: (a) culturing said mammalian PSCs under defined, feeder-free, and/or xeno-free culture conditions, (b) culturing said mammalian PSCs in the presence of one or more antagonists to each of the TGF-β, BMP and WNT signalling pathways, and under defined, feeder-free, and/or xeno-free culture conditions, such that they differentiate to mammalian EFPCs, and (c) culturing said mammalian EFPCs in the presence of agonists of one or more of Activin-A like and WNT signalling agonists, under defined, feeder-free, and/or xeno-free culture conditions, such that they differentiate to mammalian PSC-derived RPECs. In one embodiment, the PSCs are ESCs or IPSCs.

In accordance with a fifth aspect, the invention provides an in vitro method for the rapid and efficient generation of mammalian photoreceptors (PHs) from mammalian SCs comprising: (a) culturing mammalian SCs under defined, feeder-free, and/or xeno-free culture conditions, (b) culturing said mammalian SCs in the presence of one or more antagonists to each of the TGF-β, BMP and WNT signalling pathways, and under defined, feeder-free, and/or xeno-free culture conditions, such that they differentiate to mammalian EFPCs, (c) culturing said mammalian EFPCs in the presence of one or more antagonists of one or more of Notch, Wnt, CKI, and activators of Retinoic Acid (RA) and Hedgehog signalling, whereby the culturing of said EFPCs is towards photoreceptor progenitor cells and (d) culturing the cells generated from step (c) in the presence of one or more agonists of RA and Hedgehog signalling, and taurine, to generate mammalian SC-derived PhRs.

In accordance with an sixth aspect, the invention provides an in vitro method for the rapid and efficient generation of mammalian PhRs from mammalian PSCs comprising: (a) culturing said mammalian PSCs under defined, feeder-free, and/or xeno-free culture conditions, (b) culturing said mammalian PSCs in the presence of one or more antagonists to each of the TGF-β, BMP and WNT signalling pathways, and under defined, feeder-free, and/or xeno-free culture conditions, such that they differentiate to mammalian EFPCs, (c) culturing said mammalian EFPCs in the presence of antagonists of one or more of Notch, Wnt, CKI signalling, and activators of RA and Hedgehog signalling, towards photoreceptor progenitors and (d) culturing the cells generated from step (c) in the presence of one or more agonists of RA and Hedgehog signalling, and taurine, to generate mammalian PSC-derived PhRs. In one embodiment, the PSCs are ESCs or IPSCs.

In accordance with a seventh aspect, the invention provides an in vitro method for the rapid and efficient generation of human eye field progenitor cells (hEFPCs) comprising: (a) culturing hSCs under defined, feeder-free, and/or xeno-free culture conditions, and (b) culturing said hSCs in the presence of one or more antagonists of each of the TGF-β, BMP and WNT signalling pathways, and under defined, feeder-free, and/or xeno-free culture conditions, such that they differentiate to hSC-derived EFPCs.

In accordance with an eighth aspect, the invention provides an in vitro method for the rapid and efficient generation of human eye field progenitor cells (hEFPCs) comprising: (a) culturing hPSCs (for instance, hESCs or hIPSCs) under defined, feeder-free, and/or xeno-free culture conditions, and (b) culturing said hPSCs in the presence of one or more antagonists of each of the TGF-β, BMP and WNT signalling pathways, and under defined, feeder-free, and/or xeno-free culture conditions, such that they differentiate to hPSC-derived EFPCs.

In accordance with a ninth aspect, the invention provides an in vitro method for the rapid and efficient generation of human eye field progenitor cells (hEFPs) comprising: (a) culturing human embryonic stem cells (hESCs) under defined, feeder-free, and/or xeno-free culture conditions, and (b) culturing said hESCs in the presence of one or more antagonists to each of the TGF-β, BMP and WNT signalling pathways, and under defined, feeder-free, and/or xeno-free culture conditions, such that they differentiate to EFPCs.

In accordance with a tenth aspect, the invention provides an in vitro method for the rapid and efficient generation of human eye field progenitor cells (hEFPs) comprising: (a) culturing human induced pluripotent stem cells (hIPSCs) under defined, feeder-free, and/or xeno-free culture conditions, and (b) culturing said hIPSCs in the presence of one or more antagonists to each of the TGF-β, BMP and WNT signalling pathways, and under defined, feeder-free, and/or xeno-free culture conditions, such that they differentiate to EFPCs.

In accordance with an eleventh aspect, the invention provides an in vitro method for the rapid and efficient generation of human retinal pigment epithelial cells (RPECs) from hPSCs comprising: (a) culturing hPSCs under defined, feeder-free, and/or xeno-free culture conditions, (b) culturing said hPSCs in the presence of one or more antagonists to each of the TGF-β, BMP and WNT signalling pathways, and under defined, feeder-free, and/or xeno-free culture conditions, such that they differentiate to human EFPCs, and (c) culturing said human EFPCs in the presence of one or more agonists from the family of Activin-A like agonists, WNT signalling agonists, or a combination thereof, and under defined, feeder-free, and/or xeno-free culture conditions, such that they differentiate to human RPECs.

In accordance with a twelfth aspect, the invention provides an in vitro method for the rapid and efficient generation of human retinal pigment epithelial cells (RPECs) from hESCs comprising: (a) culturing hESCs under defined, feeder-free, and/or xeno-free culture conditions, (b) culturing said hESCs in the presence of more of more antagonists to each of the TGF-β, BMP and WNT signalling pathways, and under defined, feeder-free, and/or xeno-free culture conditions, such that they differentiate to human EFPCs, and (c) culturing said human EFPCs in the presence of one or more agonists from the family of Activin-A like agonists or WNT signalling agonists, or a combination thereof, and under defined, feeder-free, and/or xeno-free culture conditions, such that they differentiate to human RPECs.

In accordance with a thirteenth aspect, the invention provides an in vitro method for the rapid and efficient generation of human retinal pigment epithelial cells (RPECs) from human IPSCs (hIPSCs) comprising: (a) culturing hIPSCs under defined, feeder-free, and/or xeno-free culture conditions, (b) culturing said hIPSCs in the presence of one or more antagonists to each of the TGF-0, BMP and WNT signalling pathways, and under defined, feeder-free, and/or xeno-free culture conditions, such that they differentiate to human EFPCs, and (c) culturing said human EFPCs in the presence of one or more agonists from the family of Activin-A like agonists, or WNT signalling agonists, or a combination thereof, and under defined, feeder-free, and/or xeno-free culture conditions, such that they differentiate to human RPECs.

In one embodiment of the any of the above aspects, the one or more antagonists to each of the TGF-β, BMP and WNT signalling pathways is at least SB and either LDN or CKI. Preferably, SB, LDN and CKI. In addition, CKI may be CKI-7.

In accordance with a fourteenth aspect, the invention provides an in vitro method for the generation of RPECs from PSCs comprises:
(a) providing a cell culture of PSCs;
(b) culturing the PSCs within said cell culture in a culture system comprising base media supplemented with at least SB and either LDN or CKI, but in the absence of exogenous growth factors or animal-derived sera, wherein the stem cells are differentiated to EFPCs;
(c) culturing said EFPCs in a suitable culture system comprising a base media supplemented with at least IDE or CHIR, or both;
(d) dissociating the differentiated cells obtained from step (c) into single cells and seeding said cells in a suitable culture system comprising a suitable growth surface and base media to obtain PSC-derived RPE cells; and
(e) expanding the PSC-derived RPE cells in the absence of exogenous growth factors.

In an embodiment of the fourteenth aspect, the culture system in step (b) comprises base media that is supplemented with at least SB, LDN and CKI. In another embodiment, the base media is further supplemented with nicotinamide (NIC) and/or iROCK. In another embodiment, the base media defined in step (c) is further supplemented with iROCK. In a further embodiment, the base media defined in (d) is supplemented by one or both of iROCK and IDE. In another embodiment, iROCK is used in the above method when cells are dissociated. In another embodiment, the method of the fourteenth aspect further comprises the following step: (f) maturing the PSC-RPEs in a media to achieve a terminally differentiated functionality.

In an embodiment of any of the above aspects, the method does not involve use of conditioned medium.

In an embodiment, to obtain photoreceptor cells from the Eyefield, said culture contains CKI-7, DAPT, Purmorphamine (Pur), and Retinoic Acid for 4-6 days to obtain photoreceptor precursor cells, followed by culture in Pur and RA to obtain photoreceptors.

According to another embodiment, one or more of the following supplements may be used in the method: Taurine, forskolin, rolipram, and SU5402 which is 2-[(1,2-Dihydro-2-oxo-3H-indol-3-ylidene)methyl]-4-methyl-1H-pyrrole-3-propanoic acid, or any derivate or substitute of the components described herein, or any combination thereof.

In a further embodiment, the time to complete step (b) is about 6 days+/−3 days, or preferably about 6 days+/−2 days, or more preferably 6 days+/−1 day, or most preferably is 6 days.

In a further embodiment, the time to complete step (c) is about 7 days+/−3 days, or preferably about 7 days+/−2 days, or more preferably 7 days+/−1 day, or most preferably is 7 days.

In a further embodiment, the time to complete steps (a), (b), (c), and (d) is about 14 days+/−7 days or +/−6 days, or +/−5 day or +/−4 days or +/−3 days or +/−2 days or +/−1 days, or exactly 14 days.

In another embodiment, the PSCs are human embryonic stem cells (hESCs) or induced pluripotent stem cells (IPSC). In a preferred embodiment, the PSCs are a hESC cell line. In one example, the cell line is Mell. Other hESC cell lines, such as Genea 002 or Genea 015, may be used. Commercially available hESCs can be also used in accordance with the invention. hESCs can be purchased from the NIH human embryonic stem cells registry. Non-limiting examples of commercially available embryonic stem cell lines are WA09, BG01, BG02, BG03, BG04, CY12, CY30, CY92, CY10, TE03 and TE32.

In another embodiment, the RPE cells obtained by the methods described herein are expanded and matured on a suitable surface in a defined media that enhances their terminal differentiation and maturation to RPE cells with mature characteristics. In a further embodiment, feeder free conditions using a defined media and acellular surface substrate may be used for the hESC culturing system of the invention. In one example, the defined media is mTeSR™1 and the suitable growth surface (substrate) is BD Matrigel™.

In another embodiment, the PSCs used for the generation of RPE cells via the methods described within, are cultured, maintained, and/or prepared for the process of differentiation by culture in a completely defined and xeno-free culture system, whereby neither the surface substrate, nor the culture medium contain components that would disqualify them from achieving GMP, or cGMP standard certification. Non-limiting examples of such xeno-free surface substrates for culturing PSCs include Vitronectin XF, and LN521 (Laminin α5β2γ1). Non-limiting examples of defined and xeno-free Stem Cell culture media include TeSR™-E8, mTeSR™2 and cGMP mTeSR™1 (StemCell Technologies).

In another embodiment, the PSCs are differentiated towards EFPCs under adherent conditions prior to single cell dissociation and subsequent aggregation to form floating cell aggregates. These cell aggregates, termed anterior neural ectodermal bodies (ANEBs), are grown under low-attachment conditions for a number of days, before being seeded onto a suitable surface substrate, in order to co-stimulate outgrowth and directed differentiation towards RPE. Following a period of adherent outgrowth of a number of weeks, such as two weeks as an example, the resultant PSC-RPE cells are dissociated into single cells and seeded onto, and then cultured on, a suitable surface for tertiary differentiation and/or expansion.

In another embodiment, adherent EFPCs are obtained from differentiating PSCs, which are in turn obtained from prior single cell dissociation of human pluripotent stem cell (hPSC) colonies, and then cultured in continuous adherent culture with no period of floating aggregates. These EFPCs are subsequently dissociated into single cells and seeded onto a suitable surface for further expansion and secondary differentiation, after which they are dissociated into single cells and seeded onto, and then cultured on, a suitable surface for tertiary differentiation and/or expansion.

In another embodiment, PSC colonies are triggered to EFPC differentiation, without prior single cell dissociation, by being cultured directly in a media comprising the combinations of small molecules used for primary differentiation, followed by secondary differentiation conditions. These cells are subsequently dissociated into single cells and seeded onto a suitable surface for further expansion and tertiary differentiation to RPE cells.

In another embodiment, hPSC colonies are dissociated into single cells and aggregated directly into embryoid bodies (EBs), without a prior period of differentiation, and are then cultured under low attachment conditions while being exposed to the combinations, timing and concentrations of small molecules used for primary and then secondary differentiation. In one embodiment these EBs, containing EFPCs, may then be dissociated into single cells and seeded onto a suitable surface for further expansion and continued secondary differentiation. In another embodiment the EBs, containing EFPCs, may be seeded whole onto a suitable surface and exposed to the combinations of small molecules used for continued secondary differentiation. In both cases the cells are subsequently dissociated into single cells and seeded onto a suitable surface for further expansion and tertiary differentiation to RPE cells.

In accordance with a fifteenth aspect, the invention provides a kit comprising one or more antagonists as defined in the above methods. The kit may comprise one or more antagonists to each of the TGF-β, BMP and WNT signalling pathways. The kit may further include one or more agonists of the Activin-A like agonists, or WNT signalling agonists, or a combination thereof. The kit may also include one or more antagonists of one or more of Notch, Wnt, CKI, and activators of Retinoic Acid (RA) and Hedgehog signalling. The kit may include at least SB and either LDN or CKI. The kit may include SB, LDN and CKI. The CKI may be CKI-7. The kit may also include at least IDE or CHIR, or both. The molecules would be supplied in media. The kit would include a base media that is supplemented with at least SB, LDN and CKI. In another embodiment, the base media is further supplemented with nicotinamide (NIC) and/or iROCK. In another embodiment, the kit contains further base media that is supplemented with iROCK. In a further embodiment, the further base media is supplemented by one or both of iROCK and IDE.

Further, the kit does not contain conditioned medium.

The kit may also contain one or more of the following supplements: Taurine, forskolin, rolipram, and SU5402 which is 2-[(1,2-Dihydro-2-oxo-3H-indol-3-ylidene) methyl-4-methyl]-1H-pyrrole-3-propanoic acid, or any derivate or substitute of the components described herein, or any combination thereof.

In a further embodiment, the kit contains instructions for use of the method.

Optionally, the kit contains cells for differentiation in accordance to the method of the invention. In another embodiment, the cells are PSCs. Further, the PSCs are human embryonic stem cells (hESCs) or induced pluripotent stem cells (IPSC). In a preferred embodiment, the PSCs are a hESC cell line. In one example, the cell line is Mel1. Other hESC cell lines, such as Genea 002 or Genea 015, may be used. Commercially available hESCs can be also used in accordance with the invention and contained in the kit. hESCs can be purchased from the NIH human embryonic stem cells registry. Non-limiting examples of commercially available embryonic stem cell lines are WA09, BG01, BG02, BG03, BG04, CY12, CY30, CY92, CY10, TE03 and TE32.

In another embodiment, the kit comprises defined media such as mTeSR™1 and the suitable growth surface (substrate) of BD Matrigel™. In another embodiment, the kit comprises a completely defined and xeno-free culture system, whereby neither the surface substrate, nor the culture medium contain components that would disqualify them from achieving GMP or cGMP standard certification. Non-limiting examples of such xeno-free surface substrates for culturing PSCs include Vitronectin XF, and LN521 (Laminin α5β2γ1). Non-limiting examples of xeno-free Stem Cell culture media include TeSR™-E8, mTeSR™2, and cGMP mTeSR™1.

In addition to the above, any other entity that could be an equivalent substitute for the molecules, substrates, and cells mentioned above is within the scope of the invention. Also, any additional entities that may improve the effectiveness of the methods that are known in the field (e.g. existing media that are used for growing similar cell types) are also contemplated herein.

Definitions

The term "mammal" includes both human and non-human mammals. Examples of mammals include, but are not limited to: humans and veterinary and laboratory animals, such as pigs, cows, goats, cats, dogs, rabbits and mice. The term "subject" includes both human and veterinary subjects, for example, non-human primates, dogs, cats, horses, rabbits, pigs, mice, rats, cows, as well as species of particular interest, such as members of the marsupial and monotreme groups.

A "cell" as used herein refers to a single cell, as well as to a population of (i.e. more than one) cells. The population may be a pure population comprising one cell type. Alternatively, the population may comprise more than one cell type. The term cell may denote a single cell, a cluster of cells, or can be used to name population of cells (i.e., a neural stem cell).

"Stem cells" and "SCs", as used herein, are interchangeable and refer to cells which under suitable conditions are capable of differentiating into other cell types having a particular, specialized function while under other suitable conditions are capable of self-renewing and remaining in an undifferentiated state. Non-limiting examples of stem cell types include pluripotent stem cells, multipotent stem cells, adult stem cells, bi-potent stem cells, and uni-potent stem cells.

"Progenitor cells", "progenitors", "precursor cells", "precursors", as used herein, as interchangeable and refer to cells that share the characteristic of stem cells that they are not terminally differentiated cell types, and retain differentiation potential, but are not capable of remaining in an undifferentiated state via self-renewal for prolonged periods of time. In some cases, cells thought to be progenitor cells may actually have the innate ability to self-renew, though it may not be known in the art, or they may subsequently acquire the characteristic of self-renewal through experience in culture, and thus come to be defined as a stem cell at a later point in time.

The acquisition of stem cell characteristics by non-stem cells may be the product of adaptation to cell culture conditions, particularly under stressful conditions that have been shown to encourage cells to switch on stem cell-like characteristics. The manipulation of cells such that they acquire stem cell-like characteristics may be achieved by, but not limited to, the manipulation of cell culture conditions, including: surface substrate, culture medium, serum component, growth factors, small molecules, cell density, cell culture format, hypoxia, or the selection, or enrichment, of a subset of cells that are either stem cells, or acquire stem cells characteristics via the examples given above, from within a heterogeneous cell culture.

"Human stem cells" and "hSCs", as used herein, are interchangeable and refer to stem cells of human origin and includes, without being limited thereto, cell types of germ line, embryonic, foetal, amniotic, umbilical cord and adult origin, whether natural or artificially induced. Other hSCs include, without being limited thereto, hematopoietic or mesenchymal stem cells obtained from bone marrow, adipose, blood tissue of an individual at any age or from cord blood or tissue of a newborn individual, neural stem cells obtained from fetal, any age post birth, cells that have been transdifferentiated to become a cell type that is capable of differentiating to RPE cells, or cadaver brain or other multipotent or adult stem cell types.

"Pluripotent stem cells", "Pluripotent SCs", or "PSCs", as used herein, refer to uncommitted stem cells or precursor cells that have the ability to form cell derivatives from any of the three germ layer lineages (ectoderm, mesoderm, or endoderm), and in some cases may form extra-embryonic cell types, such as trophoblasts, and may even form gametes. Human pluripotent SCs include human embryonic stem cell (hESC) and induced pluripotent stem cells (IPSC). Other pluripotent SCs include embryonic germ (EG) cells obtained from the genital tissue of a foetus any time during gestation, preferably before 10 weeks of gestation, multipotent adult progenitor cells (MAPCs) and amniotic fluid stem cells. For the purposes of simplicity, these various types of human pluripotent stem cells may be collectively referred to as "hPS cells", "hPSC", "hPSCs", "human pluripotent stem cells", or "human PSCs." To simply describe these cells for the purpose of this invention, human pluripotent SCs cells are cells with the ability to form cells of all three germ-lineage layers of the embryo, and of particular relevance to this invention are their ability to differentiate along the ectodermal lineage to form retinal cell derivatives (such as RPE cells, rod and cone photoreceptors, bipolar cells, amacrine cells, retinal ganglion cells, muller cells and horizontal cells), and the intermediate cell types that ultimately give rise to them (for example, eye field progenitor cells, neural retinal progenitor cells, photoreceptor progenitor cells).

"Human embryonic stem cell" or "hESC", "Pluripotent embryonic stem cell", "Pluripotent stem cell" or "PSC", as used herein, refer to a cell which can give rise to any differentiated cell types in an embryo or an adult, including the germ cells (sperm and eggs). Human embryonic stem cells can be obtained from the embryonic tissue formed after fertilization (e.g., blastomere, blastocyst) using well-known cell-culture methods (see Thomson et al. [U.S. Pat. No. 5,843,780; Science 282:1145, 1998; Curr. Top. Dev. Biol. 38:133, 1998; Proc. Natl. Acad. Sci. USA 92: 7844, 1995]; Bongso et al. [Hum Reprod 4: 706, 1989]) or produced by artificial means (such as by somatic cell nuclear transfer, or by induction of pluripotency as per IPSC generation) that have equivalent characteristics. Such cells are true pluripotent cell lines in that they: (i) are capable of extensive proliferation in vitro in an undifferentiated state; and (ii) are capable of differentiation to derivatives of all three embryonic germ layers (endoderm, mesoderm, and ectoderm) even after prolonged culture.

"Photoreceptor", "Photoreceptor cell", "PhR cells", "PhRCs", which may be used interchangeably as the context allows, mean cells of a group of related cell types functionally similar to that of the group of photoreceptors found mammalian eye, consisting of the rod and various cone photoreceptor types (i.e., Cone photoreceptors may be further subdivided into cones that have the ability to detect different ranges of light wavelengths, such as S-cones, M-cones and L-cones).

"Photoreceptor progenitor cells", "PhRPCs", "PhRP cells", which may be used interchangeably as the context allows, means a precursor cell with the ability to differentiate into at least one type of photoreceptor cells. In the context of development, photoreceptors progenitor cells are cell of the neural retinal lineage. In the context of this disclosure, PhRP cells are differentiated from eyefield progenitor cells, and can give rise to photoreceptor cells.

"Cell culture" and "Cultured cell", as used herein, refer to cells or tissues that are cultured, cultivated or grown in an artificial, in vitro environment.

"Culture system", as used herein, refers to an in vitro system suitable for the propagation, or maintenance, of cells in vitro. The term denotes a combination of components, at minimum including a basic medium (a cell culture medium usually comprising a defined base solution, which includes salts, sugars and amino acids). The culture system in accordance with the invention may further comprise even more components such as, without being limited thereto, a serum replacement, a culture (nutrient) medium and other added factors, which together provide suitable conditions that support cell growth and differentiation as well as other components typically used in cell culture systems, such as B-27 and N-2 supplements (Life Technologies), and triiodothyronine (T3; Sigma). The above components may be collectively classified as soluble components. The components may also be associated to a carrier, i.e. non-soluble components. The association may be by chemical or physical attachment/binding. For example, the component may be immobilized onto a matrix (e.g. extracellular matrix), presented by cells added to the system or bound to biodegradable material. Further, the component may be released from a carrier, the carrier may be a cell or a vesicle encapsulating or embedding the component. Thus, in the following text, components supplementing the basic media to form the culture system comprise both soluble and non-soluble components and sometimes referred to in this specification as supplements.

"Feeder-free", as used herein, refers to a cell culture system that does not employ third party cells (i.e., cells that are not themselves the subject of investigation or manipulation) in a co-culture system to support the culture, growth, differentiation, maturation or function of the cells of interest. A common example of a feeder cell is the use of irradiated mouse embryonic fibroblasts (MEFs) to support the culture of human embryonic stem cells.

"Conditioned medium", as used herein, refers to a medium that has been harvested after it has been in contact with a cell culture. The purpose of conditioning a medium is generally to infuse it with the mixture of undefined proteins, glycoproteins etc., that a cell releases, in order to expose these factors to a different cell culture. Conditioned medium is a crude, undefined, but often effective way to generate a medium that is able to support or enhance the culture, growth, differentiation, maturation or function of a cell, when it is applied to a different cell culture. A common example of a conditioned medium is the use of MEF conditioned medium to support human embryonic stem cells cultures, in when cultured in the absence of irradiated-MEF feeder cells.

"Chemically defined", or "defined" as used herein, refers to components of cell culture, such as a "chemically defined medium" or a "chemically defined surface substrate", and is taken to mean that all of the chemical components and concentrations of the medium or surface substrate are known. In order to be chemically defined, a medium must contain recombinant sources any required proteins and other factors.

"Xeno-free", as used herein, refers to the absence of animal-derived components. This is commonly used to refer to components of cell culture, such as media and surface substrata, and is taken to mean that all components are either human, or chemically defined.

"Defined and xeno-free", and "xeno-free and defined" as used herein, refers to a culture system that meets both the criterion of being xeno-free, and defined. By definition, such culture systems are feeder-free.

"cGMP", or GMP" is an acronym for "current Good Manufacturing Practices" and means the laboratory and clinical practices required in order to conform to guidelines recommended by agencies that control authorization and licensing of, for example, medical devices. The most central aspects of cGMP are traceability and accountability throughout a products development and production. "Direct" and "directed", as used herein, are interchangeable unless the context dictates otherwise, and refer to initiating non-spontaneous differentiation of stem cells into RPE cells.

"Differentiation", as used herein, refers to the process of switching the state of a cell from one cell type to another. An example of differentiation in the context of the present disclosure is the process of a cell changing from a pluripotent stem cell to an eyefield progenitor cell. Cell states that occur during differentiation may be transient, stable, or terminal in nature. Those skilled in the art understand that differentiation may be permanent, or non-permanent.

"Non-directed differentiation", or "spontaneous differentiation" as used herein, refers to the process of cell differentiation that results in the differentiation of a cell or cell population towards fates that are not strictly controlled, or not intended to yield a single cell type. The non-directed differentiation of stem cells is often performed in the absence of extrinsic signalling, or the removal of maintenance factors, or the by the disruption of self-renewal, and often produces more than one cell type. Non-directed differentiation may generate heterogeneous cultures of cells that interact through the establishment of complex cell adhesions and paracrine signalling mechanisms, and affect the behaviour, response, fate or function of other cells within the said heterogeneous culture. In some cases, the heterogeneous cultures may come to resemble, or acquire features of, an organ or tissue related to the identity of the cells contained therein. An example of non-directed differentiation that is known in the field is the spontaneous differentiation of human pluripotent stem cells via the removal of self-renewal factors, such as bFGF, resulting in the differentiation of said cells towards various cell types the three primary germ lineages (mesoderm, endoderm and ectoderm), and is often used as a crude test of pluripotency in vitro. Another important form of non-directed differentiation is the generation of organoids, whereby cells that have the capacity to differentiate into more than one cell type of a tissue of interest, are cultured in an environment that allows cell heterogeneity to develop, and resulting in mixed populations of cells that interact through the establishment of complex cell adhesions and paracrine signaling, and affect the behaviour, response, fate or function of other cells within the culture, such that they generate multicellular structures that contain features of a specific tissue type, or organ, such as cell organisation and architecture. An example of an organoid culture that is known in the field is the differentiation of stem cells to retinal organoids, which are often comprised of RPECs, photoreceptors, and other retinal cell derivatives, with organised cell arrangement and extracellular matrices that reflect the architecture of the native retina.

"Direct", "directed", and "directed differentiation" as used herein, are interchangeable unless the context dictates otherwise, and are commonly used in the context of cell differentiation and refer to the instruction of a cell to differentiate in a non-spontaneous and/or non-random fate, toward a different cell fate. Another way to describe directed differentiation is the deliberate instruction of a cell, or cell culture, to change from one cell type to another cell type that is desired, or intended. Directed differentiation often involves exposing a culture of cells to differentiation factors (such as, but not limited to, cytokines, or small molecules) that manipulate the cell toward a change that is a) deliberate, or b) controllable, or c) repeatable, and generally a), b) and c). Features of methods for directed differentiation are highly valuable if they are able to achieve differentiated cell cultures that are highly pure, produce cells with the desired function, produce cells that are in vitro equivalents of a cell that is not convenient, or not possible, to isolate from an organism, produce cells in a reliable manner, produce cells in a robust manner, produce cells in a reproducible manner, produce cells that are without genetic or epigenetic defect as a result of the process of directed differentiation, produce cells that can be used for transplantation into an experimental animal subject, or produce cells that are deemed suitable for transplantation into a human, particularly when the intended purpose of said cell transplantation is a form of cell therapy. In the context of the present disclosure, the goal of directed differentiation may be towards retinal cell derivatives, such as the retinal pigmented epithelial cells, that may be used for the treatment of retinal conditions that may benefit from cell transplantation. A non-limiting example is the transplantation of human stem cell derived RPE cells to treat macular degeneration.

As used herein, the term "cell type" refers to a distinct morphological or functional form of a cell, and may also be identified using characteristics. Non-limiting characteristics that may be used to identify a cell type include gene expression, or epigenetic profile, or non-coding RNA profile, or protein expression, or cell surface markers, or by differentiation potential, or proliferative capacity, or response to stimuli or signals, or anatomical location, or timing of appearance during development.

"Differentiating SCs", as used herein, refer to SCs which, under suitable conditions capable of differentiating SCs in a directed fashion into a pre-determined fate, or simply a different fate; the term also referring to a population of SCs in which at least part thereof has already been induced to undergo at least initial differentiation, namely directed differentiation or combination of same.

"Primary differentiation", as used herein, refers to the initial differentiation of pluripotent stem cells from a pluripotent state towards the eye field via an anterior neural ectodermal state.

"RPE cell specification", or equivalent terms such as "RPEC specification", "RPEC differentiation", as used herein, refers to the directed differentiation of said eye field cells towards the retinal pigmented epithelial cell fate.

"RPE cell expansion", or equivalent terms such as "RPEC expansion", as used herein, refers to the reinforcement of the RPE cell identity, coupled with the expansion of cell numbers by regular passage and enrichment.

"Terminal differentiation", as used herein, refers to the establishment of stem cell-derived SC-RPE cell cultures with morphological, molecular, and functional characteristics that are similar to native human RPE cells.

"EFPCs" is an acronym for "eye field progenitor cells" and is used herein to describe cells that are, or share characteristics with, cells of anterior neural ectodermal origin that have the developmental potential to generate retinal cell types. EFPCs have the characteristics of at least low/null Oct4 expression, but may also have low/null Nanog expression. EFPCs also exhibit expression of at least one of Otx2, Pax6, LHX2, or Rax expression, and have the developmental competence to produce retinal cell derivatives.

"EFPC state" as used herein, refers to a set or combination of cellular molecular markers, which should include low/null Oct4 and/or Nanog expression, increased Pax6, Obtx2, LHX2, and Rax expression, and have the developmental competence to produce retinal cell derivatives.

"Embryoid Bodies", or "EBs", as mentioned herein refer to three-dimensional aggregates of pluripotent stem cells, and are commonly floating in culture for a period of time, and optionally seeded back onto an appropriate cell culture surface. EBs may be cultured in a medium that allows them to spontaneously differentiate. These cells can undergo differentiation into cells of the endodermal, mesodermal and or ectodermal lineages. In contrast to monolayer cultures, the spheroid structures that are formed when pluripotent stem cells aggregate enables the non-adherent culture of EBs in suspension, which is useful for bioprocessing approaches. The three-dimensional structure, including the establishment of complex cell adhesions and paracrine signalling within the EB microenvironment, enables differentiation and morphogenesis.

"ANEB" is an acronym for "anterior neural ectodermal body" and is used herein to describe embryoid bodies that are derived from the aggregation of stem cells that have been exposed to differentiation conditions for at least 12 hours, such that they share some of the molecular characteristics of EFPC state, for example, reduced expression of pluripotent cell markers, for example Oct4 or Nanog, and increased expression of neural ectodermal, anterior neural ectodermal, or eyefield markers, such Pax6 (−5a), Pax6 (+5a), LHX2, Otx2 or Rax, and have the potential to differentiate into Rax positive early-eye field cells.

"Retinal cell derivatives", as used herein refers to cells that comprise the inner and outer retina of the eye, their in vitro equivalents, or the progenitor cells from which they are derived. These cells include, but are not limited to, retinal pigmented epithelial cells, the cells of the neural retinal layer, including rod and cone photoreceptors, bipolar cells, amacrine cells, retinal ganglion cells, muller cells and horizontal cells. Further examples of progenitor cells that are considered to be retinal cell derivatives that, in turn, give rise to more specialised retinal cell types, include, but are not limited to, neural retinal progenitor cells and photoreceptor precursor cells.

"Retinal pigment epithelial cells", "RPE cells", "RPEs", which may be used interchangeably as the context allows, mean cells of a cell type functionally similar to that of native RPE cells which form the pigmented cell layer of the retina (e.g. upon transplantation within an eye, they exhibit functional activities similar to those of native RPE cells). Thus, the terms "retinal pigment epithelial cells", "RPE cells", or "RPEs" may be used herein to refer to both native RPE cells of the pigmented layer of the retina and RPE cells differentiated in a directed fashion from SCs, in accordance with the present disclosure.

"SC-derived RPE cells", "SC-RPE cells", "SC-RPE", which may be used interchangeably as the context allows, are used herein to denote RPE cells that are obtained by directed differentiation from SCs. Where the SCs are of human origin, the terms "hSC-derived RPE cells", "hSC-RPE cells", "hSC-RPE", are used. Preferably, where the SCs are hESCs, the terms "hESC-derived RPE cells", "hESC-RPE cells", "hESC-RPE", are used interchangeably herein in which the hESC-derived RPE cells are mature (terminally differentiated) and functional RPE cells as exhibited by parameters defined herein below.

"PSC-derived RPE cells", "PSC-RPE cells", "PSC-RPE", "PSC-derived RPECs", "PSC-RPECs", which may be used interchangeably as the context allows, are used herein to denote RPE cells that are obtained by directed differentiation from PSCs. Where the PSCs are hPSCs, the terms "hPSC-derived RPE cells", "hPSC-RPE cells", "hPSC-RPE", "hPSC-derived RPECs", "hPSC-RPECs", "hPSC-RPECs", are used. Preferably, where the PSCs are hESCs, the "hESC-derived RPE cells", "hESC-RPE cells", "hESC-RPE", "hESC-derived RPECs", "hESC-RPECs", "hESC-RPECs", "hESC-derived RPE cells", "hESC-RPE cells", "hESC-RPE", are used interchangeably herein in which the hESC-derived RPE cells are mature (terminally differentiated) and functional RPE cells as exhibited by parameters defined here in below. Preferably, where the PSCs are hIPSCs, the "hIPSC-derived RPE cells", "hIPSC-RPE cells", "hIPSC-RPE", "hIPSC-derived RPECs", "hIPSC-RPECs", "hIPSC-RPECs", are used interchangeably herein in which the hIPSC-derived RPE cells are mature (terminally differentiated) and functional RPE cells as exhibited by parameters defined here in below.

"SC-derived Photoreceptor cells", "SC-PhR cells", "SC-PhRs", "SC-PhR", "SC-derived PhRCs", "SC-PhRCs", which may be used interchangeably as the context allows, are used herein to denote Photoreceptor cells that are obtained by directed differentiation from SCs. Preferably, when the SCs are of human origin, the terms, "hSC-PhR cells", "hSC-PhRs", h"SC-PhR", "hSC-derived PhRCs", "hSC-PhRCs" are used interchangeably herein.

"PSC-derived Photoreceptor cells", "PSC-PhR cells", "PSC-PhRs", "PSC-PhR", "PSC-derived PhRCs", "PSC-PhRCs", which may be used interchangeably as the context allows, are used herein to denote Photoreceptor cells that are obtained by directed differentiation from PSCs. Where the PSCs are hPSCs, the terms "hPSC-derived Photoreceptor cells", "hPSC-PhR cells", "hPSC-PhR", "hPSC-derived PhRCs", "hPSC-PhRCs", "hPSC-PhRCs", are used. Preferably, where the PSCs are hESCs, the "hESC-derived PhR cells", "hESC-PhR cells", "hESC-PhRs", "hESC-derived PhRCs", "hESC-PhRs", "hESC-PhRCs", are used interchangeably herein in which the hESC-derived PhR cells are mature (terminally differentiated) and functional PhR cells, as exhibited by parameters defined here in below. Preferably, where the PSCs are hIPSCs, the "hIPSC-derived PhR cells", "hIPSC-PhR cells", "hIPSC-PhRs", "hIPSC-derived PhRCs", "hIPSC-PhRCs", "hIPSC-PhRs", are used interchangeably herein in which the hIPSC-derived PhR cells are mature (terminally differentiated) and functional PhR cells as exhibited by parameters defined here in below.

The term "directed differentiation" is to be understood as meaning the process of manipulating SCs under culture conditions which induce or promote differentiation into a target, or desired cell type. In the context of this invention, SCs may undergo directed differentiation to eyefield progenitor cells, retinal cell derivatives, such as RPE cells or photoreceptors, or to the differentiation of cells that are capable of further differentiating to retinal cell derivatives.

"Suitable growth surface", "suitable surface substrate" and "suitable surface", which are used interchangeably, refer to the surface or substrate on which the cells grow in cell culture, and forms part of the cell culture system. The standard surface for many cell types is known as TCP (tissue culture plastic) and is an uncoated plastic that has been treated to enhance the attachment and growth of many cell types. The growth and behaviour of many cell types are improved by or even require that TCP is coated with an additional substrate. As such suitable surfaces for various cell types may include, but are not limited to, Matrigel™ (BD Bioscience), Corning® Matrigel® Growth Factor Reduced (GFR) Basement Membrane Matrix (gfrMG) (Cornming, Mass., USA), L7™ (Lonza), Vitronectin XF™ (StemCell Technologies), Laminins including the pure laminins LN 111, LN522, LN521 and Collagen.

"Cell delivery system", "cell delivery device", "scaffold", "membrane", "prosthetic" which are used interchangeably refer to non-cellular entities that can be used in combination with cells to form an implant. Non-limiting examples of the possible functions that cell delivery systems may perform include: 1) delivering cells in a functional state to the appropriate location for transplantation, 2) forming a surface that cells prefer for growth and development to reach a state of maturity that is compatible with, or appropriate for, treatment, 3), shielding the cells from assault within the body, 4) encouraging the integration and function of the implant, or cells, within the implanted area, 5) serving the role of a prosthetic for a biological component (e.g., a membrane), 6) forming a physical barrier, 7) forming a diffuseable membrane that allows the diffusion of components, waste, nutrients, macromolecules etc. Cell delivery systems may have the appearance of the native structure with they replace, but this may also be unnecessary. Cell delivery systems may be used to functionally replace failing components, such as a membrane, and need not bare any morphological resemblance to the native component they are replacing. Depending on the context, it is thought that for a cell delivery system to be effective as a prosthetic, is should be able to functionally replace at least one of the functions of the component it is replacing, or alleviate a problem cause by the component it is replacing. In the context of treating retinal diseases, a cell delivery device may be required to replace the damaged Bruch's membrane, enable, or encourage the growth, delivery, survival, integration, or function of retinal cell derivatives, or retinal progenitor cells into the retina of a subject's eye to provide improved vision, or to allow study the effect of cell transplantation.

Cell delivery systems may be constructed from naturally occurring biological materials, such as proteins, silks, collagens, ECMs, decellularized organs or matrices derived from human, or non-human organisms. In addition, cell delivery systems may be composed of synthetic materials, such as polymers. Cell delivery systems may take the form of scaffolds, membranes, gels, hydrogels, and may be long-lasting, or dissolvable. Cell delivery systems may be viscous, hard, stiff or flexible, depending on purpose and the function that they are required to perform.

"LDN" is a term that represents a group of inhibitors of BMP via ALK 1, ALK 2, ALK 3 & ALK 6. An example of one inhibitor of LDN is LDN193189.

"SB" is a term that represents a group of inhibitors of the activin receptor-like kinase (ALK) receptors, ALK5, ALK4 and ALK7. An example of one inhibitor of SB is SB431542 which is a drug candidate developed by GlaxoSmithKline (GSK). It also suppresses the TGF-beta-induced proliferation of osteosarcoma cells in humans.

"CKI" is an abbreviation of Casein Kinase Inhibitor, which relates to inhibitors of the Casein Kinase family that are involved in the modulation of Wnt and Hedgehog signaling. CKI-7 is a member of the CKI family, as is Epiblastin A.

"NIC", or "Nic", is an abbreviation of nicotinamide which is a Vitamin B3 relative used for differentiation of hESC to RPE.

"CHIR" is a term that represents a group of molecules that mimic WNT signalling. An example of a CHIR molecule is CHIR99021 which mimics WNT signalling by the inhibition of GSK3F, resulting in stabilisation of β-catenin. Other members of CHIR may use different mechanisms and the following link provides further support for this aspect: http://www.scbt.com/datasheet-222416-wnt-agonist.htm.

"IDE" is a term that refers to a group of molecules that can functionally replace Activin A, whereby their activity results in SMAD2 signaling. Examples of IDE family members include IDE-1 and IDE-2.

"iROCK" is an acronym of inhibitor of Rho Associated Protein Kinase. iROCK prevents apoptosis of dissociated cells, extends proliferative capacity of some cell types, enhances cell viability after thawing following cryopreservation, and may play a role in differentiation. An example of an iROCK molecule is Y27632.

"Exogenous growth factors" and "cytokines" are used interchangeably and refer to proteinaceous factors, whether recombinant or isolated from natural sources, including but not limited to growth factors, cytokines, which individually, or in combination, have a measurable effect on cultured cells, such as providing pro- or anti-differentiation signals, and or pro- or anti-proliferative signals.

"animal sera" or "animal serum" or "animal-derived sera" mean a biological product or component derived from the acellular parts of animal or human blood and containing undefined numbers and amounts of growth factors, cytokines and other proteins.

"Activin" relates to members of the transforming growth factor beta (TGF-beta) superfamily which participate in regulation of several biological processes, including cell differentiation and proliferation. Activin A is a member of this family that mediates its biological effects through a complex of transmembrane receptor serine/threonine kinases, and binds to specific Activin A receptors. An exemplary sequence for Activin A is provided in GEN-BANK® Accession No. NM_002192.

"IGF-I" means the insulin-like growth factor.

The term "derivative" means a compound or molecule that is similar to another compound or molecule in the sense of (1) belonging to the same family of molecules or compounds and/or (2) sharing functionality.

"Agonist" or "Inducer" is an agent that either directly or indirectly positively affects the function of cellular components, such as enzymes, receptors, or signaling pathways. Agonists may be existing components of cellular machinery, such as naturally occurring cytokines, and may be purified from living organisms or generated in vitro. An agonist may also be a substance that is able to mimic the biological effect of a naturally occurring substance. In the context of this invention, and agonist most often refers to a small molecule that alters cell function by promoting the function of signalling pathways, or cellular components. An example of an agonist that results in a positive stimulation of a signalling pathway using an indirect mechanism is the small molecule inhibitor of GSK3b, CHIR99021. CHIR99021 mimics the gross output of canonical WNT signalling by inhibition the function of GSK3b, which results in the stabilisation of b-catenin. Therefore, although CHIR99021 is a chemical inhibitor of protein GSK3b, it ultimately behaves as an agonist of the canonical WNT signalling pathway.

"Antagonist" or "Inhibitor" is an agent that either directly or indirectly negatively affects the function of cellular components, such as enzymes, receptors, or signalling pathways. Antagonists may be existing components of cellular machinery, such as naturally occurring cytokines, and may be purified from living organisms or generated in vitro. An antagonist may also be a substance that is able to mimic the biological effect of a naturally occurring substance. In the context of this invention, and antagonist most often refers to a small molecule that alters cell function by negatively affecting the function of signalling pathways, or cellular components. An example of an antagonist that results in the inhibition of a signalling pathway is the small molecule SB431542 which inhibits the function of the activin receptor-like kinase (ALK) receptors, ALK5, ALK4 and ALK7 by binding to them, and disrupting their ability to transduce a signal in response to a ligand binding. An example of a ligand of the ALK receptors is Activin A.

Unless defined otherwise, all technical and scientific terms used herein have the same meaning as commonly understood by one of ordinary skill in the art (e.g. in cell biology, chemistry, molecular biology and cell culture). Standard techniques used for molecular and biochemical methods can be found in Sambrook et al., Molecular Cloning: A Laboratory Manual, 3rd ed. (2001) Cold Spring Harbor Laboratory Press, Cold Spring Harbor, N.Y. and Ausubel et al., Short Protocols in Molecular Biology (1999) 4th Ed, John Wiley & Sons, Inc.—and the full version entitled Current Protocols in Molecular Biology.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, reference to numerical values, unless stated otherwise, is to be taken as meaning "about" that numerical value. The term "about" is used to indicate that a value includes the inherent variation of error for the device and the method being employed to determine the value, or the variation that exists among the study subjects.

It also is to be understood, although not always explicitly stated, that the reagents, components, and supplements described herein are exemplary and that equivalents of such are known in the art and are within the scope of the invention.

The reference to any prior art in this specification is not, and should not be taken as an acknowledgement or any form of suggestion that prior art forms part of the common general knowledge.

The entire content of all publications, patents, patent applications and other material recited in this specification is incorporated herein by reference.

BRIEF DESCRIPTION OF THE DRAWINGS

FIG. 21. (A) Fluorescence microscopy image showing hESC-RPE cells after phagocytosis of microspheres (red), with nuclei shown stained by Hoechst staining (blue). (B) Confocal microscopy z-stack image showing internalisation of microspheres (red) under the apical cell membrane/microvilli, with phalloidin-488 stained f-actin (green).

FIG. 24. (A) Representative morphology of differentiated immature hESC-RPECs at day 14 (Size bar=100 μm). (B) Flow cytometric analysis of PMEL17+ in day 14 hESC-RPE cell cultures generated at day 14. Representative data from triplicate experiments.

Size bar=50 µm

Figure 29:
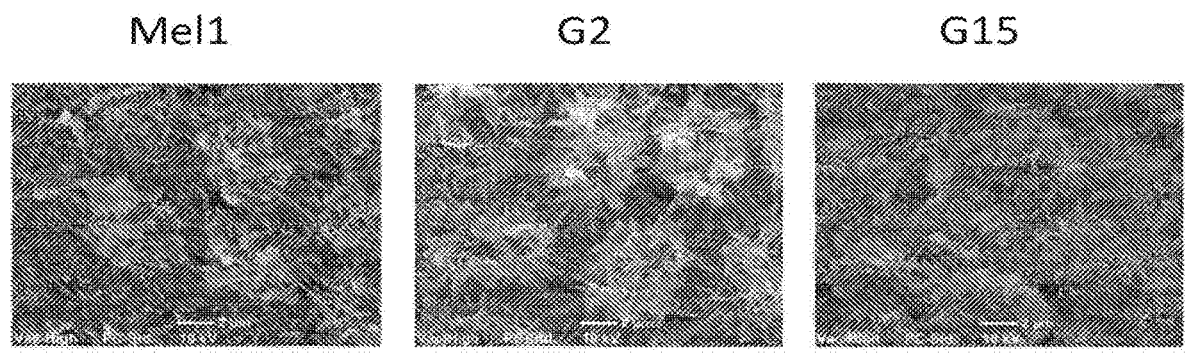

FIG. 29 Scanning electron microscopic analysis of hESC-RPECs generated under xeno-free and defined culture conditions, at passage 1, 30 days after the initiation of differentiation of hESCs to RPECs, demonstrating the appearance of maturing microvilli on the apical surface of hESC-RPECs.

Figure 30:
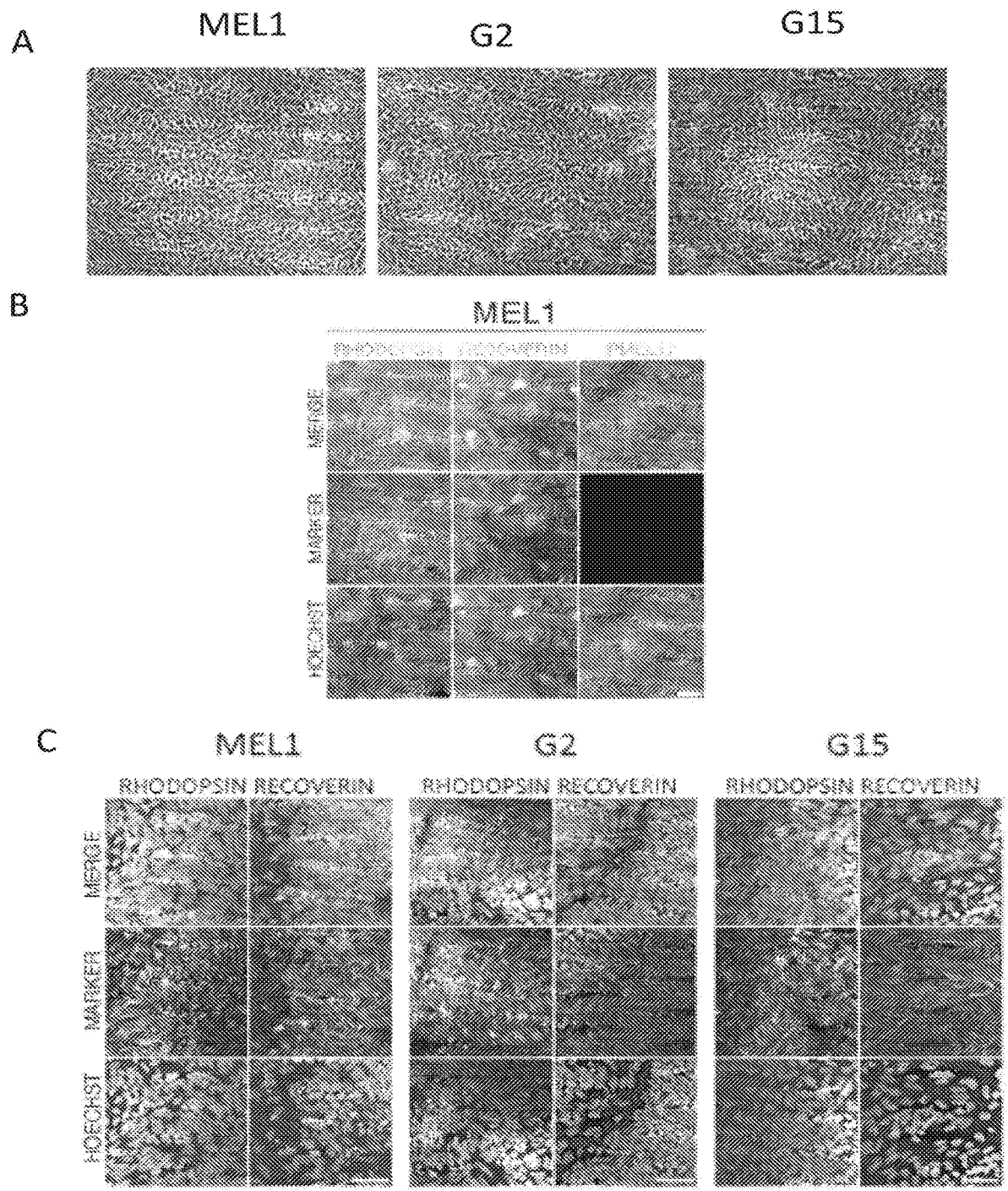

FIG. 30. (A) Morphology of hESC cultures differentiated to PhRC under xeno-free and defined conditions. Picture taken at day 21. (B) Robust expression of the photoreceptor markers (Rhodopsin and Recoverin), and the absence of the RPE marker PMel17 at day 21 demonstrates uniformity of differentiation. (C) hESC-PhRC differentiation using small molecules in a xeno-free and defined culture system shows reproducibility of across three different hESC lines (Mel1, Genea2 and Genea15). Hoechst staining of nuclei shown in dark grey to black.

Figure 31:
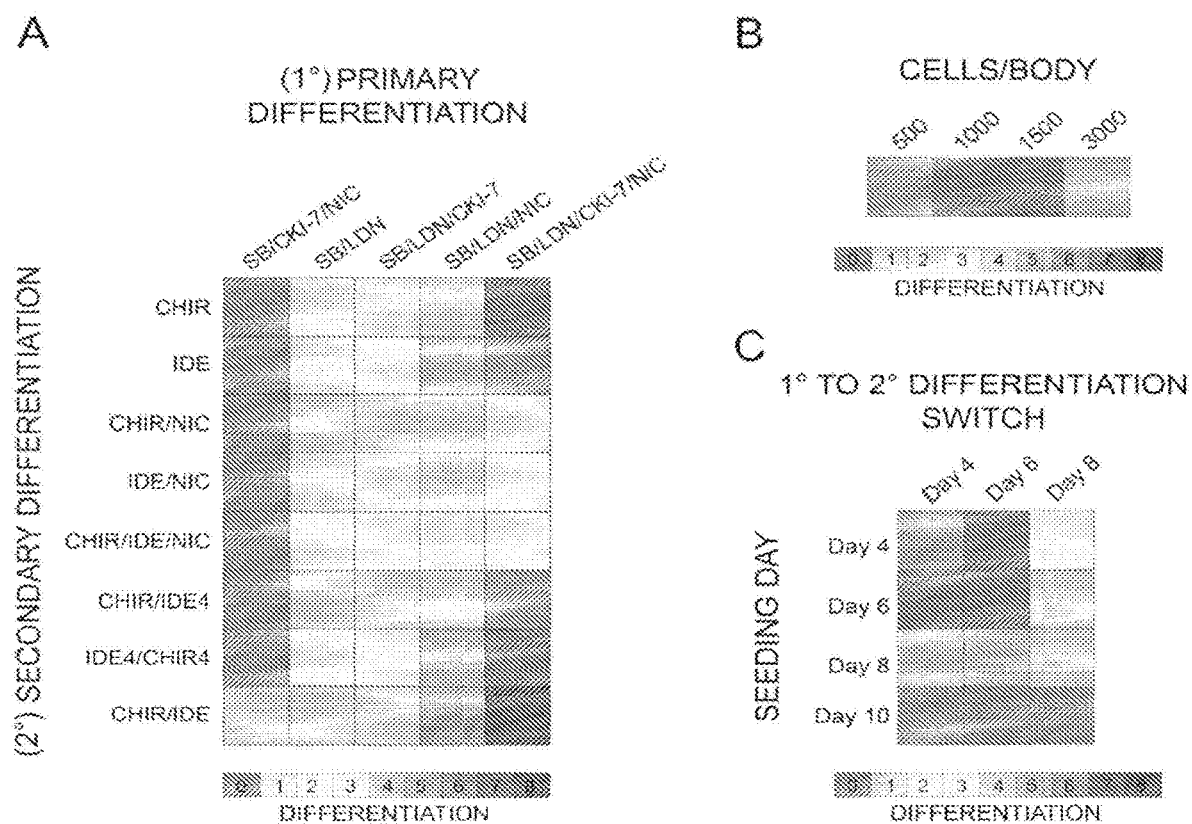

FIG. 31 Establishment of differentiation conditions for hESC-RPEC differentiation using small molecules. (A): Differentiation assay for small molecule differentiation of Mel1 hESC to hESC-RPEC. Identification of primary differentiation conditions showing that dual-smad inhibition (SB/LDN), plus enhanced with nicotinamide (NIC) result in modest differentiation levels, however, this is greatly enhanced by the activity of Casein Kinase inhibition (CKI-7). Secondary differentiation conditions indicate GSK33 inhibition (CHIR) is essential for highly efficient RPEC differentiation, while Activin A-like signaling (IDE) enhances RPEC differentiation. NIC suppresses RPEC differentiation when used after day 6. (B): Optimal ANEB size determined between 1000-1500 cells/body. (C): Optimal window for both seeding ANEBs and switching to RDM is day 6. ANEBs seeded at day 10 did not produce any hESC-RPEC, regardless of timing of inductive timing. For each experiment, ANEB outgrowths were scored for % putative RPE morphology at day 14. Differentiation is represented as heat map scores (0=0%, 1=5-10%, 2=10-15%, 3=15-25%, 5=25-40%, 6=40-55%, 7=55-70%, 8=80+%).

DETAILED DESCRIPTION

The inventor has found a method for the generation of retinal cells and in particular, eyefield progenitor cells (EFPCs), retinal pigmented epithelial cells (RPEs), photoreceptor (PhR) precursor cells, and photoreceptor (PhR) cells that are derived from stem cells, and which are useful for implantation of the generated cells into the retina to treat retinal diseases, disorders and conditions. The invention is predicated on the discovery that specific chemical substitutes, when used in a particular combination, sequence, and timing, are capable of performing the equivalent functions, and that are similar to or mimic, the natural signals that are required to differentiate stem cells into RPECs or PhR cells during normal mammalian development. In addition, the inventor has identified that the specific concentrations of these chemical substitutes are required to quickly and efficiently produce mature, functional RPECs or PhRs from pluripotent stem cells. Further, the invention has developed methods for maturation of hSC-RPECs that enhance and hasten their maturation. Finally, the differentiation able to achieve differentiation efficiencies.

Advantages of the Invented Method

Although not limited by the following example, some of the advantages of the invented method are as follow:
a. the initial cell cultures are of mammalian origin (including, but not limited to human, primate and rodents);
b. the initial cell cultures comprise cells that are stem cells;
c. the methods may be performed in their entirety under chemically defined and xeno-free culture conditions;
d. the cells are directed to differentiate to RPE cells along a series of defined cell states; including, for example, eyefield progenitor cells;
e. the RPE cells produced by the invention can be directed in an enhanced way to a mature phenotype using a chemically defined medium, with or without small molecules and or cytokines;
f. the cells are directed to differentiate to neural retinal cell derivatives, such as photoreceptor cell, along a series of defined cell states; including, for example, eyefield progenitor cells, and photoreceptor progenitor cells;
g. the differentiation methods may or may not include a process of floating cell aggregates;
h. the methods are compatible with various chemical agonists and antagonists;
i. the methods are compatible with, but do not require, the use of exogenous cytokines, or biological factors;
j. the methods are compatible with, but do not require, the use of defined, cGMP certified compliant cell culture media;
k. the methods are compatible with, but do not require, the use of defined, cGMP compliant-certified, surface substrata;
l. the methods are compatible with, but do not require, that the cell culture surface may be coated with compatible defined, cGMP compliant-certified, proteins for the differentiation, isolation, expansion and maturation of various cells types, at various stages of differentiation;
m. the methods produce a highly pure cultures of cell types, including terminally differentiated RPE cells and photoreceptor cells, as well as important cell intermediates, such as eyefield progenitor cells, neural retinal progenitor cells and photoreceptor progenitors;
n. The various cell types may be implanted into the retina, or sub-retinal space, in a subject's eye, for example patients with retinal diseases, disorders and conditions, and also into animal models of retinal diseases, disorders and conditions.

In relation to n. above, it is noted that the retinal diseases, disorders, and conditions can be associated with death, dysfunction, dystrophy, injury, loss, dedifferentiation, or migration of retinal cell derivatives, such as cells of the RPE monolayer layer, rod and cone photoreceptors, bipolar cells, amacrine cells, retinal ganglion cells, muller cells and horizontal cells.

In further relation to n. above, it is noted that the retinal diseases, disorders, and conditions may occur in the macula region of the retina. Non-limiting examples of these may include geographic atrophy, dry age-related macular degeneration (dry-AMD), wet-AMD, hereditary macular degenerations, including Best disease (the early onset form of vitelliform macular dystrophy), and macular dystrophies such as Stargardt's and Stargardt's-like disease.

In further relation to n. above, it is noted that the retinal diseases, disorders, and conditions may occur in the non-macula, or peripheral, region of the retina. Non-limiting examples of these may include various forms of retinitis pigmentosa.

Millions of people suffer from retinal diseases, disorders and conditions around the world that relate to dysfunction, injury, or loss of retinal pigment epithelium (RPE), which can subsequently result in loss of PhR function and degeneration. A potential treatment for such diseases is the transplantation of RPEs into the retina of those affected. Thus, there is a strong need to replace the impaired or lost RPE cells with healthy RPE cells. Due to the sensitive balance and interdependence of the RPE and the cells of the neural retina, death, dysfunction, dystrophy or injury of the RPE often leads to the dysfunction or degeneration of neural retinal cells. In other cases, death, dysfunction, or degeneration neural retinal cells may lead to dysfunction or degeneration of the RPE cell. Thus, there is also a strong need to replace cells of the neural retina, and in particular, the photoreceptors.

Due to the sheer number of people affected by retinal disease and dysfunction, there is a significant need to generate retinal cell derivatives (such as RPECs and photoreceptors) for cell transplantation therapies. However, to overcome, or minimise, rejection of transplanted retinal cells in patients, retinal cells should ideally be derived from HLA-matched lines that are either a), pluripotent stem cells (such as hESCs or hIPSCs), b) multipotent stem cells (for example, neural stem cells, mesenchymal stem cells, adipose-derived stem cells or retinal stem cells), c) patient-specific hIPSCs, or d) patient-specific multipotent stem cells. Further, differentiation methods that can generate eyefield progenitor cells and derivatives thereof, including RPE cells, neural retinal progenitors, and derivatives thereof, such as photoreceptor progenitor cells, and photoreceptors, from human stem cells, and do so in a rapid, efficient and clinically applicable manner, would make important contributions to the field, and generate cells which could be used for the treatment of a range of retinal diseases, disorders and conditions.

Thus, there is a strong need to have an efficient, rapid and clinically applicable method to generate eyefield progenitor cells and their derivatives, including, but not limited to, RPE cells, and cells of the neural retinal lineage, such as neural retinal precursor cells, and their derivatives (e.g., photoreceptors, glial cells etc.), such as from human stem cells that can be used for the treatment of a range of retinal diseases, disorders and conditions. A potential treatment for such diseases is the transplantation of RPECs or PhRs into the retina of those affected.

General Characteristics of the Invented Method

The method is highly efficient and rapid, requiring small molecules only, and does not require exogenous growth factors for differentiation or for maturation. Preferred embodiments of this method have been targeted towards compatibility with transplantation into humans and is suitable for use in human clinical trials and transplantation into humans and other animals. Some of these embodiments are as follow:

Methods for Producing Eyefield Progenitor Cells (EFPCs)

The inventor has found an in vitro method for the rapid and efficient production of mammalian EFPCs, under defined and xeno-free culture conditions, and using small molecules only. A distinct advantage of the methods of the invention includes the capability of rapidly generating EFPCs cells that may be further differentiated to retinal cell derivatives (e.g., RPECs and PhRCs etc.), again, under defined and xeno-free culture conditions, under that may be used for transplantation into the eye of a subject that for transplantation.

In one embodiment of the invention, SCs, such as PSCs, are cultured and maintained in an undifferentiated state under serum-free and feeder-free culture conditions, so as to produce a substantially pure and undifferentiated culture of PSCs. The resultant PSCs are subsequently cultured under feeder-free conditions in primary differentiation medium, containing at an inhibitor of BMP signalling, plus at least one or more inhibitor of TGF-β and WNT signalling, so as to differentiate PSCs to EFPCs.

In one embodiment of the invention, PSCs are cultured in a pluripotent stem cell culture medium, such as mTeSR™1, on Matrigel™, using standard colony passage culture technique. In a preferred embodiment, the PSC cultures are exposed to the Rho Kinase Inhibitor (iRock) in mTeSR™ for at least 30 minutes prior to being single cell dissociated and re-plated onto a culture surface coated with Reduced Growth Factor Matrigel™, in mTeSR™ containing iRock. PSCs may be seeded at a density, such that they are capable of reliably producing undifferentiated cultures of at least 60%-100% confluence, preferably about 85% confluence, by the onset of differentiation (day 0). In one embodiment, a preferred PSC seeding density is about 150,000 cells/cm2. At day 0, primary differentiation to EFPCs is initiated by the removal of mTeSR™1 medium, and replacing culturing the cells in primary differentiation medium, containing inhibitors of TGF-β, BMP and WNT signalling. In another preferred embodiment, the primary differentiation medium also contains nicotinamide, in addition to those mentioned.

In a preferred embodiment of the invention, PSCs are cultured under feeder-free, defined, xeno-free, and preferably cGMP-certified culture conditions, comprising a pluripotent stem cell culture medium, such as mTeSR™2, or cGMP mTeSR™1, and a culture plate coated with a xeno-free substrate, and preferably cGMP-certified substrate, such as LN521, using either standard colony passage culture technique, or single cell passage. Further, in accordance with the continuity of a xeno-free and defined method for PCS culture, PSCs are passaged as colonies using a cGMP certified reagent, such as ReLeSR™, or dissociate single cells in the absence of biological enzymes, such as Trypsin, and instead dissociated using TrypLE™ Select CTS™. In a further preferred embodiment, the PCSs are seeded on to a defined, xeno-free, and preferably cGMP-certified, substrate as single cells at a density between 100,000 to 200,000 cells/cm2.

Methods for Producing Retinal Pigmented Epithelial Cells (RPECs)

The inventor has found an in vitro method for the rapid and efficient production of mammalian EFPCs, under defined and xeno-free culture conditions, and using small molecules only. A distinct advantage of the methods of the invention includes the capability of rapidly generating EFPCs cells that may be further differentiated to retinal cell derivatives (e.g., RPECs and PhRCs etc.), again, under defined and xeno-free culture conditions, under that may be used for transplantation into the eye of a subject that for transplantation.

Methods for Producing Photoreceptors Cells (PhRCs)

The inventor has found an in vitro method for the rapid and efficient production of mammalian EFPCs, under defined and xeno-free culture conditions, and using small molecules only. A distinct advantage of the methods of the invention includes the capability of rapidly generating EFPCs cells that are have the differentiation potential to form cells of both the RPE and the neural retinal lineage, and thus can be further differentiated to retinal cell derivatives (e.g., RPECs and PhRCs etc.), again, under defined and xeno-free culture conditions, under that may be used for transplantation into the eye of a subject that for transplantation.

Summary of Differentiation Protocols of the Invented Method

A summary of differentiation protocols in the field shows that although human stem cells can be differentiated to RPECs, the methods used to differentiate them have at least one of the following weaknesses:
  a. In order to avoid the use of exogenous growth factors or cytokines, differentiation of hPSCs is initiated by withdrawal of removal of bFGF, which leads to spontaneous differentiation of hPSCs. However, this differentiation is non-directed, and results in the highly inefficient hPSC-RPEC differentiation, and requires significant enrichment steps over extended periods of time;
  b. Some methods use only small molecules, and do not use any exogenous cytokines or exogenous growth factors, however, these are inefficient and slow, taking several months to produce RPE cells, rather than a few weeks.
  c. Other methods result in efficient RPE cell differentiation, and use small molecules, but require the use of exogenous growth factors, such as Activin A, IGF-1 or bFGF to achieve rapid and efficient RPEC differentiation, and use medium culture systems that are not defines, or xeno-free;
  d. Other methods also use small molecules, in the absence of any exogenous cytokines or exogenous growth factors, however, and these are moderately efficient and relatively slow, generating 45-60% Pmel17+ cells, and requires further passage, enrichment and over two months to generate a monolayer of hPSC-RPECs. Further, this method offers little control over the transient, sequential cell intermediates, and their alternative cell fates, such as those of the neural retinal lineage.
  e. Yet, other methods for differentiation of hPSC to retinal cell derivatives use small molecules, and not cytokines or growth factors, for efficient differentiation to a retinal stem cell, these cells are not differentiated under xeno-free conditions, methods are not xeno-free, as the hPSCs are cultured and differentiated on basement membranes extracted from murine Engelbreth-Holm-Swarm (EHS) tumors. Also their subsequent differentiation to RPE cells relies on the use of the cytokine Activin A, and is not described as efficient.
  f. Finally, in another method for the generation of hPSC-RPECs, the differentiation culture is conducted in a completely xeno-free culture system, but relies on highly inefficient spontaneous differentiation of hPSCs, followed significant enrichment steps over extended periods of time;

The advantages of the invention are:
  a. Xeno-free, rapid, efficient, and robust differentiation of human stem cells to eyefield progenitor cells (>90%, 3-6 days);
  b. Xeno-free, rapid, efficient, and robust differentiation of human stem cells to immature retinal pigmented epithelial cells (>90%, 8-16 days);
  c. Xeno-free, highly pure, mature SC-RPE monolayers cells within 30-45 days; d. Xeno-free, rapid, efficient, and robust differentiation of human stem cells to photoreceptor precursor cells (>80%, 8-12 days);
  e. Xeno-free, rapid, efficient, and robust differentiation of human stem cells to photoreceptors (>80%, 18-24 days);
  f. The ability to modify differentiation such that it can be adapted to generate retinal cell derivatives, such as ganglion cells etc.
  g. Rapid, efficient, and robust differentiation of human stem cells to eyefield progenitor cells differentiated to eyefield progenitor cells, and subsequently RPE cells, neural retinal progenitors, and their derivatives (e.g., photoreceptors);
  h. It is performed in the absence of exogenous growth factors, using small molecules only;
  i. They have been developed under defined conditions, xeno-free conditions, and/or cGMP compatible conditions;
  j. Production of highly pure eyefield progenitor cells (>90%) within 4 to 6 days;
  k. Rapid and efficient production of highly pure (>90%) SC-RPE cells within 8-16 days;
  l. Rapid and efficient production highly pure mature SC-RPE monolayers cells within 30-45 days;
  m. Rapid and efficient production of highly pure SC-PhR Precursor cells (>80%) within 8-12 days;
  n. Rapid and efficient production of highly pure SC-PhR cells C80%) by within 18-24 days;
  o. They are compatible with various xeno-free or cGMP certified components in preparation for transplantation into a subject; and
  p. They can be altered to maximise use as a platform.

The invention is partly predicated on modelling of the endogenous sequence of signals required to differentiate pluripotent stem cells towards the eye field lineage, followed by retinal cell derivatives, in a stage-wise manner, to mature retinal cells such as RPE and PhR cells.

Further, 56 different combinations of various molecules were screened. Complex analysis was undertaken to identify the combination of small molecules that generated the highest percentage of early RPE cells. This was confirmed and refined through a unique series of subsequent experiments. For ease of explanation, the method can be broken down into several stages.
  i. Primary Differentiation or Eye Field Progenitor Cell Differentiation: The initial differentiation of hSCs from an undifferentiated state to a cell type that shares important molecular and functional characteristics anterior neural ectodermal state that is responsive to further differentiation towards cells that represent the eye field, called eyefield progenitor cells (EFPCs).
  ii. Neural Retinal Progentitor Cell Specification: In one instance, the invention discloses the differentiation of PSCs to highly pure cultures of EFPCs. EFPCs have the developmental competence to differentiate along two distinct developmental pathways to become neural retinal cells, and their derivatives (e.g. photoreceptors, Miller cells etc.), or to become RPE cells, or allowed to spontaneously differentiate to retinal cell derivatives in 3D organoids. In one instance, the invention discloses the differentiation of EFPCs to photoreceptor by promoting NRC differentiation, at the expense of RPEC differentiation.
  iii. Photoreceptor Cell Specification: In one instance, the invention discloses the differentiation of EFPCs to photoreceptor progenitor cells, or photoreceptor cells by promoting differentiation toward that lineage, and resulting in a population of cells that express known markers of photoreceptor progenitor cells, such as CRX, of photoreceptors, such as Rhodopsin, or Recoverin.
  iv. RPE Cell Differentiation: In one instance, the invention discloses the differentiation of EFPCs to RPE cells by promoting RPE cell differentiation, and limiting neural retinal progenitor differentiation.

v. RPE Cell Expansion: RPE cells are cultured as substantially pure populations using standard methods that are known in the art. These cells can then be expanded using combinations of culture methods and molecules, and purified to about 100% of RPE cells. It is estimated that the expansion potential of the cells is more than 15 population doublings, and may be more than 40 population doublings.

vi. RPE Cell Maturation: RPE cells can be matured (i.e. have the following characteristics: polygonal, pigmented, microvilli) at any point after they have appeared in culture (e.g. Day 10-14) under several conditions by:
a. Culturing cells in a medium which has been selected, or developed, for its ability to promote hSC-RPECs to develop a mature phenotype in preference to, for example, promoting cell number expansion.
b. Addition of small molecules, which enhance the maturation of hSC-RPECs to the base media.
c. Changing the surface substrate to one preferred by the cells for maturation.

vii. Retinal Organoid Culture: In a further instance, the invention discloses the differentiation of EFPCs to floating cell aggregates that undergo spontaneous differentiation to different tissue types of the RPE and neural retinal lineage.

There are many possible embodiments of these methods which can be broadly categorised into two major classes of strategies for applying the method, each of which have at least two major sub-classes. These classes are summarised in the diagram below:

| AGGREGATE | vs | ADHERENT |
|---|---|---|
| ANEB vs EB | | Single Cell vs Colony |
| | Enrichment & Expansion | |
| | Maturation | |

2D Versus 3D Culture

With respect to RPE cell differentiation, in each embodiment, the combination, sequence, timing and concentration of the small molecules factors used for differentiation are largely similar, however, the physical manipulation of cells differs. Timing of these physical cell manipulations is also variable, depending on the method but fall within the parameters outlined in the examples. In general terms, there are two fundamental forms of differentiation: Floating Aggregate (3D) and Adherent (2D) differentiation.

Figure 4:
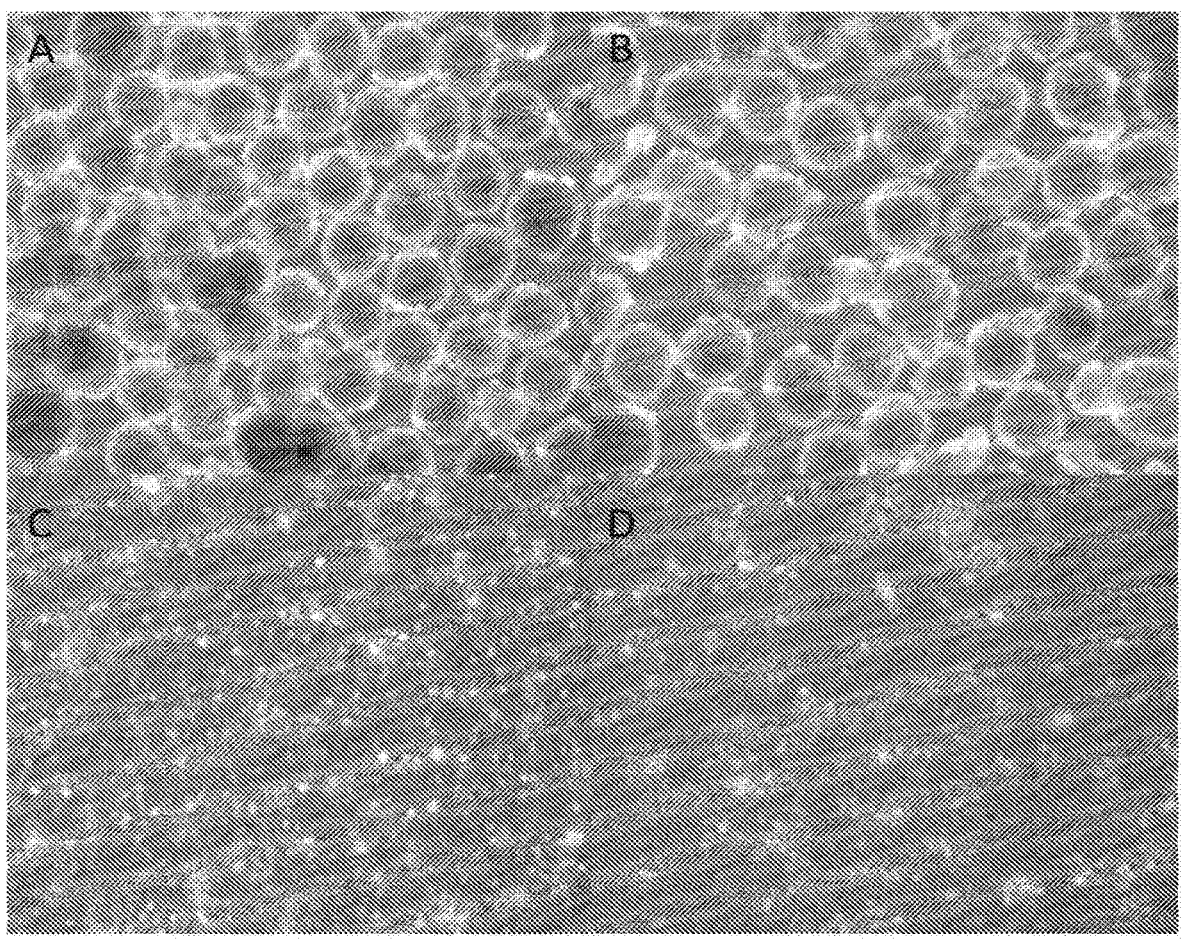
FIG. 4 Illustrates the morphology of several embodiments of hESC differentiation during differentiation to the anterior neural ectodermal cells or eyefield progenitor cells (EFPCs) cultures, 4 days after the initiation of differentiation in primary differentiation conditions. (A) Morphology of EFPC-derived cell aggregate (3D) (ANEBs) suspension culture. (B) Morphology of hESC-derived cell aggregates (3D) (EBs) in suspension culture. (C) Morphology of single cell-seeded hESC adherent monolayer (2D) differentiation cultures. (D) Morphology of hESC colony adherent monolayer (2D) differentiation cultures.

Adherent (2D) differentiation involves culturing the cells on a surface or surfaces throughout the differentiation process, and can be further subdivided based on how the cells are treated prior to, during, and after, initiation of differentiation. In general, hESCs can be seeded as single cells, or as colonies, before initiation of differentiation (FIG. 4 A-D). Upon differentiation, hESC-RPE cells can be cultured using common methods and reagents, and may subsequently be matured.

Floating aggregate (3D) differentiation involves the formation of floating cell aggregates from either EFPCs or undifferentiated hESCs that are cultured in suspension for a limited period of time before being further cultured and differentiated in an adherent format, on an appropriate surface substrate, under the appropriate cell culture medium and small molecule signalling conditions.

Specifics of Differentiation Protocols of the Invented Method
Cell Types

With respect to the application of the invention, in full, part or in an obvious and altered form, the cells that may be compatible with the invention do not necessary need to have embryonic-like pluripotency (such as embryonic stem cells and induced pluripotent stem cells), but may share important similarities to the cell types that naturally occur in a stage-wise sequence during the development of the mammalian morula, through to the fully developed offspring. Naturally occurring cells that are of particular relevance and usefulness to the invention are the cells types that occur in, or can be isolated from, a) the blastocyst, specifically the pluripotent cells of the inner cell mass, or equivalent, b) the pre-gastrulation primitive ectoderm, c) the post-gastrulation neural ectoderm, d) the anterior neural ectoderm, or the anterior neural plate, e) the sub-set of cells in the diencephalon that give rise to the eyefield, f) the eyefield, g) the optic cup, h) RPE progenitor cells, i) neural retina progenitors, and j) photoreceptor progenitors, or in vitro derived cells that are the equivalent to the naturally occurring populations (stated in a-j).

Developmental Competence

The fundamental principle of cell differentiation that makes the cells identified above applicable to the invention is the principle of developmental competence, whereby a cell in a particular state will respond to a particular signal, or set of signals, to differentiate in a manner that is consistent with their embryological or developmental program. This means that two cell types, derived using different means, or from different contexts (for example, hESCs from the human blastocyst, and hIPSCs generated via reprogramming of fibroblast cells) may be considered equivalent to one another if they both respond to a signalling environment in a similar way, by following the same, or similar differentiation program. An example of this equivalence in developmental competence between two cell types that is well understood by those with knowledge in the art of stem cell biology, is the differentiation of hPSCs to neural ectoderm cells. In this example, undifferentiated hESCs and hIPSCs are exposed to substances that inhibit TGF-β and BMP signalling, will result in both pluripotent cells types differentiating to neural ectodermal cells, despite the fact that they have very different origins. Further, the resultant cells can be subsequently differentiated to derivatives of the neural ectodermal lineage, by using the same signalling strategies on both cells types to achieve similar cellular responses and differentiation outcomes.

Equivalence and Developmental Competence

The ability to generate cells that represent in vitro equivalent cells of mammalian tissue (be that cells present during development, or after birth), by either, i) their harvest and isolation for these tissues, and in vitro culture to achieve, or maintain their cell state, ii) their generation in vitro from more primitive cells that have the developmental competence to be differentiated into them, or iii) their generation in vitro using widely practiced methods of reprogramming, direct reprogramming, de-differentiation, as well as other forms of cell manipulation, that are commonly used to make a cells i) less committed, more naïve, or with an increased differentiation potential or ii) to direct them toward a call fate that is of a distantly related lineage, and one that is unlikely to occur naturally, without significant and direct manipulation (for example, the ability to turn a skin cell into a kidney cell), coupled with developmental competence and equivalence, means that there are numerous cell types, naturally occurring, or otherwise, that are able to be integrated into specific stages of the invention to generate cells of the retinal lineage.

Sources of Cells for Retinal Differentiation

With respect to the above, below are non-limiting examples of cells that can be integrated into the invention, as a result of their ability to respond to the culture conditions of the invention.

Pluripotent Stem Cells that can be Obtained, or Generated, to be Used for Differentiation to Retinal Cell Types, or Derivatives (A) Embryonic Stem Cells
1. The cells are pluripotent stem cells derived from the embryo.
2. In one embodiment, the embryo is a zygote.
3. In another embodiment, the embryo is an early, or late stage morula.
4. In another embodiment, the embryo is a blastocyst.
5. In one embodiment, the pluripotent stem cells are derived from a mammalian morula, and cultured under the appropriate conditions to establish pluripotent stem cell cultures.
6. In a preferred embodiment, the pluripotent stem cells are derived from a mammalian blastocyst, and cultured under the appropriate conditions to establish pluripotent stem cell cultures.
   a. In one embodiment, the blastocyst may be generated by fertilisation of an oocyte with spermatozoa, in vitro.
      i. In a further embodiment, the gametes (oocyte and spermatozoa) are themselves the generated by in vitro differentiation.
   b. In another embodiment, the blastocyst may be the result of somatic cell nuclear transfer of genetic material into an enucleated oocyte (SCNT).
   c. In another embodiment, the blastocyst may be the result of a triggered activation of an oocyte to become a blastocyst by parthenogenesis, whereby the activated oocyte begins the process of embryogenesis in the absence of spermatozoa, and has a haploid genome.
7. In a preferred embodiment, the mammalian species is a human.
8. In another embodiment, human embryonic stem cells (hESC) cultures are isolated and established in the absence of feeder cells, and under defined conditions.
9. In another embodiment, human embryonic stem cells (hESC) cultures are isolated and established in the absence of feeder cells, under defined conditions, and xeno-free conditions.
10. In a preferred embodiment, the hESC cultures are established from human embryonic tissue under cGMP compatible materials, methods and facilities.
11. In another embodiment, the hESC cultures are free of infection.
12. In another embodiment, the hESC cultures are chromosomally normal, and without mutations.
13. In another embodiment, the hESC cultures are cGMP certified.

(B) Induced Pluripotent Stem Cells
1. In one embodiment, the induced pluripotent stem cells (IPSCs) are generated from a mammalian cell.
2. In a preferred embodiment, the mammalian species is human.
3. In another embodiment, human hIPSC cultures are isolated and established in the absence of feeder cells, and under defined conditions.
4. In another embodiment, hIPSC cultures are isolated and established in the absence of feeder cells, under defined conditions, and xeno-free conditions.
5. In a preferred embodiment, the hIPSC cultures are established from human embryonic tissue under cGMP compatible materials, methods and facilities.
6. In another embodiment, the hIPSC cultures are free of infection.
7. In another embodiment, the hIPSC cultures are chromosomally normal, and without mutations.
8. In another embodiment, the hIPSC cultures are cGMP certified.

(C) Naïve PSCs
1. In one embodiment the pluripotent stem cells have the characteristics of naïve cell state. Naïve PSCs generally tend to exhibit several molecular and developmental characteristics for the list (C-2).
2. Non-limiting examples of the characteristics or features of naïve PSCs include:
   a. Do not require MEK-ERK signalling
   b. Do not require bFGF signalling
   c. Do not require Activin A or TGF-B signalling
   d. Preference for LIF signalling for self-renewal
   e. Use the Distal enhancer of Pou5f1
   f. Have global DNA hypomethylation
   g. Do not have X inactivation
   h. Lower levels of H3K27me3 epigenetic marks on developmental regulators
   i. Lower expression levels of the priming marker Otx2

(D) Primed PSCs
1. In one embodiment the pluripotent stem cells have the characteristics of primed pluripotent cell state. PRIMED PSCs generally tend to exhibit several molecular and developmental characteristics for the list below (D-2).
2. Non-limiting examples of the characteristics or features of primed PSCs include:
   a. MEK-ERK signalling dependence
   b. Long-term dependence on bFGF signalling
   c. Long-term dependence on Activin A or TGF-B signalling
   d. Do not require LIF signalling for self-renewal
   e. Use the proximal enhancer of Pou5f1
   f. Do not have global DNA hypomethylation
   g. Have undergone X inactivation
   h. Higher Levels of H3K27me3 epigenetic marks on developmental regulators
   i. Higher expression levels of the priming marker Otx2

Stem Cells that can be Obtained, or Generated, to be Used for Differentiation to Retinal Cell Types, or Derivatives With respect to the invention, it has been contemplated that cells that do not demonstrate the developmental potential to form at least one type cell that is derived from the eyefield, or the eyefield, may be induced to acquire properties of such cells through manipulation. Cell types that may have the developmental potential to form at least one cell type that is derived from the eyefield, may also be manipulated to acquire further properties that could make them competent to differentiate to signals provided through this invention, such that the resultant cells are derivatives of the retinal lineage, including, but not limited to RPEC, neural retinal cells, such as photoreceptors, ganglion cells, amacrine cells etc. Also, it should be noted that the RPEC in accordance with the present invention is especially suitable for regeneration of host RPE layer thereby providing improved vision following transplantation there with into a subject's retina. The photoreceptors in accordance with the present invention are especially suitable for regeneration of the host photoreceptor layer, thereby providing improved vision following transplantation into a subject's retina.

Methods of manipulation that may be used to generate cells capable of generating retinal cell derivatives include:
1. Direct reprogramming of a target cell, using delivery of transcription factors via,
   a. lentiviral delivery
   b. episomes
   c. plasmids
   d. mRNA
   e. Protein delivery
2. Small molecule inhibition of epigenetic modifying enzymes, such as:
   a. Modulators of DNA Methylation (e.g., 5-aza-cytidine)
   b. Modulators of Histone Methylation (e.g., Bix-01294)
   c. Histone Deacetylases (e.g., Valproic Acid)
3. Small molecule modulation of signalling pathways, such as:
   a. Rho Kinase (e.g., Y-27632)
   b. GSK3 (e.g., CHIR99021)
   c. TGFβ superfamily receptors (e.g., SB 431542, LDN193189, repsox, A-83-01)
   d. WNT (e.g., IWP2)
   e. Casein Kinases (e.g., CKI-7, epiblastin A)
   f. MEK (e.g., PD0325901)

In one embodiment, the manipulation of a cell to acquire characteristics of neural stem cells, anterior neural ectodermal cells, eyefield progenitor cells is by the inhibition of signalling pathways. In a further embodiment, the signalling pathways that may be manipulated include either, or both of, the two main branches of the TGFβ super family signalling pathway, comprising both TGFβ/BMP and TGFβ/Activin pathways, the WNT pathway, function of Casein Kinase, the hedgehog pathway. A further embodiment involves the small molecule inhibition of at least one or more of DNA methyltransferases, or histone methylases, or histone deacetylases. In a further embodiment, small molecule inhibition of epigenetic modifying enzymes and signaling pathways may be combined, as concurrent, or sequential factors, to generate cells that may acquire the ability to differentiate and generate retinal cell derivatives.

Cells that may be cultured in contact with said chemical manipulation may include, but are not limited to: fibroblasts, mesenchymal stem cells, adipose-derived stem cells, hematopoietic stem cells, olfactory derived stem cells etc.

In a preferred embodiment, that said cells are human.

In another preferred embodiment, the cells are isolated from a post-natal human.

In yet another embodiment, human adult stem cells are exposed to inhibitors of at least one of TGFβ/BMP, TGFβ/Activin, WNT signalling, Casein Kinases, and also at least one or more inhibitor of DNA methyltransferases, or histone methylases, or histone deacetylases, until they acquire said cell characteristics.

In a preferred embodiment, human adult stem cells are exposed to at least SB 431542, LDN193189, and at least one or more of Y-27632, epiblastin A, 5-aza-cytidine, Valproic Acid, or Bix-01294, until they acquire said cell characteristics.

Genetic and Epigenetic Status of Cells that can be Used to Study Retinal Diseases, and their Treatments With respect to the various types of cells suitable for generating retinal cell derivatives, discussed above, the following non-limiting examples illustrate the application of the invention to cells derived from individuals with retinal diseases, or created to recapitulate retinal disease to better understand their mechanisms and discover methods to treat/reverse dysfunction.

In an embodiment, the hSC cultures are generated from cells that are isolated from individuals with inherited forms of retinal diseases or retinal syndromes.
   a. In another embodiment, the retinal disease is Dry-AMD
   b. In another embodiment, the retinal disease is Wet-AMD
   c. In one embodiment, the retinal disease is Retinitis Pigmentosa
   d. In one embodiment, the retinal disease is Stargardt's Disease.
   e. In one embodiment, the retinal disease is Best Disease
   f. In one embodiment, the retinal disease is Cone-Rod Dystrophy In an embodiment, the hSC cultures are generated from cells isolated from individuals with inherited forms of retinal diseases or retinal syndromes.
   a. In another embodiment, the retinal disease is Dry-AMD
   b. In another embodiment, the retinal disease is Wet-AMD
   c. In one embodiment, the retinal disease is Retinitis Pigmentosa
   d. In one embodiment, the retinal disease is Stargardt's Disease.
   e. In one embodiment, the retinal disease is Best Disease
   f. In one embodiment, the retinal disease is Cone-Rod Dystrophy In an embodiment, the hPSC cultures are generated from cells isolated from individuals that carriers of genetic markers (such as QTL, or SNPs), or mutations that increase the lifetime risk of developing retinal diseases or retinal syndromes.

Non-limiting examples of retinal disease and retinal syndrome categories include: dry Age-related macular degeneration, wet age-related macular degeneration, autosomal recessive Bardet-Biedl syndrome, autosomal dominant Chorioretinal atrophy or degeneration, autosomal dominant Cone or cone-rod dystrophy, autosomal recessive Cone or cone-rod dystrophy, X-linked Cone or cone-rod dystrophy, autosomal dominant Congenital stationary night blindness, autosomal recessive Congenital stationary night blindness, X-linked Congenital stationary night blindness, autosomal dominant Leber congenital amaurosis, autosomal recessive Leber congenital amaurosis, autosomal dominant Macular degeneration, autosomal recessive Macular degeneration, autosomal dominant Ocular-retinal developmental disease, autosomal dominant Optic atrophy, autosomal recessive Optic atrophy, X-linked Optic atrophy, autosomal dominant Retinitis pigmentosa, autosomal recessive Retinitis pigmentosa, X-linked Retinitis pigmentosa, Syndromic/systemic diseases with retinopathy, autosomal dominant, Syndromic/systemic diseases with retinopathy, autosomal recessive, Syndromic/systemic diseases with retinopathy, X-linked, Usher syndrome, Mitochondrial linked retinopathies, X-linked retinopathies.

In another embodiment, the retinal diseases or retinal syndromes in (10), (11) and (12) may be due to one of several, or a combination of several, genetic causes.

Non-limiting examples of known genes whose mutation or misregulation causes, contributes to, or is associated with, retinal degenerative diseases and retinal syndromes include:

ABCA4, ABCC6, ABHD12, ACBD5, ADAMS, ADAMTS18, ADGRV1, ADIPOR1, AGBL5, AHI1, AIPL1, ALMS1, ARL2BP, ARL3, ARL6, ARMS2, ASRGL1, ATF6, ATXN7, BBIP1, BBS1, BBS10, BBS12, BBS2, BBS4, BBS5, BBS7, BBS9, BEST1, C12orf65, C1QTNF5, C2, C21orf2, C2orf71, C3, C8orf37, CA4, CABP4, CACNA1F, CACNA2D4, CAPN5, CC2D2A, CDH23, CDH3, CDHR1, CEP164, CEP250, CEP290, CERKL, CFB, CFH, CHM, CIB2, CLN3, CLRN1, CLUAPI, CNGA1, CNGA3, CNGB1, CNGB3, CNNM4, COL11A1, COL2A1, COL9A1, CRB1, CRX, CSPP1, CTNNA1, CYP4V2, DFNB31, DHDDS, DHX38, DMD, DRAM2, DTHD1, EFEMP1, ELOVL4, EMC1, ERCC6, EXOSC2, EYS, FAM161A, FBLN5, FLVCR1, FSCN2, FZD4, GDF6, GNAT1, GNAT2, GNB3, GNPTG, GPR125, GPR179, GRK1, GRM6, GUCA1A, GUCAIB, GUCY2D, HARS, HGSNAT, HK1, HMCN1, HMX1, HTRA1, IDH3B, IFT140, IFT172, IFT27, IMPDH1, IMPG1, IMPG2, INPP5E, INVS, IQCB 1, ITM2B, JAG1, KCNJ13, KCNV2, KIAA1549, KIF11, KIZ, KLHL7, KSS, *LAMA*1, LCA5, LHON, LRAT, LRIT3, LRP5, LZTFL1, MAK, MAPKAPK3, MERTK, MFN2, MFRP, MFSD8, MIR204, MKKS, MKS1, MT-ATP6, MT-TH, MT-TL1, MT-TP, MT-TS2, MTTP, MVK, MYO7A, NBAS, NDP, NEK2, NEUROD1, NMNAT1, NPHP1, NPHP3, NPHP4, NR2E3, NR2F1, NRL, NYX, OAT, OFD1, OPA1, OPA3, OPN1LW, OPN1MW, OPN1SW, OTX2, PANK2, PAX2, PCDH15, PCYTIA, PDE6A, PDE6B, PDE6C, PDE6G, PDE6H, PDZD7, PEX1, PEX2, PEX7, PGK1, PHYH, PITPNM3, PLA2G5, PLK4, PNPLA6, POCIB, POMGNT1, PRCD, PRDM13, PROM1, PRPF3, PRPF31, PRPF4, PRPF6, PRPF8, PRPH2, PRPS1, RAB28, RAX2, RB1, RBP3, RBP4, RCBTB1, RD3, RDH11, RDH12, RDH5, RGR, RGS9, RGS9BP, RHO, RIMS 1, RLBP1, ROM1, RP1, RP1L1, RP2, RP9, RPE65, RPGR, RPGRIP1, RPGRIP1L, RS1, RTN41P1, SAG, SDCCAG8, SEMA4A, SLC24A1, SLC25A46, SLC7A14, SNRNP200, SPATA7, SPP2, TEAD1, TIMM8A, TIMP3, TLR3, TLR4, TMEM126A, TMEM216, TMEM237, TOPORS, TREX1, TRIM32, TRNT1, TRPM1, TSPAN12, TTC8, TTLL5, TTPA, TUB, TUBGCP4, TUBGCP6, TULP1, UNC119, USHIC, USHIG, USH2A, VCAN, WDPCP, WDR19, WFS1, ZNF408, ZNF423, ZNF513.

Kits

The present invention also provides kits for containing entities for performing the methods of the present invention as described above, and for presenting or displaying a molecule, wherein the kits facilitate the employment of the methods and processes of the invention. Typically, kits for carrying out a method of the invention contain all the necessary reagents to carry out the method. Typically, the kits of the invention will comprise one or more containers, containing for example, cell culture system(s), for performing the methods thereof.

In the context of the present invention, a compartmentalised kit includes any kit in which reagents/molecules/entities are contained in separate containers, and may include small glass containers, plastic containers or strips of plastic or paper. Such containers may allow the efficient transfer of reagents/molecules/entities from one compartment to another compartment whilst avoiding cross-contamination of the samples and reagents/molecules/entities, and the addition of reagents/molecules/entities or solutions of each container from one compartment to another in a quantitative fashion.

Typically, a kit of the present invention will also include instructions for using the kit components to conduct the appropriate methods.

EXAMPLES

The following is a step-wise overview of the differentiation method that was undertaken by the inventor to support the invention. The below description should not be taken as limiting to the method of the invention. Summaries of other variations along with experimental evidence, such as a purely adherent (2D) method, and completely xeno-free method, are also given as further examples herein below, and are within the scope of the invention.

Where techniques described below refer to commonly used techniques by practitioners in the field of the invention they are simply included by the use of their common name within the field and exemplary bibliographic references provided if a particular technique is specified. All molecular and tissue culture techniques not described in detail should be performed to the standards possessed by someone in the field with the proper training, skill and competence.

The generic examples of hESC differentiation to hESC-RPEC, or hESC-PhRs, given below may be conducted under completely defined, feeder-free and/or xeno-free culture conditions, depending on requirements of the operator. The specific examples of the invention disclosed herein do not limit the scope of embodiments of the invention, particularly to those that that are not cGMP certified, or capably of attaining cGMP certification upon application. In both principle and practice, it is obvious to one trained in the art that any non-cGMP components given in examples of the invention can readily be substituted for components with cGMP certification, without negatively impacting the process, outcome, or utility of the methods of the invention.

Figure 1:
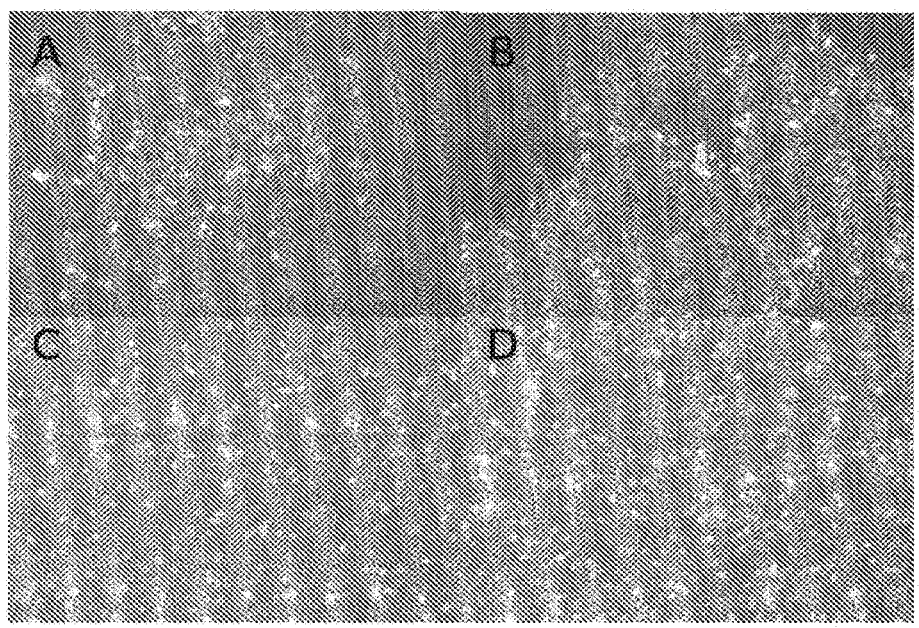
FIG. 1. (A) Image of Mel1 hESC Cultures ON MATRIGEL AND IN mTeSR MEDIUM. (B) Image of Genea 002 hESC Cultures ON MATRIGEL AND IN mTeSR MEDIUM. (C) Image of Mel1 and hESCs ON RGFMG AND IN mTeSR MEDIUM+Irock. (D) Image of Genea 002 hESC ON RGFMG AND IN mTeSR MEDIUM+iROCK FIG. 2 Illustrates the morphology of undifferentiated Mel1 hESC cultures grown under feeder-free conditions as single cell-seeded monolayers on Reduced Growth Factor Matrigel™ in mTeSR™1 medium, in the presence of iRock. (A) 24 hrs post-seeding as single cells, at approximately 15% confluence. (B) 48 hrs post-seeding as single cells, at approximately 40% confluence. (C) 72 hrs post-seeding as single cells, at about 90% confluence.

HESC Culture hESCs were cultured under feeder-free conditions, on tissue plates pre-coated with hESC-qualified Matrigel (Corning) in mTeSR™-1 (StemCell Technologies, Vancouver, BC, Canada) medium, and passaged weekly with type IV collagenase (1 mg/ml; Gibco), and plated onto a cell culture dish freshly pre-coated with hESC-qualified Matrigel (FIG. 1—A & B).

hESCs were cultured under defined, feeder-free and xeno-free culture conditions, on tissue plates pre-coated with either Vitronectin XF (StemCell Technologies), or human recombinant LN521 (hrLN521) (Life Technologies), in complete mTeSR™2 medium, and passaged weekly with RLeSR™ (StemCell Technologies) and plated onto a cell culture dish freshly pre-coated with either Vitronectin XF™, or hrLN521.

A Generic Description Differentiation of hESCs to RPECs

Figure 2:
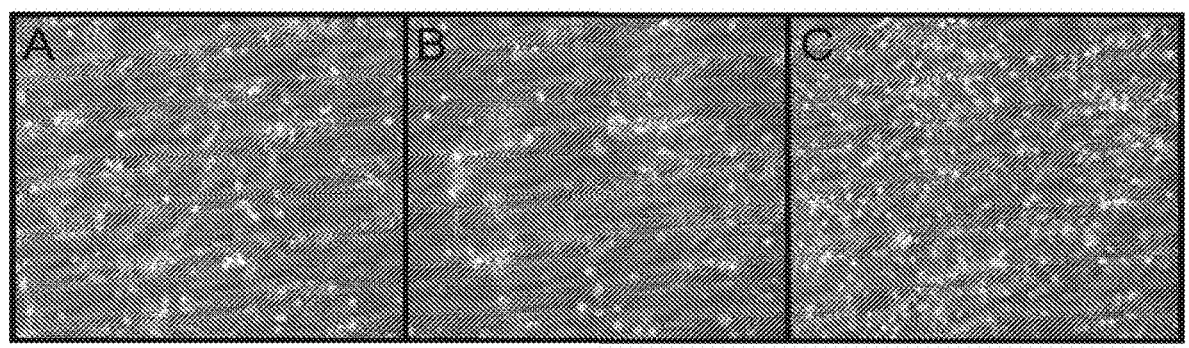
Figure 3:
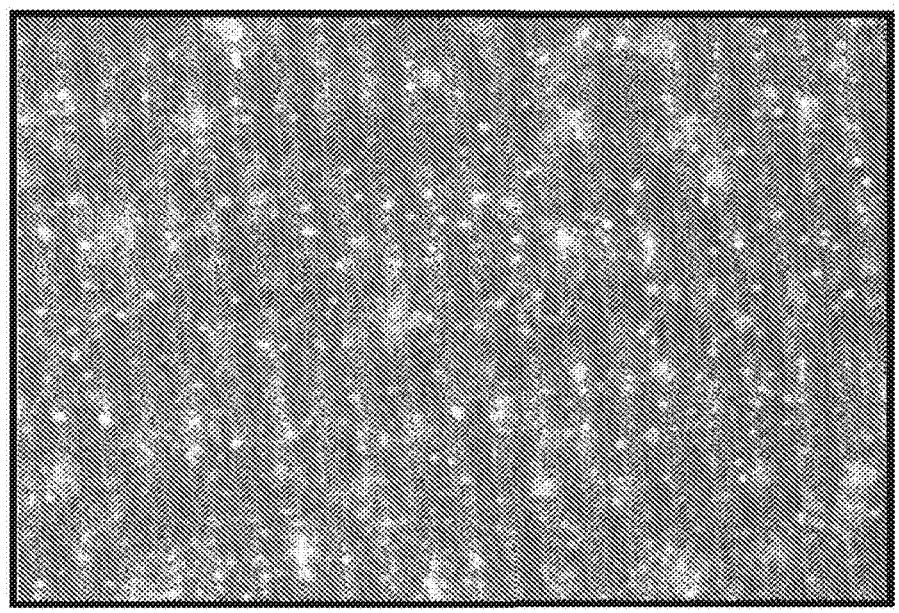
FIG. 3 Illustrates the morphology of Mel1 hESC cultures, (A) 48 hours after the initiation of differentiation in primary differentiation culture medium, on Reduced Growth Factor Matrigel™, (B) after single cell dissociation and generation of cell aggregates (ANEBs) of approximately 1500 cells/ANEB, using the AggreWell™400 (StemCell Technologies, VA, Canada) system, under primary differentiation conditions, in the presence of iRock.
Figure 3:
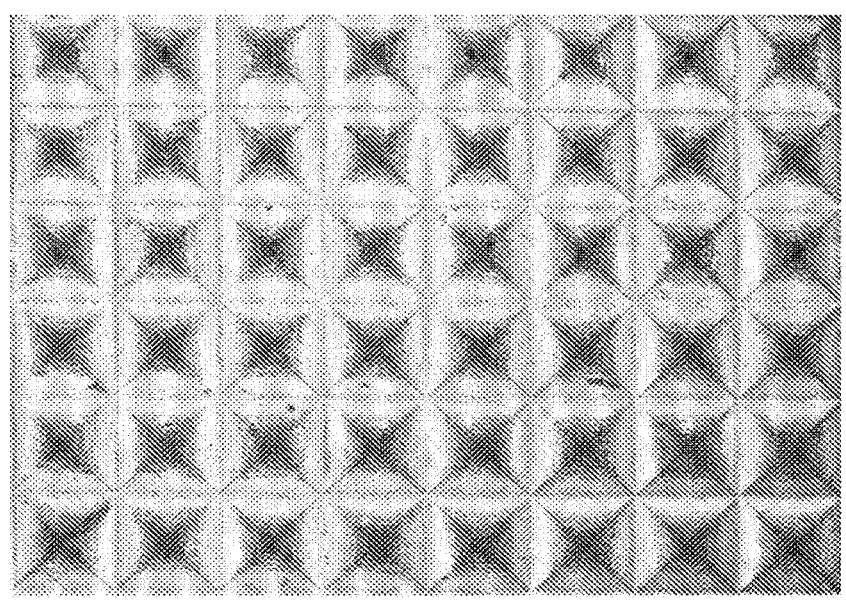
Figure 5:
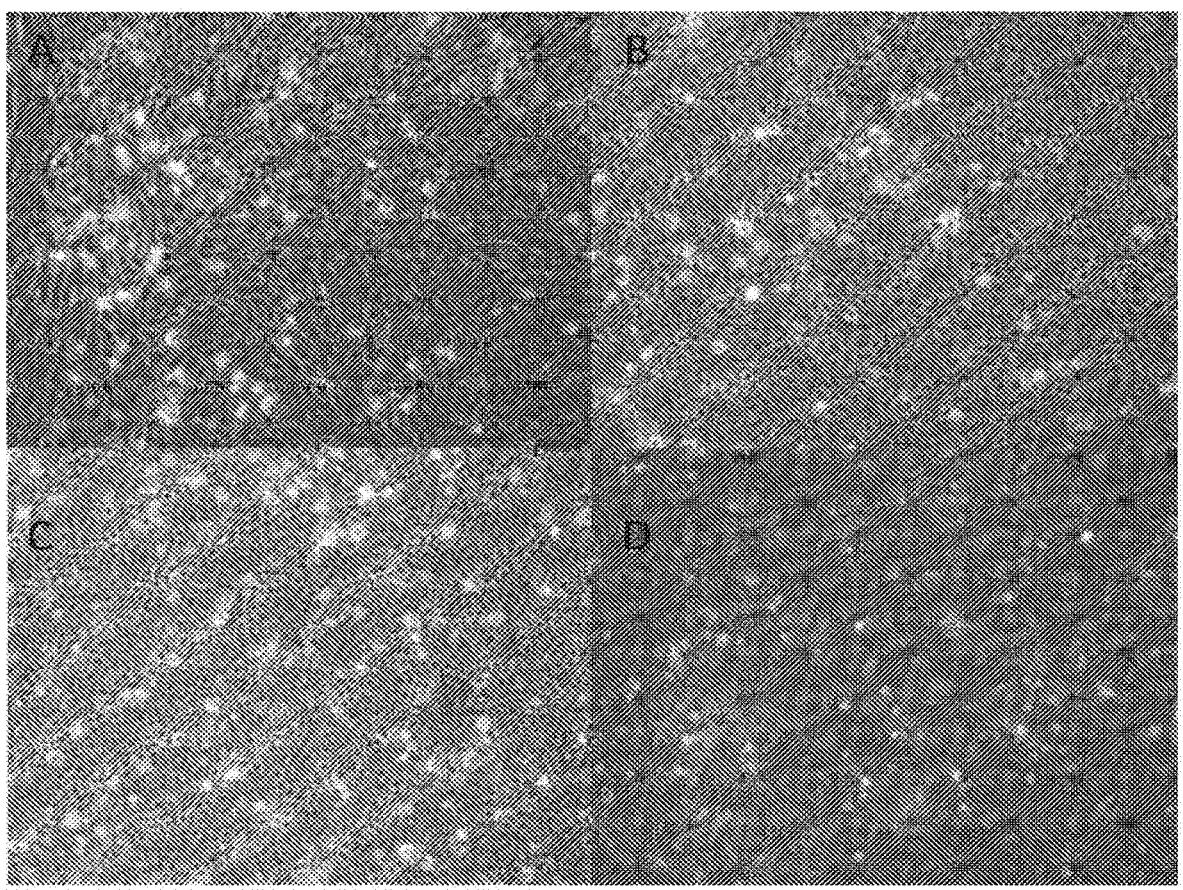
FIG. 5, (A) Illustration of the appearance of hESC-RPECs at day 14 of the ANEB differentiation format. ANEBs were seeded at day 6 onto Vitronectin XFT (StemCell Technologies) in RPE Differentiation Medium. Outgrowths of ANEBs seeded at D6 on Vitronectin XF™ after 6 days in primary differentiation condition, and switched to secondary conditions for a subsequent 8 days. (B) Appearance of hESC-RPECs via EB differentiation at day 14. Seeded EB outgrowths on GFRMG, showing high proportion of hESC-RPECs in the outgrowths EBs seeded at D6 on GFRMG after 6 days in primary differentiation condition, and switched to RPE differentiation conditions for a subsequent 8 days. (C) Appearance of hESC-RPE via single cell dissociation and adherent differentiation (D8-D14). Single cell dissociated hESCs were differentiated in primary differentiation conditions form days 0-6, and changed to secondary media after day 6. Cells were single cell dissociated on D2 & D6 on and reseeded on GFRMG at ~25-40% confluence showing high proportion of hSC-RPEs at day 9. (D) Appearance of hESC-RPECs via direct colony differentiation of hESCs (D14) Appearance of hESC-RPECs from hESC colonies directed to RPECs on GFRMG, showing high proportion of hESC-RPECs. Briefly, hESC colonies were seeded on GFRMG in mTeSR and expanded until confluent. Media was then changed to primary differentiation media from D0-D05, and changed to secondary differentiation media from D6-D14.
Figure 8:
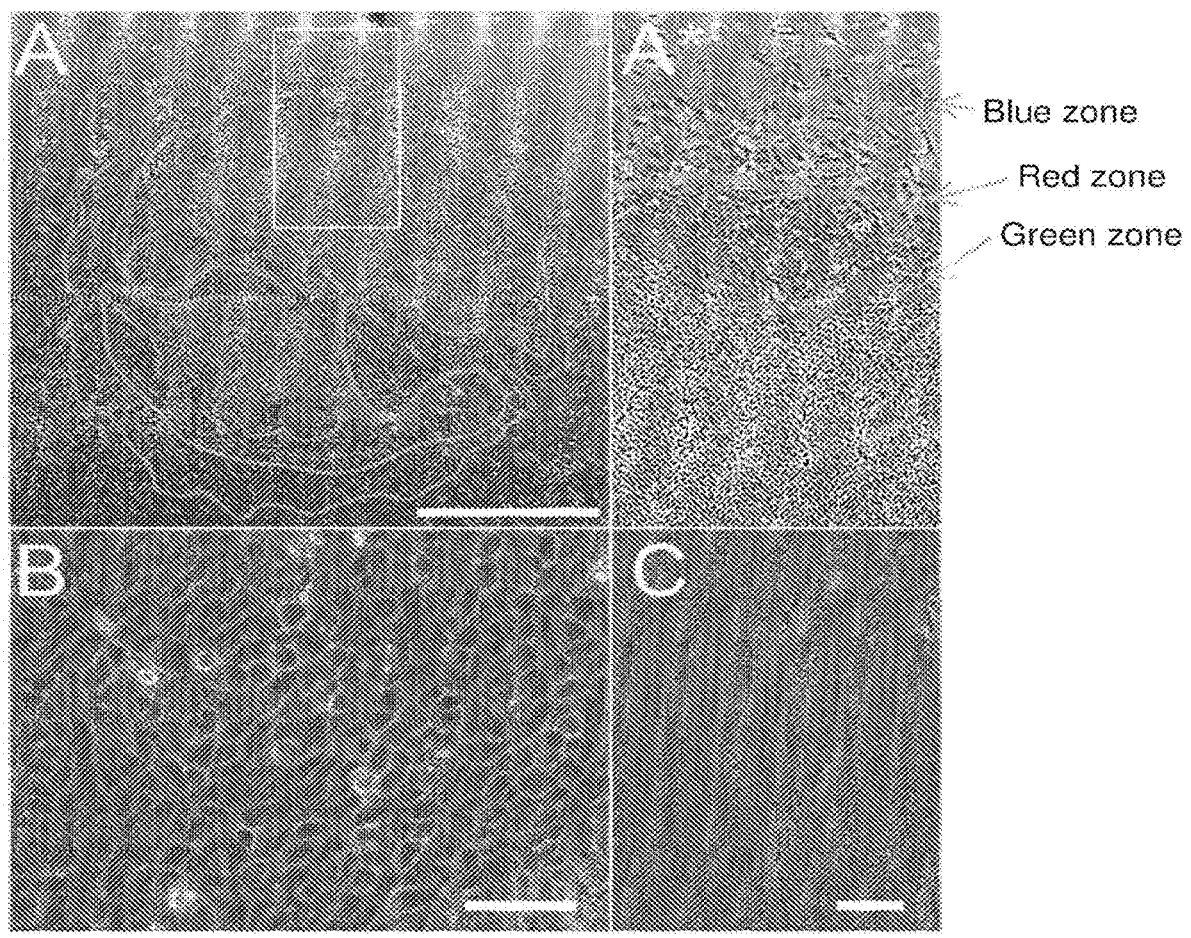
FIG. 8 ANEB outgrowth at day 16. (A) Typical morphology of ANEB outgrowths at day 16. First, central zone—containing tightly packed putative hESC-RPECs. Central band—moderately-packed hESC-RPECs. Outer band—differentiating hESC-RPE cells on the front of the expanding edge of the ANEB outgrowths with fibroblast-like morphology. Size bar=1000 μm. (B) Morphology of densely packed putative hESC-RPEC. Size bar=50 mm. (C) SEM of day 14 putative hESC-RPEC showing flat morphology and no visible microvilli. Size bar=2 μm.
Figure 9:
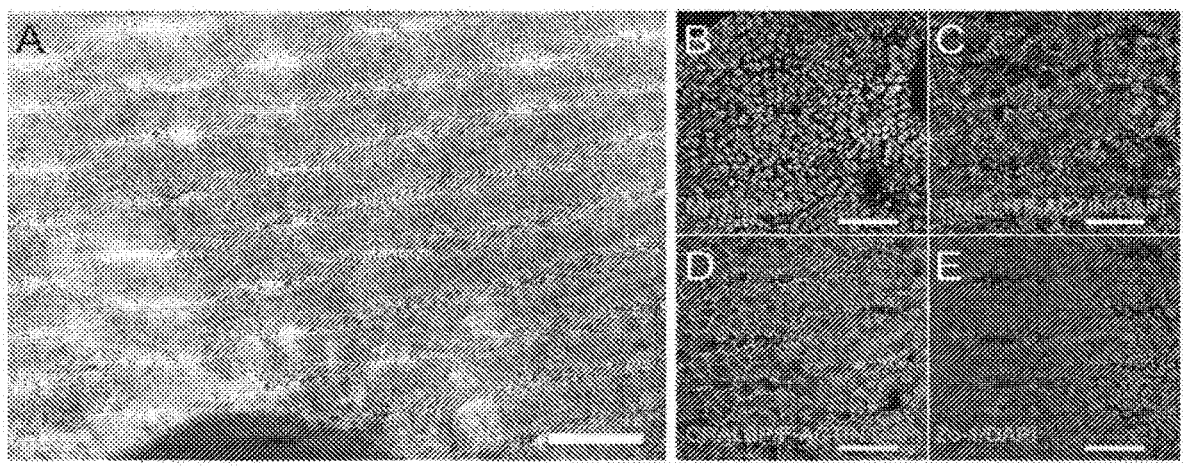
FIG. 9 Analysis of hESC-RPE cells after small molecule differentiation of hESC to hESC-RPE cells via ANEB differentiation, and continued culture until day 28, without re-plating. (A) ANEB outgrowth showing RPEC-like morphology—tight epithelial monolayer formation and pigmentation. Size bar=200 μm. (B) Detection of the RPE marker MITF by immunoflourescence at day 28. (C) Detection of the RPE marker PMel17 by immunoflourescence, and f-actin by phalloidin staining, at day 28. (D) Detection of the mature RPE marker CRALBP by immunoflourescence, and f-actin by phalloidin staining, indicating partial co-localisation to the membrane and the establishment of the visual cycle components by 10 day 28. € Diffuse Zo-1 localisation in the cytoplasm and at the membrane indicting early formation of tight junctions. Dapi staining for all nuclei (B-E).

HESC differentiation to eyefield progenitor cells is performed in a suitable basal medium (e.g., Basal medium 1), supplemented with LDN, and at least one of SB and CKI-7, and optionally one or more of NIC, Pur and IWP for 4-8 days. EFPCs are further directed to an RPE cell fate in the by culture in a suitable basal medium and a cell density that is permissible for RPEC differentiation (e.g., 5,000-80,000 cells/cm2) in RPE differentiation medium, containing at least one of either IDE, or CHIR for between 5-25 days, or until the appearance of hESC-RPECs (FIG. 5). hESC-RPECs can be expanded in a suitable culture medium (e.g., BM2), supplemented with iRock at least 20 minutes prior to passaging hESC-RPECs. hESC-RPEC cultures can be matured by allowing cultures to become highly confluent, and maturation can be further enhanced by reduction in serum component of the medium to <10%, 5%, 2%, <2%, or 0%. An example of a suitable basal medium is RPE Maturation Medium (RMM). RMM may or may not be supplemented with one of the following: IDE, CHIR, Forskolin, Rolipram, or iRock, depending on the needs of the culture.
Small Molecule Differentiation of hESCs to RPECs Under Defined Conditions HESC cultures were prepared for differentiation by supplementing mTeSR™1 with 10 uM Y-27632 (Rock inhibitor) (Sigma) for at least one hour prior to single cell dissociation with TrypLE™ Express (Gibco), counted and replated onto plates pre-coated with reduced growth factor Matrigel™ (RGFMG) (Corning) at high density (150,000 cells/cm2) in mTeSR™1 medium, supplemented with 10 uM Y-27632 and cultured overnight. The following day, cultures were refed fresh mTeSR™1 medium, without Rock inhibitor cultured for another 18-48 hours, or until cell cultures were nearly confluent (FIG. 2). Subsequently, cells were cultured in Primary Differentiation Medium (PDM) (containing 100 nM LDN193189, 10 uM SB431542, 5 uM CKI-7, and supplemented with 10 mM Nicotinamide) for 45 hours, before being further supplemented with 10 uM Rock inhibitor for an hour (FIG. 3 A). Differentiating cultures were single cell dissociated using TrypLE™ Express, re-suspended in PDM supplemented with 10 mM Nicotinamide and 10 uM Rock inhibitor, and formed into 3D cell aggregates of approximately 1500 cells/aggregate, using the AggreWellP400 (StemCell Technologies) (FIG. 3B), and cultured overnight. After 12-18 hours, the cell aggregates. The cell aggregates were cultured in suspension in Corning® Costar® Ultra-Low attachment 6-well plates (Corning) in primary differentiation medium (with 10 mM Nicotinamide), until day 4 or day 6, to differentiate as generate 3D aggregates of hESC-derived eyefield cells (ANEBs) to eyefield progenitor cells (FIG. 4A). At day 6, ANEBs were re-seeded onto RGFMG coated plates in RPEC Differentiation Medium (RDM) (containing 250 nM IDE-2 and 3 uM CHIR99021). ANEBs attached to the plate and the outgrowths were assessed for the appearance of immature RPE-like morphology (FIG. 8). ANEB outgrowths were cultured in RDM until day 14. Some putative hESC-RPEC cultures were maintained in an undisrupted form on the plates, while others were single cell dissociated and re-plated onto RGFMG at 150,000 cells/cm2 and cultured in Base Medium 2 (BM2), or RPEC Culture Medium (RCM), both supplemented with 10 uM Y-27632 until medium change the following day. hESC-RPEC cultures that are not dissociated may be maintained in BM2, without further supplementation, or in RMM, to generate mature hESC-RPECs within 21-28 days of the differentiation process (FIG. 9).
hESC-RPEC Expansion hESC-RPEC cultures can be expanded by culturing at moderate densities (e.g., 10,000-50,000 cells/cm2 in RCM (with or with out Y-27632) may be seeded on RGFMG, Vitronectin XF, Laminin 111, or LN521 at an optimal density of 50,000-100,000 cells/cm2, and cultured in RCM.
hESC-RPEC Maturation hESC-RPEC cultures can be matured by culturing at higher densities (e.g., 100,000-200,000 cells/cm2) in RMM (with or without Y-27632), and may be seeded on RGFMG, Vitronectin XF, Laminin 111, or LN521, or a suitable equivalent.
Small Molecule Differentiation of hESCs to RPECs Under Defined and Xeno-Free Conditions hESC cultures were prepared for differentiation by supplementing mTeSR™2 with 10 uM Y-27632 (Rock inhibitor) (Sigma) for at least one hour prior to single cell dissociation with TrypLE™ Express (Gibco), counted and replated onto plates pre-coated with hrLN521 (Life Technologies), and seeded at high density (150,000 cells/cm2) in mTeSR™2 medium, supplemented with 10 uM Y-27632 and cultured overnight. The following day, cultures were refed fresh mTeSR™2 medium, without Rock inhibitor cultured for another 18-48 hours, or until cell cultures were nearly confluent. Subsequently, cells were cultured in Primary Differentiation Medium (PDM) (containing 100 nM LDN193189, 10 uM SB431542, 5 uM CKI-7, and supplemented with 10 mM Nicotinamide) until day 4. On day 4, cells were fed fresh primary differentiation medium, further supplemented with 10 uM Y-27632 for an hour, before single cell dissociation using TryPLE™ Express. Differentiating cells were then re-suspended in PDM supplemented with 10 uM Y-27632, and re-seeded at a density of 45,000 cells/cm2 on tissue culture dishes pre-coated with hrLN521, and cultured in PDM supplemented with 10 uM Y-27632, and cultured overnight. The following day, the medium was changed for fresh PD. At day 6, the culture medium was switched to RPEC Differentiation Medium (RDM) (containing 250 nM IDE-2 and 3 uM CHIR99021), and cells were assessed for the appearance of immature hESC-RPECs the outgrowths were assessed for the appearance of immature RPE-like morphology, between day 8 and 12. At day 12, the immature hESC-RPECs were single cell dissociated with TrypLE™ Express, and re-seeded at a density of 150,000 cells/cm2 on tissue culture dishes pre-coated with hrLN521, in RCM (supplemented with 10 uM Y-27632) for several days.
Expansion of Xeno-Free and Defined hESC-RPECs hESC-RPEC cultures were expanded by culturing at moderate densities (e.g., 10,000-50,000 cells/cm2 in RCM (with or without Y-27632) seeded on LN521 at an optimal density of 50,000-100,000 cells/cm2, and cultured in RCM. hESC-RPECs were passaged as required.
Maturation of Xeno-Free and Defined hESC-RPECs hESC-RPEC cultures can be matured by culturing at higher densities (e.g., 100,000-200,000 cells/cm2) in RMM (with or without Y-27632), seeded on LN521, or a suitable equivalent, until hESC-RPECs have reached maturity.
Xeno-Free and Defined Differentiation of hESCs to PhRCs hESC cultures were prepared for differentiation by supplementing mTeSR™2 with 10 uM Y-27632 (Rock inhibitor) (Sigma) for at least one hour prior to single cell dissociation with TrypLE™ Express (Gibco), counted and replated onto plates pre-coated with hrLN521 (Life Technologies), and seeded at high density (150,000 cells/cm2) in mTeSR™2 medium, supplemented with 10 uM Y-27632 and cultured overnight. The following day, cultures were refed fresh mTeSR™2 medium, without Rock inhibitor cultured for another 18-48 hours, or until cell cultures were nearly confluent. Subsequently, cells were cultured in Primary Differentiation Medium (PDM) (containing 100 nM LDN193189, 10 uM SB431542, 5 uM CKI-7, and supplemented with 10 mM Nicotinamide) until day 4. At day 4, the medium was changed to PDM1 (with XFSR adjusted to 10%). At day 5 differentiating cell cultures were supplemented with 10 uM Y-27632 for an hour, before single cell dissociation using TryPLE™ Express. Differentiating cells were then re-suspended in NRIM, supplemented with 10 uM Y-27632, and re-seeded at a density of 50,000 cells/cm2 on tissue culture dishes pre-coated with hrLN521, and cultured in NRIM supplemented with 10 uM Y-27632, overnight. The cultures were refed NRIM the following morning, and every 2 days, until day 11 of differentiation, whereby cell culture medium was switched to photoreceptor differentiation medium (PRDM) and the medium changed every three days, until day 21.

In addition to the above, the following are non-limiting examples of media formulations for use in performing the method of the present invention.

Base Medium 1 (Bm1)
    78% DMEM/F12 (Life Technologies)
    20% Xeno-Free Serum Replacer (Life Technologies)
    1% Non-Essential Amino Acids (Life Technologies)
    1% Sodium Pyruvate (Life Technologies)
    Beta Mercaptoethanol 1000× (1 µl/mL)

Primary Differentiation Medium (PDM)
    +Base Medium 1
    +iROCK
    +LDN
    +SB
    +CKI-7
    ±NIC RPEC Differentiation Medium (RDM):
    +Base Medium 1
    +iROCK (only days before and after splitting)
    +IDE-2 (or another member of the IDE family, e.g. IDE-1, or small molecules that mimic Activin A)
    ±CHIR Base Medium 2 (BM2)
    88% High Glucose, High Sodium Pyruvate DMEM (Life Technologies)
    10% Xeno-Free Serum Replacer
    1% NEAA
    1% Sodium Pyruvate
    Beta Mercaptoethanol 1000× (1 µl/mL)

RPEC Culture Medium (RCM)
    +Base Medium 2
    ±IDE
    ±CHIR
    ±iROCK

RPEC Maturation Medium (RMM)
    93% High Glucose, High Sodium Pyruvate DMEM (Life Technologies)
    5% Xeno-Free Serum Replacer (Life Technologies)
    1% NEAA
    1% Sodium Pyruvate
    ±IDE
    ±CHIR
    ±Forskolin
    ±Rolipram
    Beta Mercaptoethanol 1000× (1 µl/mL)

Neural Retinal Induction Medium (NRIM)
    97.5% DMEM/F12 (Life Technologies)
    +2% Xeno-free serum replacer (Life Technologies)
    +1×N2 Supplement
    +1×B27 Supplement
    ±iROCK
    +DAPT
    +Purmorphamine
    +Retinoic Acid
    ±CKI-7

PhR Differentiation Medium (PRDM)
    97.5% DMEMIF12
    +2% Xeno-free serum replacer
    +1×B27 Supplement
    +Purmorphamine
    +Retinoic Acid
    +Taurine
    ±Triiodothyronine In addition to the above, the following are small molecules for use, either necessarily or optionally, in performing the method of the present invention.
    LDN193189 (0.1 nM-100 uM, 100 nM) Miltenyi Biotech
    SB431542 (10 nM-10 mM, 10 uM) Sigma
    CKI-7 (0.5 nM-0.5 mM, 5 uM) Sigma
    Nicotinamide (10 nM-10 mM, 10 uM) Sigma
    IDE-2 (10 nM-10 mM, 250 nM) Miltenyi Biotech
    CHIR99021 (10 nM-10 mM, 3 uM) Sigma
    Y-27632 (1 nM-10 mM, 10 uM) Sigma
    Forskolin (10 nM-10 mM, 10 uM) Sigma
    Rolipram (10 nM-5 mM, 1 uM) Sigma
    DAPT (10 nM-10 mM, 10 uM) Sigma
    Retinoic Acid (5 nM-20 mM, 500 nM) Sigma
    Purmorphamine (0.1 nM-1 mM, 10 nM)
    Taurine (10 nM-10 mM, 100 uM) Sigma hESC Cell Lines The human embryonic stem cell lines MEL1 (NIH Registry no. 0139, StemCore, Brisbane, QLD, Australia), Genea_002 (NIH Registry no. 0151, Genea Biocells, Sydney, NSW, Australia), and Genea_015 (NIH Registry no. 0228, Genea Biocells, Sydney, NSW, Australia), were either cultured under feeder-free conditions, defined and feeder free conditions, or defined and xeno-free culture conditions, depending on purpose.

RNA & qPCR

Total RNA was extracted from cells using PureZOL™ RNA Isolation Reagent (BioRad, USA) according to the manufacturer's instructions. The RNA concentration and the A260:A280 ratio were quantified using a NanoDrop 2000c (Thermo Scientific, USA). One microgram of RNA was reverse transcribed using the iScript™ cDNA synthesis kit (BioRad, USA), and quantitative PCR analysis (qPCR) was carried out with SsoFast™ EvaGreen® Supermix (BioRad, USA) on a BioRad CFX96 Touch Real-Time PCR machine (BioRad, USA). All qPCR experiments were performed in triplicate.

Immunofluorescent Analysis

Cell samples were grown on reduced growth factor matrigel-coated glass coverslips were fixed with 4% paraformaldehyde (Sigma Aldrich, USA) for 10 min at room temperature, then permeabilised with 0.1% TritonX-100 in 1×PBS for 3 min. The samples were then incubated with primary antibodies (1:40-1:1000, depending on antibody) in blocking buffer consisting of 3% bovine serum albumin (Sigma Aldrich, USA) in PBS for 90 minutes at room temperature. The specimens were washed and incubated with appropriate Alexa-Fluor-conjugated secondary antibodies (1:500, Invitrogen) for 30 minutes in the dark at room temperature. Cell nuclei were co-stained using Hoechst 33342 (1:1000, Life Technologies, USA). F-actin was stained with Alexa-Fluor-488-conjugated Phalloidin (Phalloidin-488) (1:40, Life Technologies, USA) for 30 minutes in the dark at room temperature. Images were taken though a Nikon C1 confocal microscope (Nikon Instruments Inc., USA).

Flow Cytometry

Cell samples were fixed in 4% paraformaldehyde in PBS (Gibco). For internal marker studies, samples were permeabilised with 0.2% Triton X-100 (Roche, Indianapolis, Ind., USA). The samples were labelled with primary or isotype control antibodies for 30 minutes at 4° C. Primary and isotype control antibodies that were not conjugated to fluorophores were labelled with fluorophore-conjugated secondary antibodies for 30 minutes at 4'C. The labelled samples were analysed using a BD FACSVERSE™ flow cytometer (BD Biosciences, San Jose, Calif., USA). Data analysis was performed on BD FACSuite™ (BD Biosciences).

Scanning Electron Microscopy

Cells were cultured on coverslips that were coated with reduced growth factor matrigel, laminin 521 or vitronectin XF. Samples were washed twice with 1×PBS and fixed in 3% glutaraldehyde (Sigma Aldrich, USA) in PBS for 24 hours, and dehydrated through a series of increasing graded ethanol in PBS solutions (25%, 45%, 55%, 65%, 75%, 85%, 90%, 95% and 100%), then chemically dried by rinsing twice with hexamethyldisilazane (HMDS, Sigma Aldrich, USA), and finally air-dried overnight Samples were mounted on aluminium stubs and gold-coated by a gold-coater sputter (Jeol). Images taken with a Neoscope JCM-5000 Jeol bench-top SEM (Jeol).

Transepithelial Electrical Resistance

Transwells® (Corning) were coated with Reduced Growth Factor Matrigel (Corning), seeded with 2×105 hESC-RPECs/cm2 (passage 5) and cultured for 12 weeks in maturation medium. TER values (Ω*cm2) were obtained by using an STX2 electrode (World Precision Instruments, USA) from 3 replicates, in each measured in triplicate. TER measurements were taken at 6 and 8 weeks. Background resistance values were obtained by measuring triplicate equivalent, Growth factor-reduced matrigel-coated transwells in identical medium, which were then subtracted from the cell-based readings.

Cytokine ELISA

To confirm the polarised secretion of VEGF and PEDF, apical and basal media samples were taken from triplicate wells for hESC-RPEC seeded transwells (as per TER measurement), 48 hours after feeding. ELISA detection of VEGF was performed using the human VEGF ELISA Kit (Cat #EK05039; Boster Biological Technologies Ltd, Pleasanton, Calif., USA) as per manufacturer's instructions. PEDF was detected using Human PEDF ELISA Kit (Cat #E0784h; Wuhan EIAab Science Ltd, Wuhan, China). Absorbance was measured at 450 nm using a microplate reader (Modulus™ II Microplate Multimode Reader; Turner Biosystems, USA) against standard curves for both VEGF and PEDF.

Phagocytosis

Briefly, the microspheres were prepared by treatment with vitronectin XF (5 µG/ml) (StemCell Technologies, Vancouver, Canada). (5 µG/ml) in 20 mM HEPES binding buffer (HBB) and incubated for 1 h at 37° C., followed by rinsing and blocking with 0.1% bovine serum albumin (BSA; A-7030, Sigma Aldrich) in HBB and incubated for a further 1 h at 37° C. Fluorescent microspheres treated with 0.1% BSA in HBB only for the two incubation times were used as a negative control. Coated and controlled microspheres were concentrated and fed to hESC-RPECs at 106 spheres per cell, cultured 24 h at 37° C. The cultures were then rinsed with 1×PBS followed by five-minute incubation in trypan blue. The process was repeated 4 times to remove non-phagocytosed beads. Cells were then fixed in 3.7% formaldehyde in PBS, rinsed thrice in PBS 3×, before staining with Hoechst 33342 (1:1000, Life Technologies, USA) and Alexa-Fluor-488-conjugated Phalloidin (1:40, Life Technologies, USA) for 30 minutes in the dark at room temperature. Cells were subsequently imaged as z-stacks using Confocal laser scanning microscopy (Nikon A1R).

It should be noted that the percentages of the supplements as listed in the above formulations may vary as well as the combination of supplements and that the listing of additional supplements in the above examples should in no way limit the scope of the invention. Also, the supplements mentioned above may be replaced with other analogous supplements. Further, whilst the invention has been described with respect to the above specific embodiments and Examples, it should be recognized that various modifications and changes may be made to the invention by those skilled in the art which also fall within the scope of the invention.

Results

Figure 6:
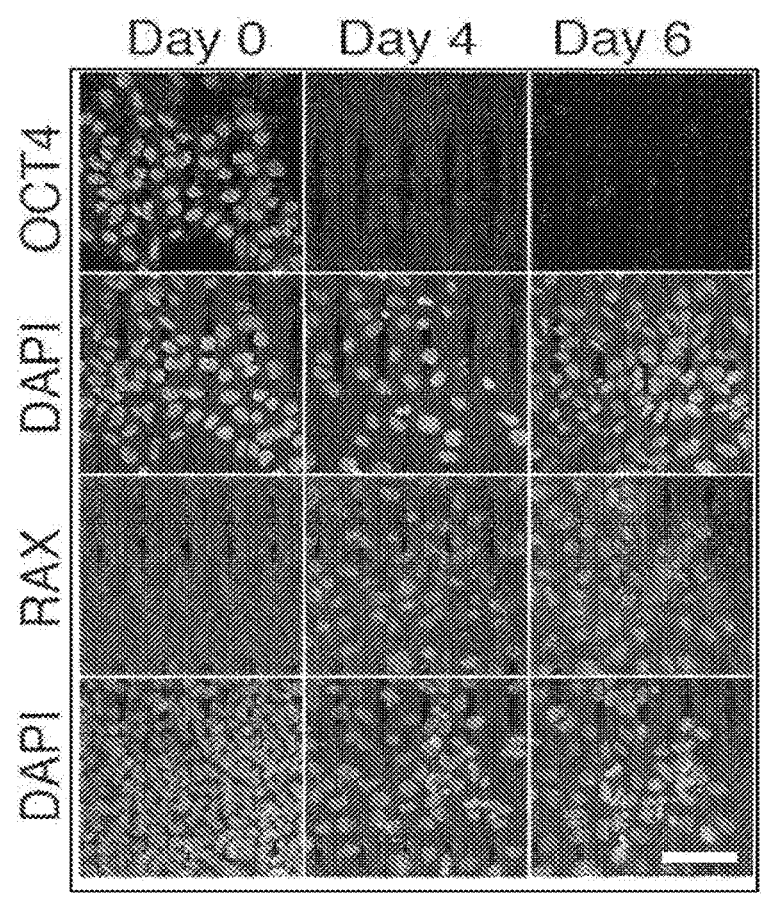
FIG. 6 Immunofluorescent analysis of Oct4 and Rax expression during differentiation of hESCs to EFPCs indicates loss of the pluripotency, and differentiation to EFPCs, indicated by the down regulation of Oct4 and the upregulation of Rax by day 4, respectively.
Figure 7:
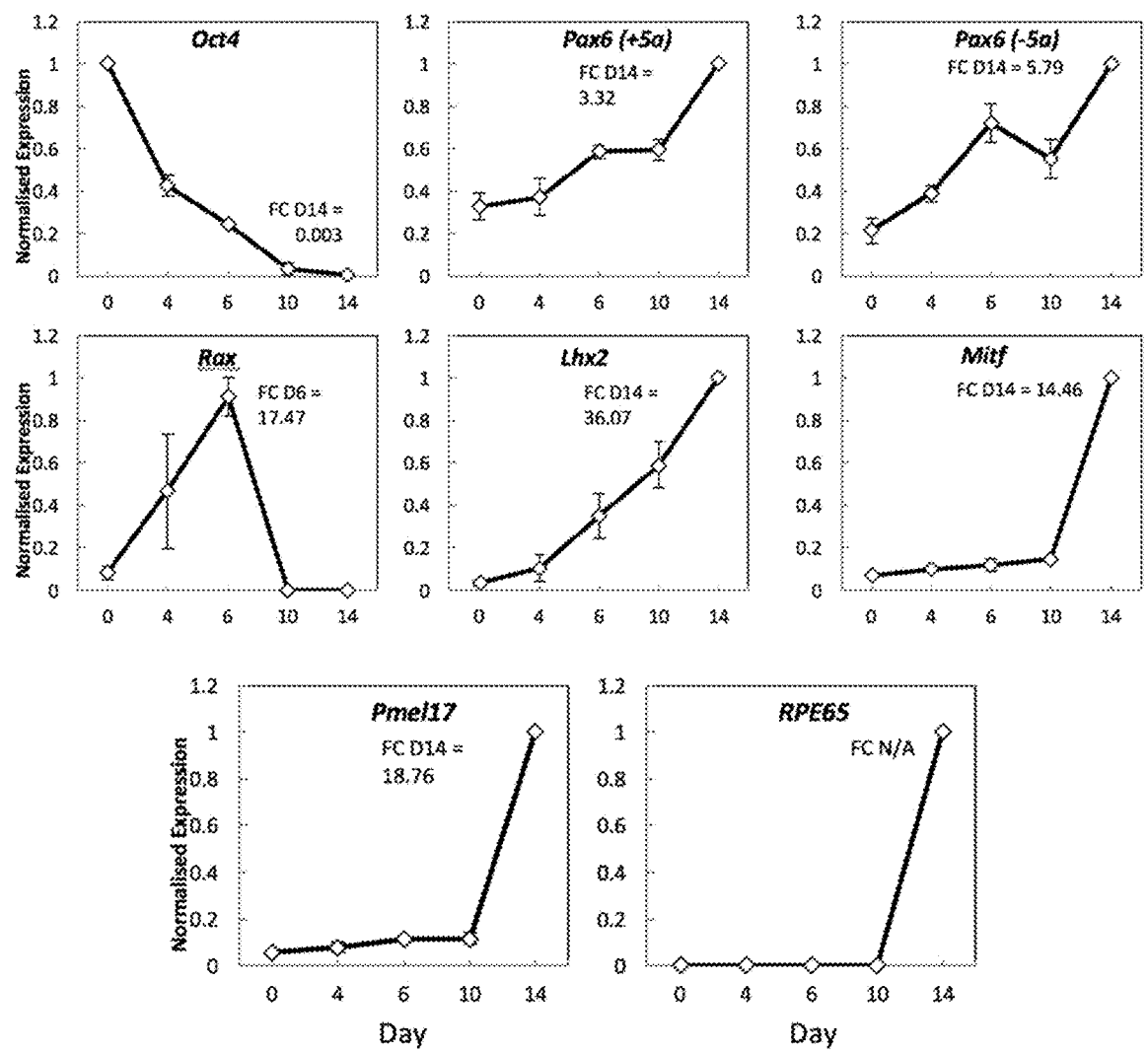
FIG. 7 qPCR detection of dynamic gene expression changes during differentiation of hESC (day 0) to EFPCs (day 4-6), and early RPECs (day 14). Expression at day 0 shows high expression of the pluripotent marker Oct4, very low, or null, levels of expression for neural markers Pax6 (-5a & +5a), EFPC markers Rax and Lhx2, and RPEC markers Mitf, Pmel17 and RPE65. After the initiation of differentiation, Oct4 expression is downregulated significantly by day 4, while neural and EFPC markers show high upregulation at days 4 and 6. Expression of Rax peaks at day 6 and is undetectable by day 10, as EFPCs are differentiated further towards an RPEC identity. Lhx2 expression continues to rise from day 0 through to day 14, and the RPEC markers, Mitf and Pmel17 are highly upregulated by day 14, while there is also expression of the mature RPEC marker RPE65 by day 14. (FC=Fold change values are calculated from the day of highest expression relative to day 0).

The hESC methods of the invention relating to the differentiation of human SCs towards the eyefield progenitor cells, that are Rax+ on day 4 and day 6 (FIG. 6), which has been confirmed by qRT-PCR expression of Rax, LHX2, Pax6(-5a) (FIG. 7). FIG. 31 shows a series combinatorial differentiation screens aimed at identifying the best small molecule combinations for the generation of retinal cells from hESCs. FIG. 31 A is a summary of experimental conditions designed to test the ability of each molecule to contribute to efficient RPEC differentiation within a 14-day period. Primary differentiation was from day 0-day 6, followed by secondary differentiation, or RPE differentiation, from day 6 to day 14. Briefly, hESC differentiation to RPE in the absence of LDN is low. The addition of LDN to SB and NIC showed improved differentiation, which was further enhanced in the presence of CKI-7. The role of CKI-7 on differentiation efficiency was tested in combination with a variety of combinations to determine the optimal signalling requirements for differentiation. The small molecule IDE-2 was tested for its ability to functionally replace Activin A in a context for which it had not previously been tested. The combined use of IDE-2 with the GSK3b inhibitor resulted in the highest degree of hESC-RPEC differentiation by day 14, which was almost uniformly immature hESC-RPECs (FIG. 8). Although the effect of NIC on hESC-RPEC differentiation was positive during differentiation towards to the eyefield, but negative after. This is was not an intuitive result, given the protocols that expose cell culture to NIC for prolonged periods of time. Further optimisation of the 3D differentiation of hESCc to RPECs showed that optimal number of cells for a cell aggregate was between 1000-1500 cells/body (FIG. 31-B), while the optimal days to change initiate RPEC differentiation from the eyefield progenitor cell was day 6 (FIG. 31-C).

Figure 10:
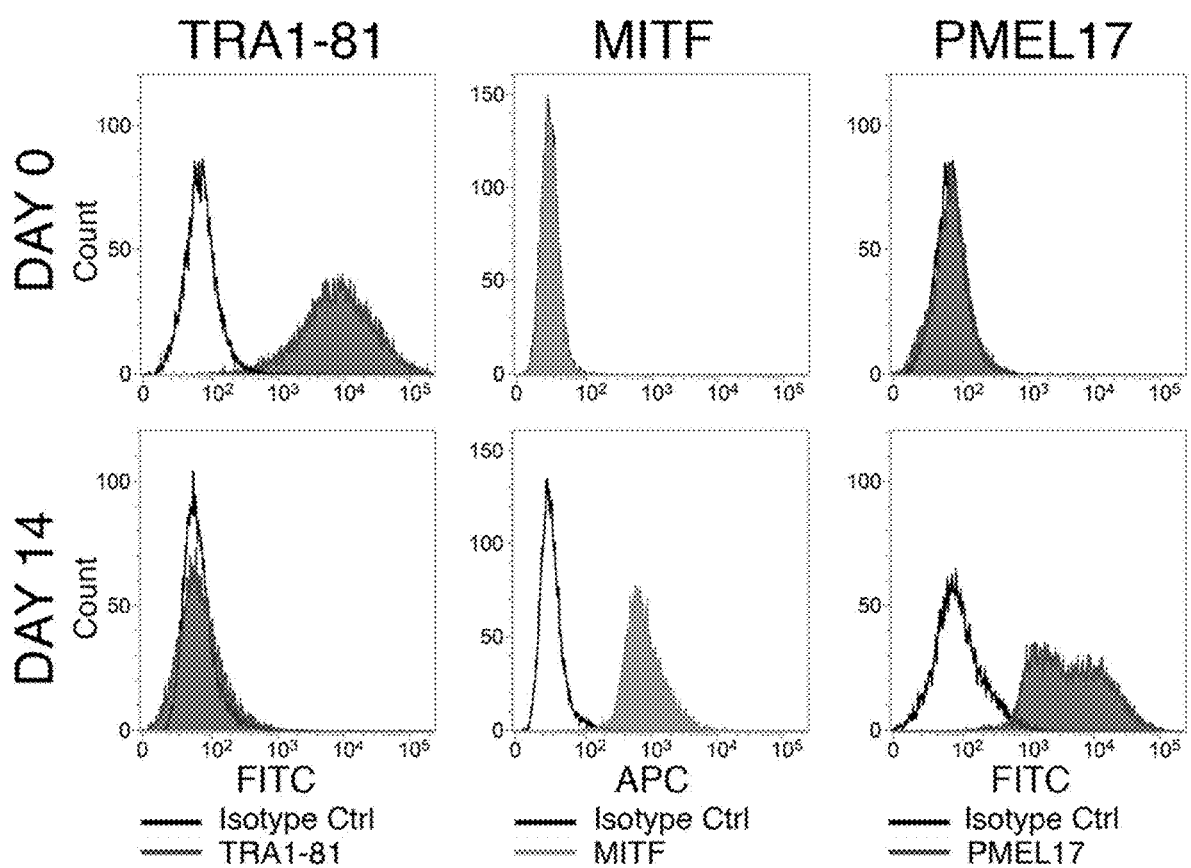
FIG. 10 Flow cytometric analysis of the pluripotent marker Tra1-81 and the RPE markers Mitf and Pmel17 in hESC cultures (day 0) and differentiation cultures at day 14 indicate rapid and highly efficient differentiation to hESC-RPECs by day 14.
Figure 11:
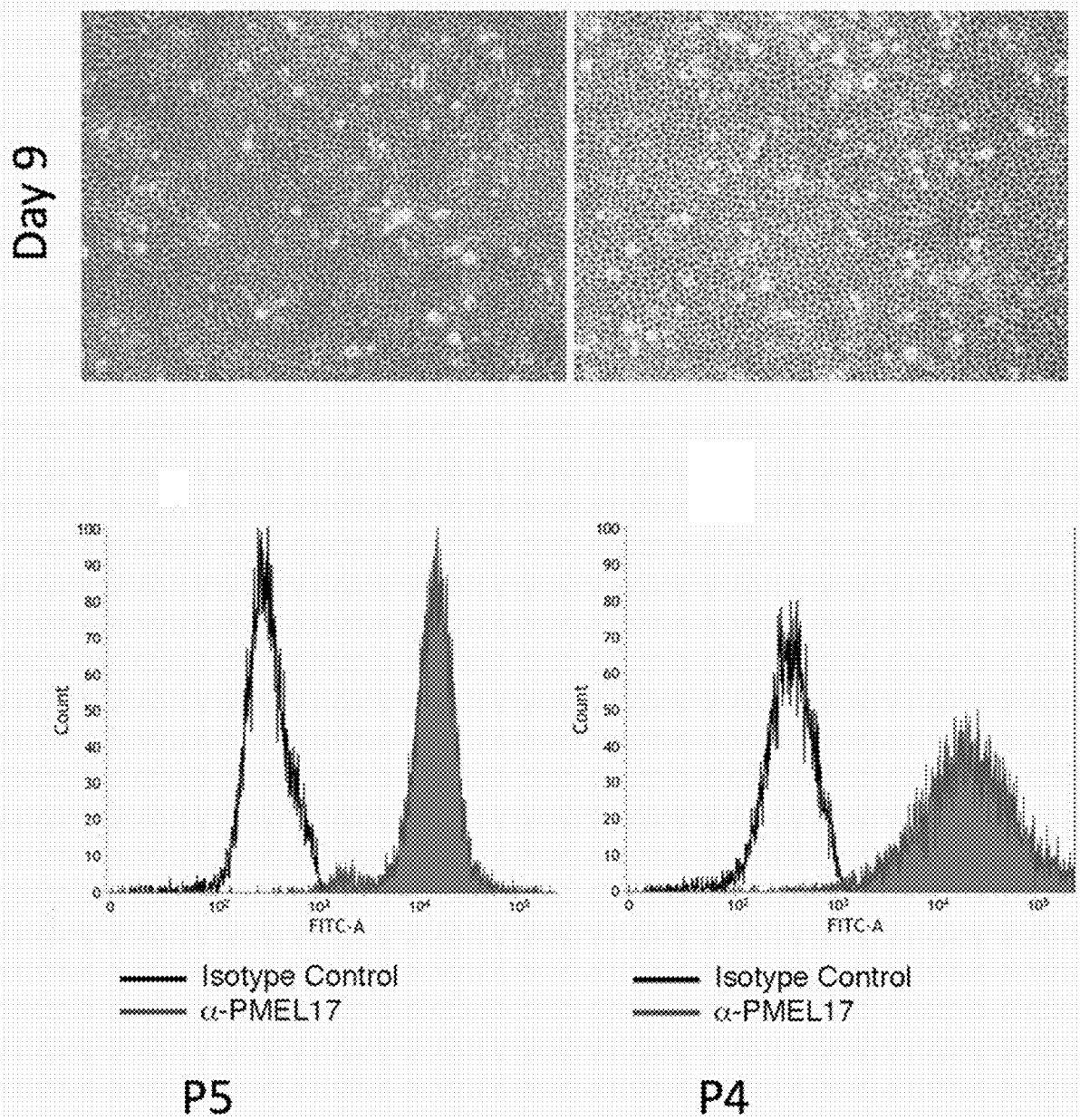
FIG. 11. (A) Small molecule differentiation of two hESC lines (Mel1 & Genea2) to immature hESC-RPEC via adherent differentiation results in the appearance of immature RPE cell morphology by day 9. (B) Flow cytometric analysis of the RPE markers Pmel17 in hESC-RPEC cultures generated from Mel1-hESCs and Genea2-hESCs demonstrate the maintenance of highly homogenous hESC-RPEC cultures after five and four passages, respectively.
Figure 12:
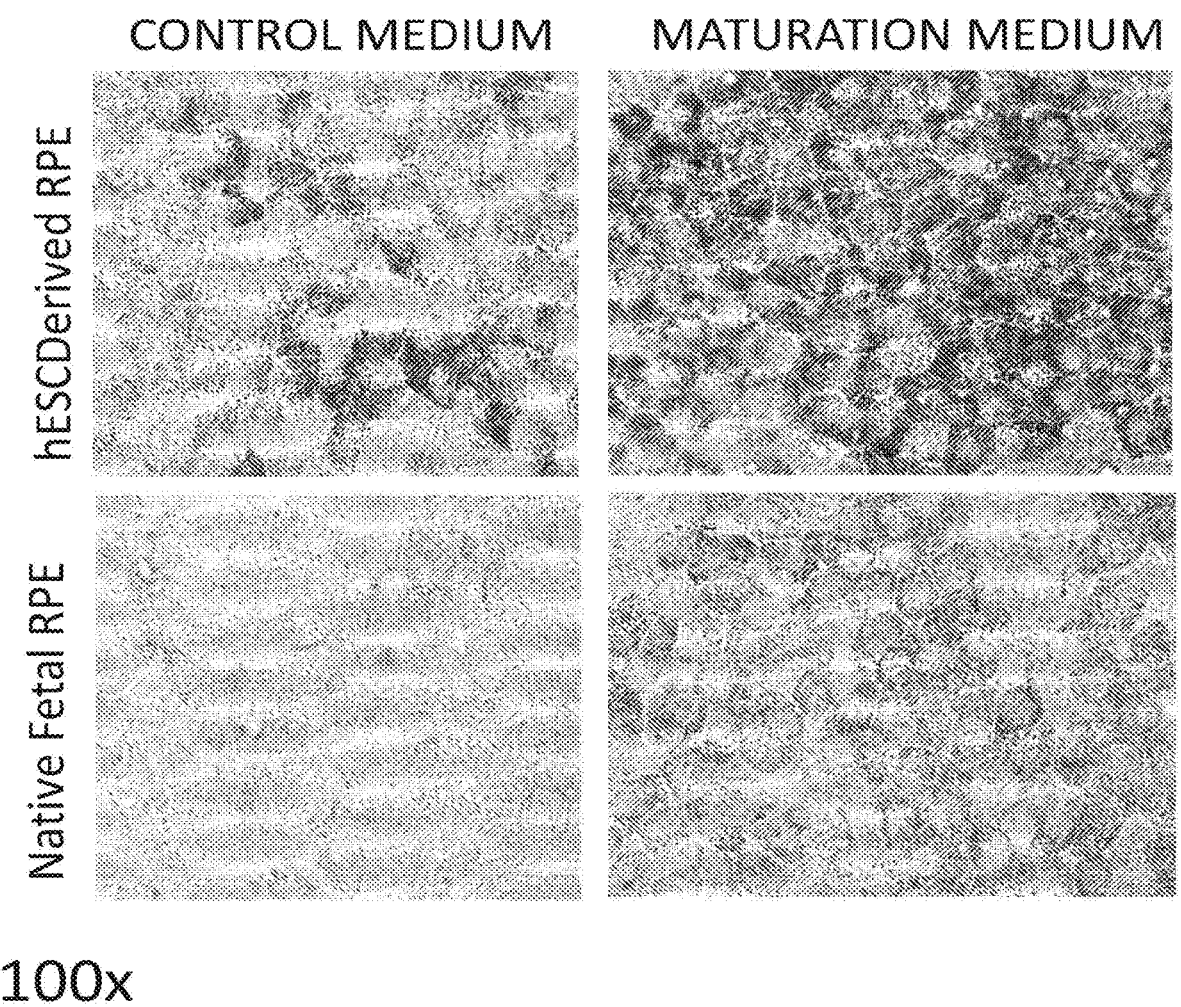
FIG. 12 Images showing the effect of BM1 control medium vs RPEC maturation medium (RMM) on hESC-RPE cells and Human Fetal RPE cell pigmentation after 21 days, seeded at 150,000 cells/cm2 on Reduced Growth Factor Matrigel™ and cultured for 21 days.

The results demonstrate the methods of the invention for the differentiation of hESCs to RPECs is rapid (within 8-14 days), and extremely efficient (typically above 85%, and often above 95%, as determined by flow cytometric analysis for the RPE markers Mitf and Pmel17+ at day 14) (FIG. 10) and fis robust across differentiation formats and cells lines (FIG. 11).

hESC-RPEC maturation is improved when cells are cultured in RPE Maturation Medium (Maturation), rather than Basal Medium 1 (Control), and this effect can also be reproduced in native foetal RPE cells (FIG. 12).

Figure 13:
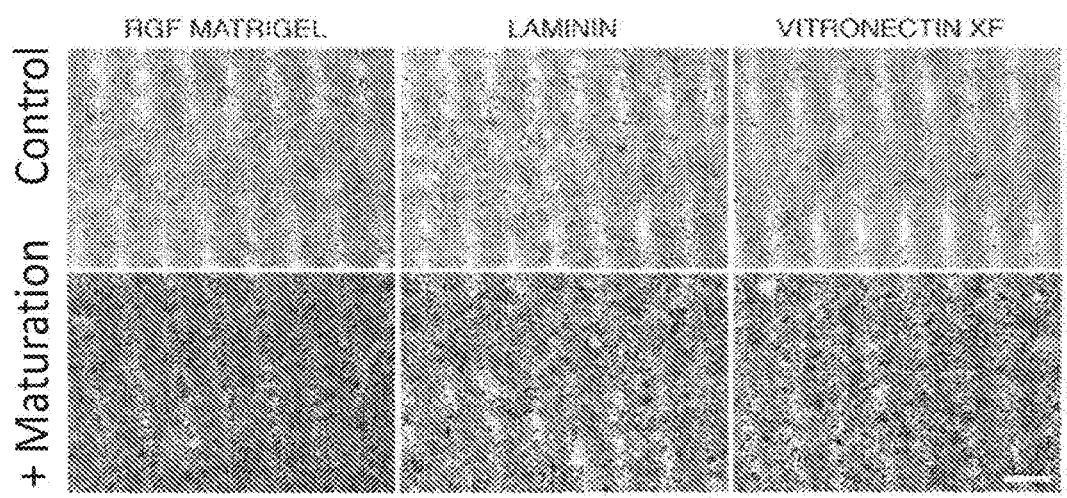
FIG. 13 Maturation of hESC-RPEC on reduced growth factor matrigel (RGF Matrigel™), mouse laminin 111 (Laminin), and human xeno-free vitronectin (Vitronectin XF) in control medium vs maturation medium and cultured for 21 days.
Figure 14:
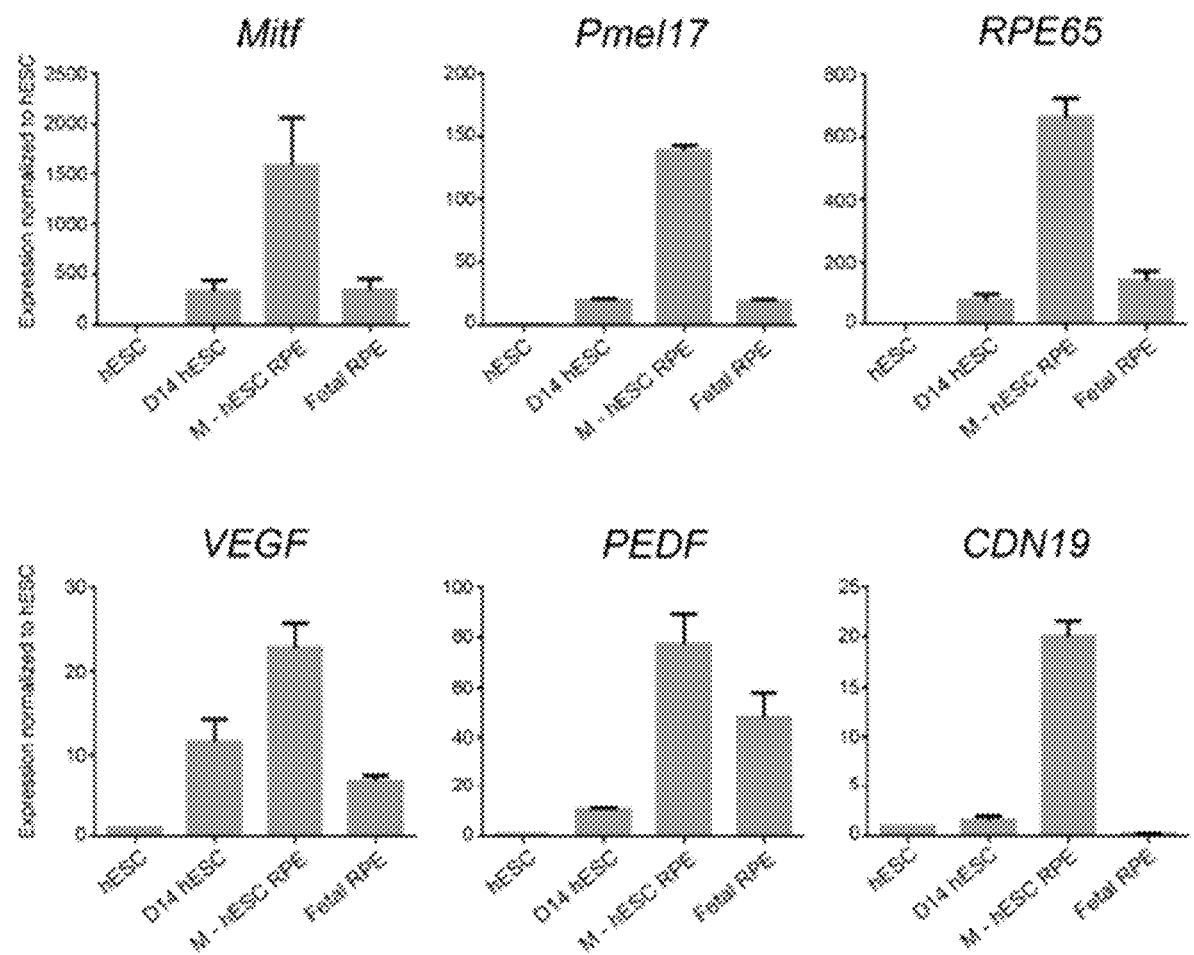
FIG. 14 qPCR detection of key markers of early and mature RPE cells in human embryonic stem cells (hESC), immature hESC-RPECs (D14 hESC), mature hESC-RPECs (M-hESC-RPECs), and human foetal RPE cell controls (Foetal RPE) showing the effect of maturation medium on the expression of RPE cell markers (Mitf and Pmel17), a mature RPE cell marker and critical component of the visual cycle (RPE65), the expression of cytokines (VEGF and PEDF), and the expression of mature tight junction component (CDN19), during the culture of immature hESC-RPECs in maturation medium for 21 days.
Figure 15:
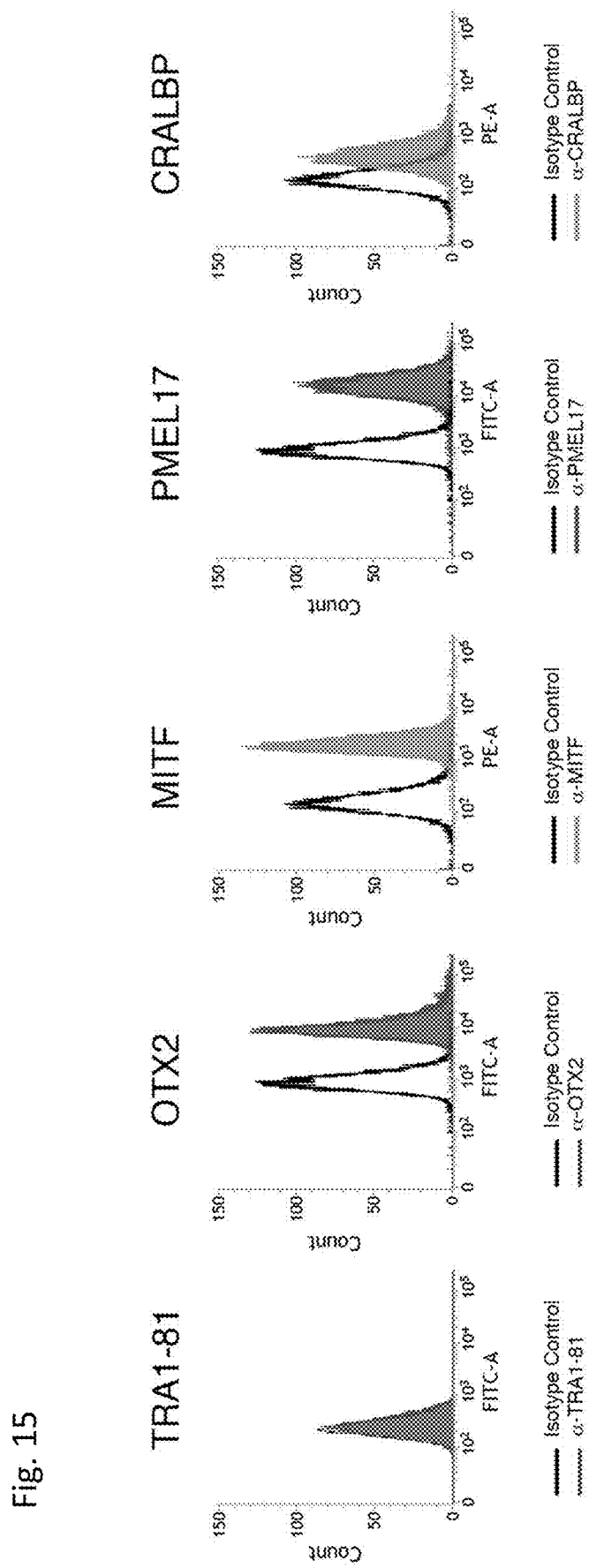
FIG. 15 Flow cytometric analysis of TRA1-81, OTX2, MITF, PMEL17 and CRALBP expression in hESC-RPE cell cultures at passage 8 demonstrates the absence undifferentiated pluripotent stem cells and the maintenance of RPE marker expression.
Figure 16:
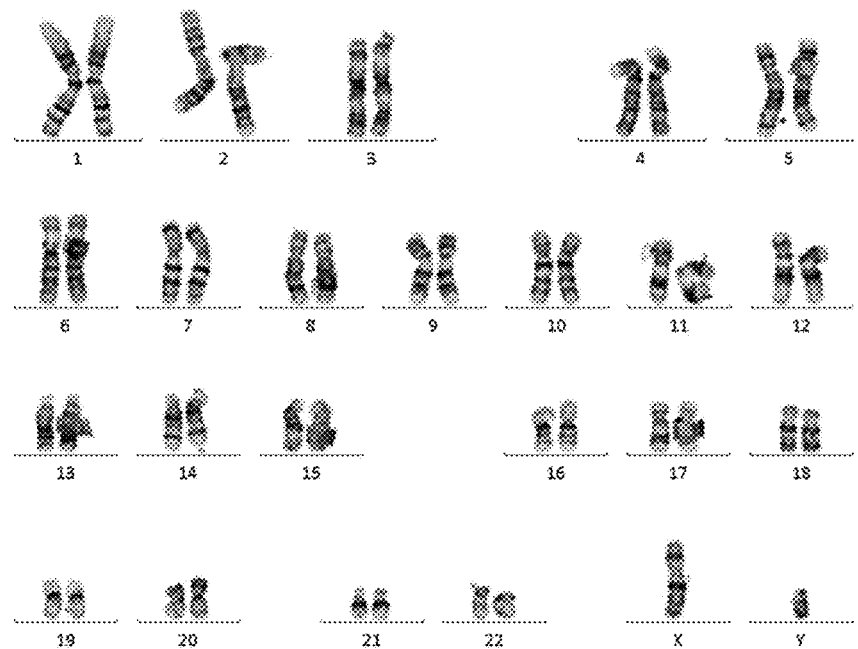
FIG. 16 Normal Karyotypes from hESC-RPECs generated from two independent example hESC lines (Mel1 and Genea2), after at least 5 passages, and one recovery from cryopreservation after approximately 12 months.
Figure 16:
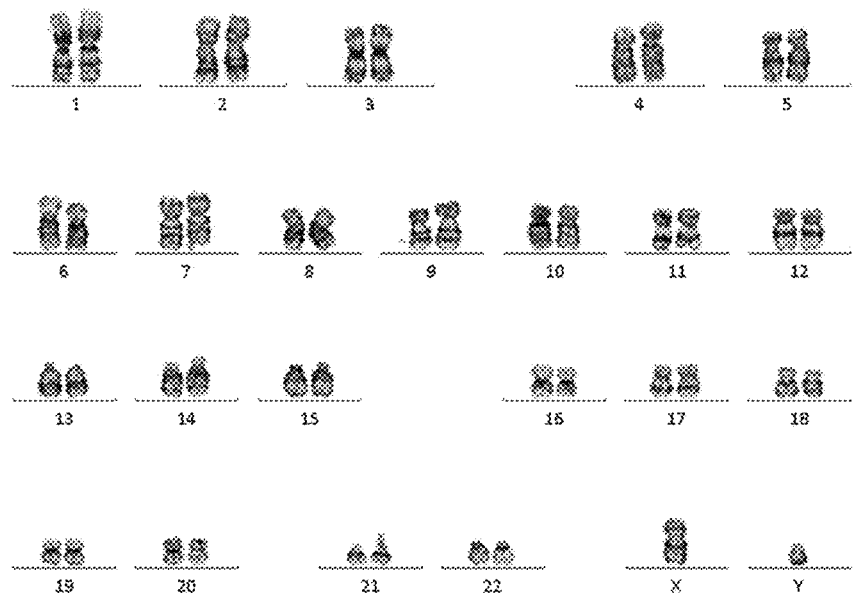
Figure 17:
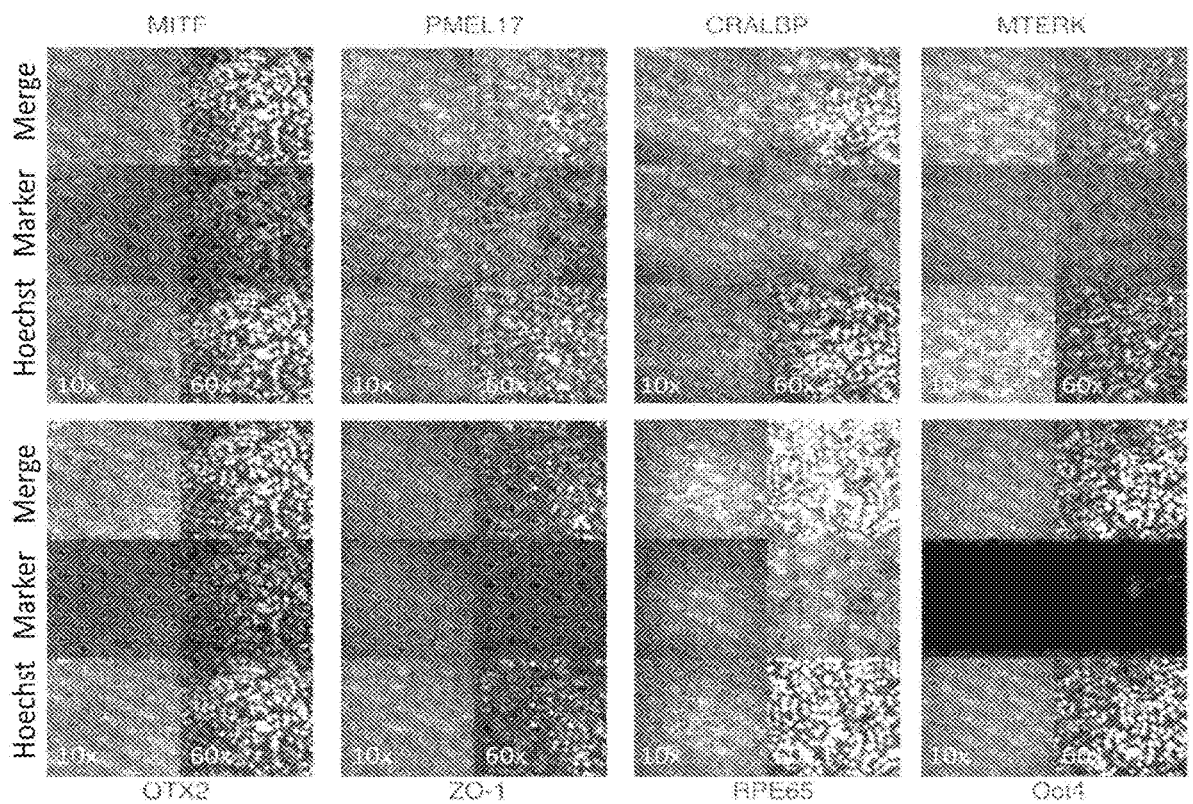
FIG. 17 Immunochemical analysis of hESC-RPECs differentiated under defined and feeder-free conditions demonstrating the homogeneous expression of critical RPE markers (MITF, OTX2, PMEL17, ZO-1, CRALBP, RPE65, MTERK) and the absence of the pluripotent marker (Oct4) in mature hESC-RPE cell cultures, at day 28. Cell cultures were passage 5.
Figure 18:
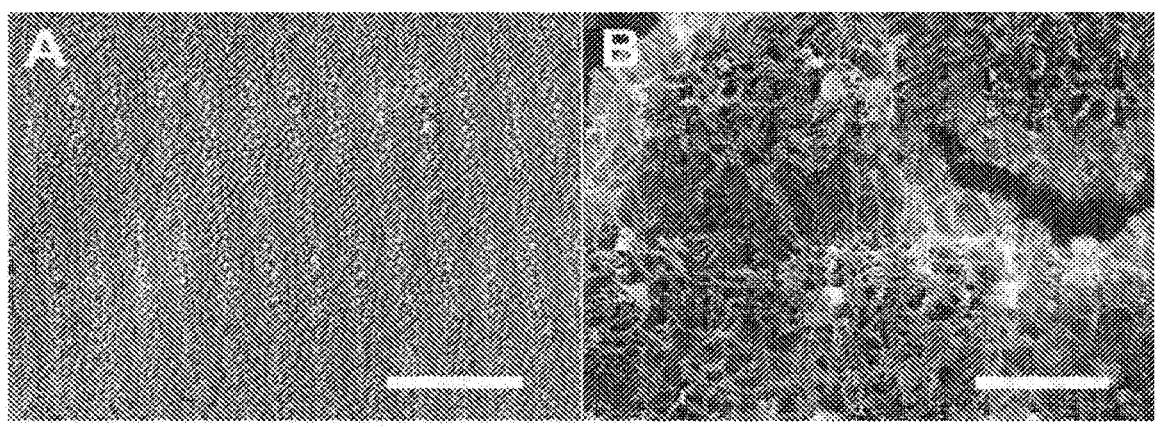
FIG. 18 Scanning electron microscopy (SEM) images of mature hESC-RPE cells cultured for 21 days on a xeno-free substrate (Vitronectin XF) for 21 days under maturation conditions. (A) Low magnification SEM image showing a monolayer, or sheet, of hESC-RPE cells (Size bar=100 μm). (B) High magnification SEM image showing the morphology of mature hESC-RPE cells with highly developed microvilli (Size bar=2 μm).
Figure 19:
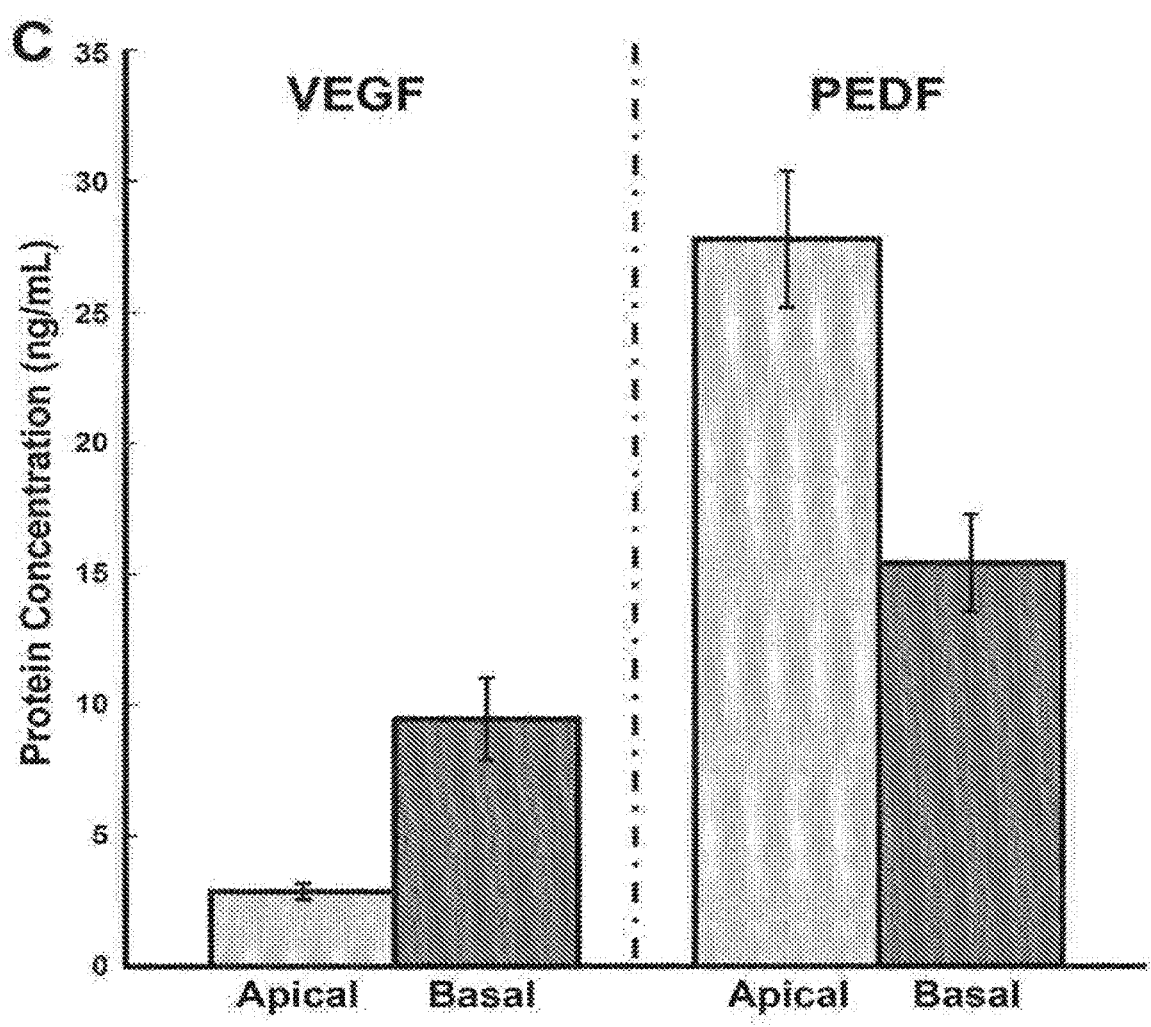
FIG. 19 Detection of apically and basally secreted cytokines, VEGF and PEDF, by mature hESC-RPE cells, cultured on Transwells indicate hESC-RPEC maturity, cell polarization and cytokine function.
Figure 20:
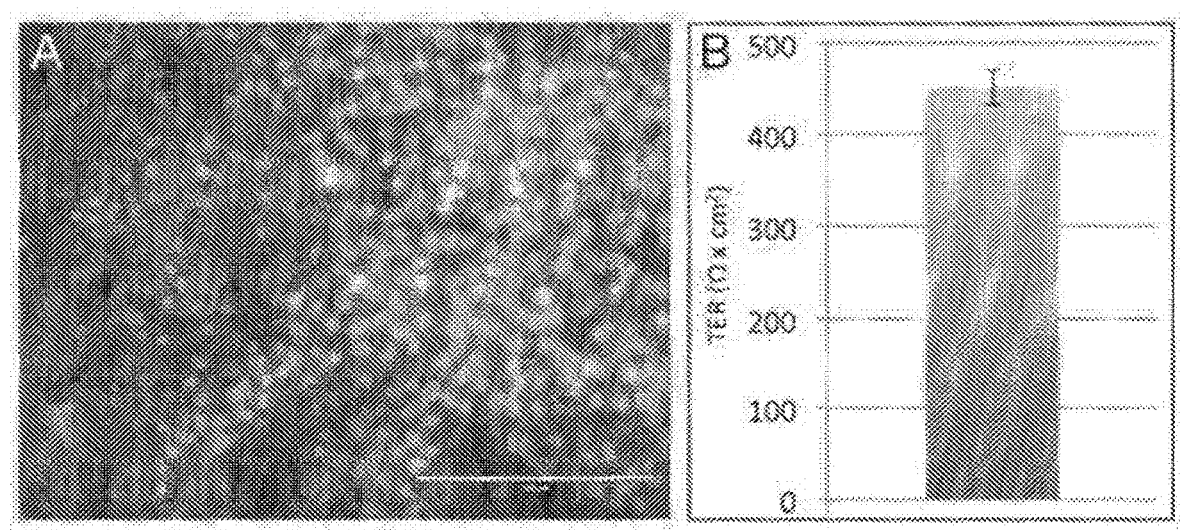
FIG. 20. (A) Mature hESC-RPE cultures stained with falloidin-488 show f-actin localisation at cell boundaries between in mature hESC-RPE cell cultures, cobblestone morphology and the absence of actin stress fibres. (B) TER values of mature hESC-RPECs were seeded at 150K cells/cm2, grown on Transwells™ for six weeks, and measured in triplicate (3 wells, 3 measurements/well) demonstrate the functional maturation of hESC-RPECs by formation of a tight epithelium.
Figure 21:
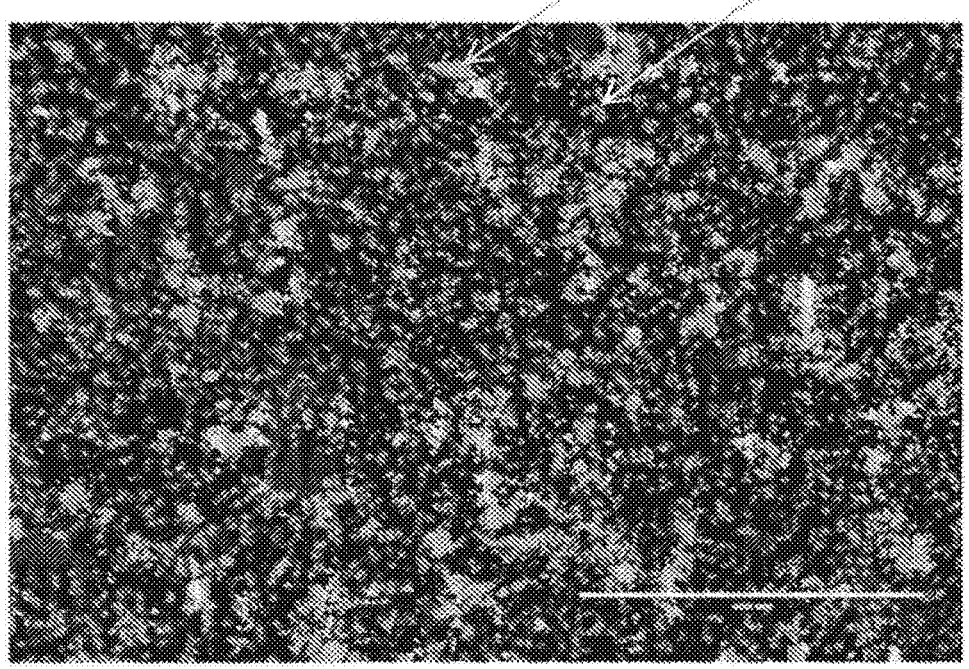
FIG. 21 Mature hESC-RPE cells phagocytose vitronectin-XF coated microspheres.
Figure 21:
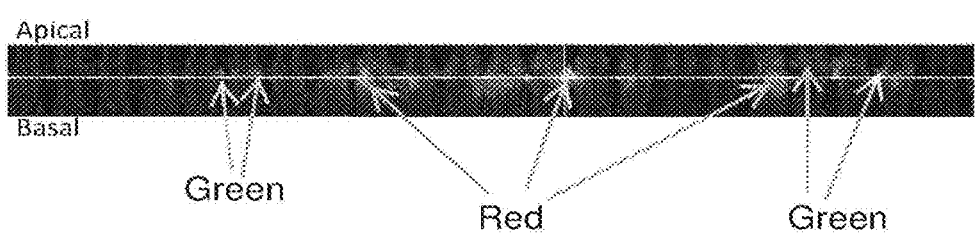

The effect of surface substrate on hESC-RPEC maturation did not appear to make an obvious difference in maturation and pigmentation of the hESC-RPEC monolayers, and also confirms that hESC-RPECs with the methods of the invention can be cultured under xeno-free conditions (FIG. 13). qPCR analysis of immature and mature RPE cell markers confirm that culture of hESC-RPECs under RMM significantly upregulates the expression of all markers tested. Of particular interest in the upregulation on Pmel17, which correlates with increased pigmentation of mature hESC-RPECs, while increased RPE65 expression indicates upregulation of visual cycle pathway, and the cytokines correlate with the known role of RPE cells, in the maintenance of the retinal and choroidal cell health (FIG. 14). The hESC-RPECs generated by the methods of the invention demonstrate a highly homogeneous and stable phenotype, even after prolonged culture (FIG. 15) as well as a stable karyotype (FIG. 16). Mature hESC-RPECs express critical markers of RPE cell identity and function, in a highly homogeneous manner (FIG. 17), which is also reflected in the development sheets of mature apical microvilli (FIG. 18). Mature hESC-RPECs produce and secrete critical cytokines VEGF and PEDF, with correct polarity of secretion (FIG. 19). F-actin structure of hESC-RPEC cultures show cobblestone morphology and lack of actin stress fibres in mature hESC-RPEC cultures (FIG. 20-A). Further, the establishment of a tight epithelium of mature hESC-RPECs is supported by high TER measurements (FIG. 20-B), and demonstrate phagocytically functionality (FIG. 21). To summarise these data, the hESC-RPECs generated and cultured according to the methods of the invention result in the fast and efficient generation of hESC-RPECs that can be cultured as homogenous and functional cultures that can have utility in the treatment of retinal disease and dysfunction.

Figure 22:
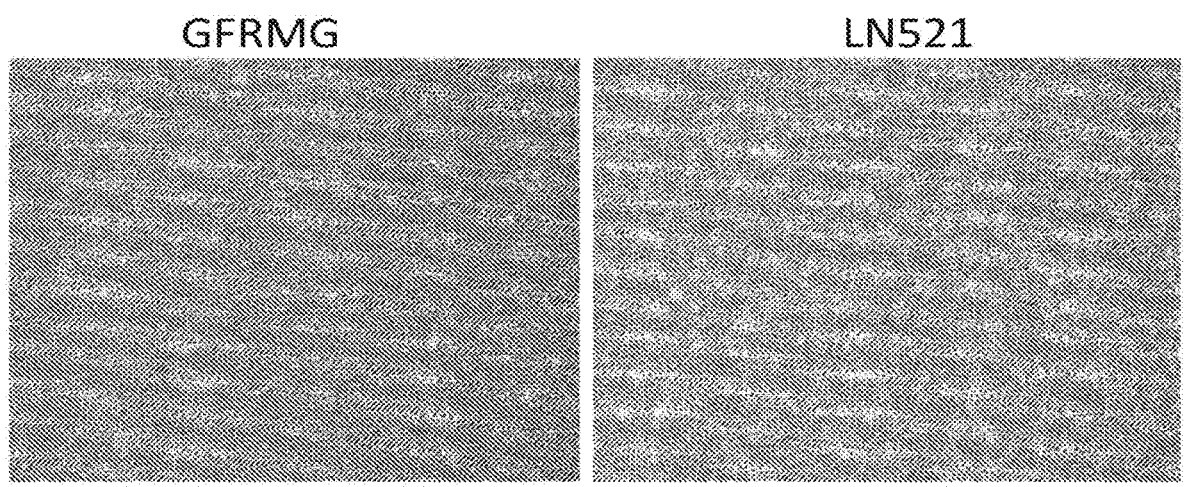
FIG. 22 Morphology of hESC-RPE cells 24 hours after seeding on GFRMG and LN521 at optimal density (150 K/cm2) illustrating equivalent cell attachment between GFRMG (Corning) and the xeno-free substrate, Laminin 521 (Life Technologies).
Figure 23:
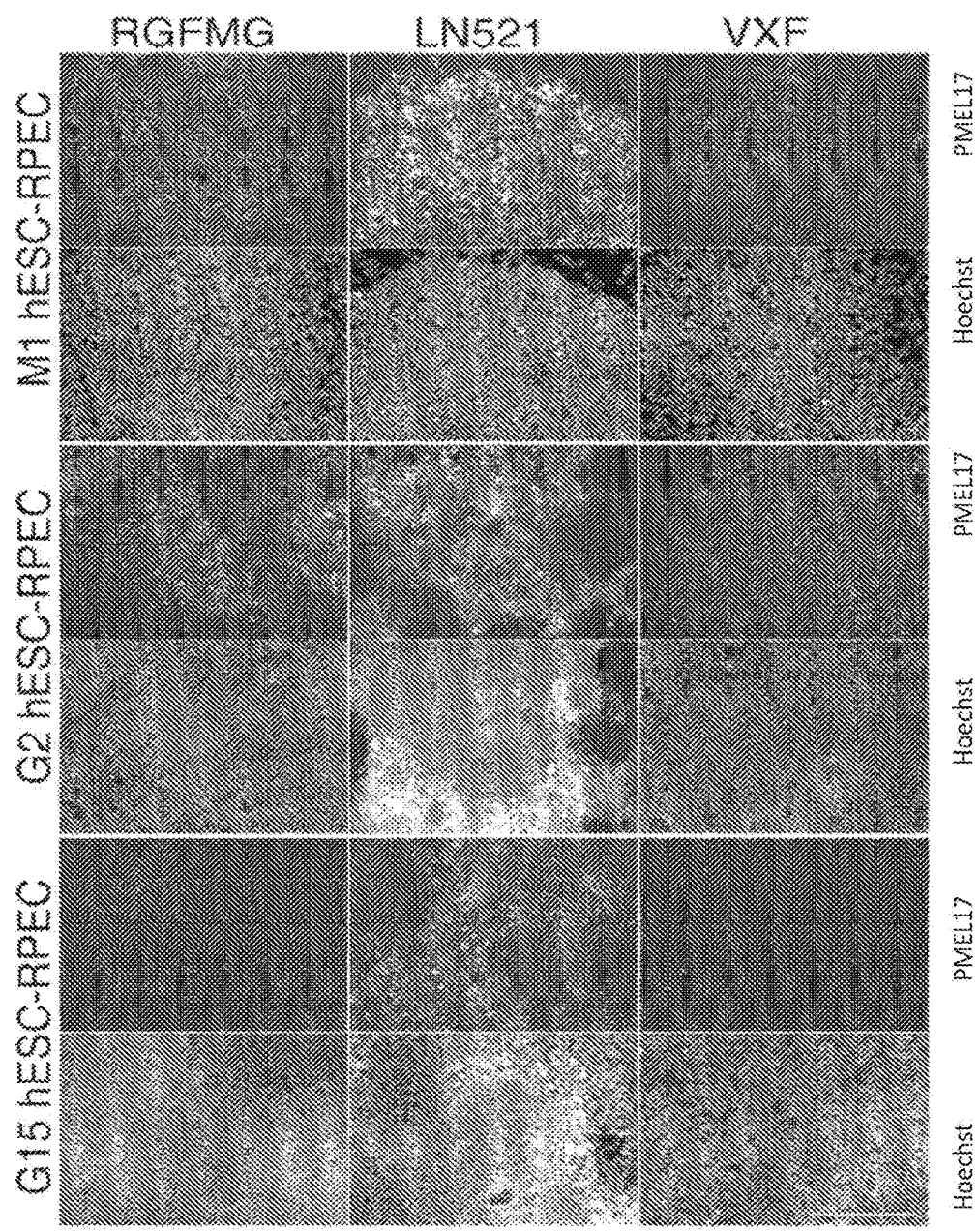
FIG. 23 Immunofluorescent analysis of early expression of the RPE marker PMEL17 on LN521, compared with RGFMG and Vitronectin XF, showing a preference for LN521 as a preferred xeno-free substrate for hESC-RPEC culture and generation.

Methods of the invention include the ability to differentiate SCs to RPECs under defined and xeno-free conditions. In search for a xeno-free substrate it was noted that hEC-RPECs were able to attach and grown well on hrLN521 (Life Technologies) (FIG. 22). Further comparison of early differentiating cultures seeded on RGFMG, or two alternative, xeno-free substrates showed that the enhances expression of the RPEC marker, Pmel17 on hrLN521 vs Vitronedin XF™ (FIG. 23).

Figure 24:
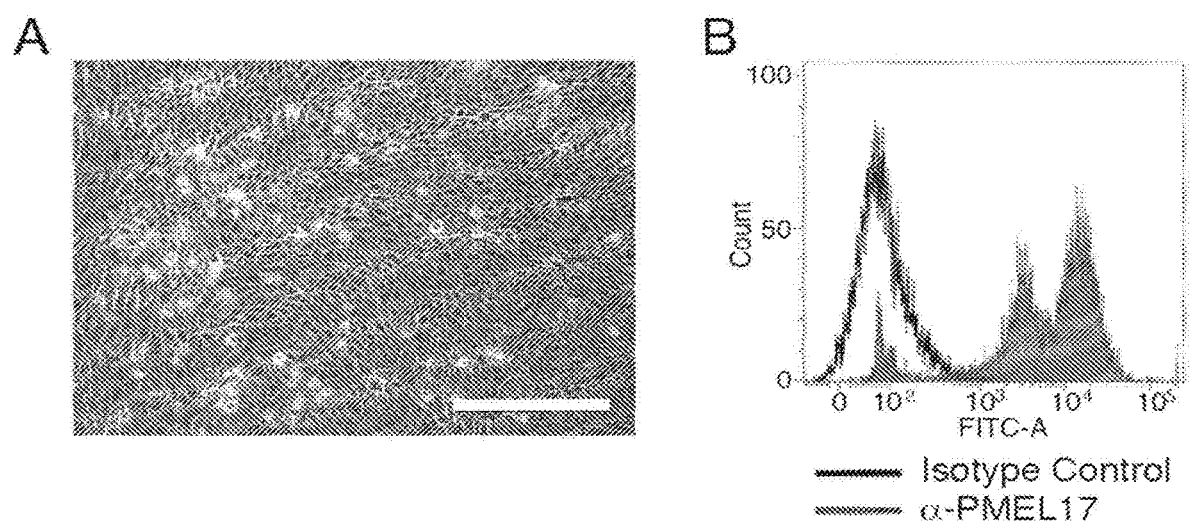
FIG. 24 Rapid and highly efficient generation of hESC-RPECs on Vitronectin XF, under xeno-free and defined culture conditions.

Fast and efficient differentiation of hESCs to RPECs under xeno-free and defined conditions Xeno-free and defined differentiation of hESC to RPECs (FIG. 24).

Figure 25:
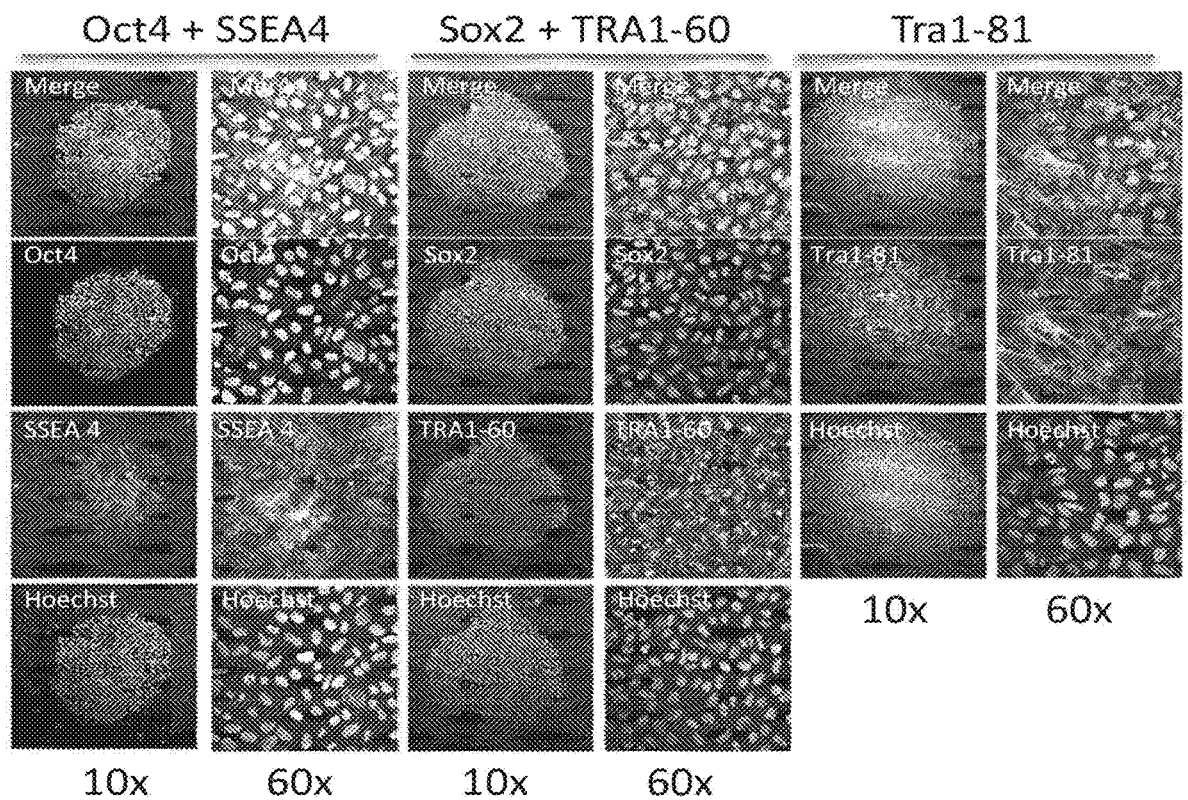
FIG. 25 Immunochemical analysis of undifferentiated human embryonic stem cells cultured under xeno-free and defined culture conditions (on hrLN521 and in mTeSR™2 culture medium) express the pluripotent markers transcription markers Oct4, Sox2, SSEA4, TRA1-60 and TRA1-81.
Figure 26:
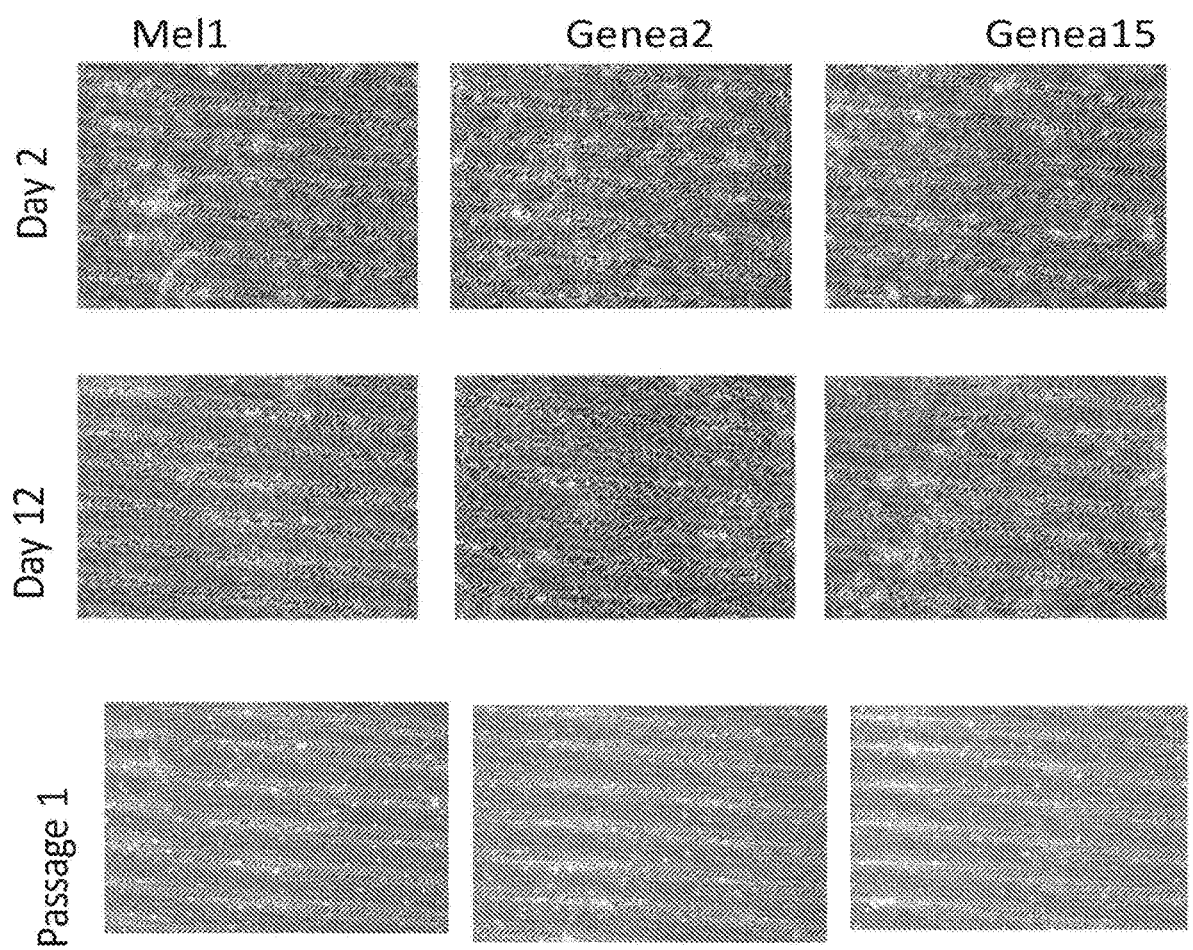
FIG. 26 An example of robust differentiation of three different hESC lines to hESC-RPECs under defined and xeno-free differentiation conditions, during early differentiation towards the eyefield (day 2), appearance of immature hESC-RPEC (shown at day 12), and after the first passage and re-plating on hrLN521 at between approximately 120,000 cells/cm2-150,000 cells/cm2.
Figure 27:
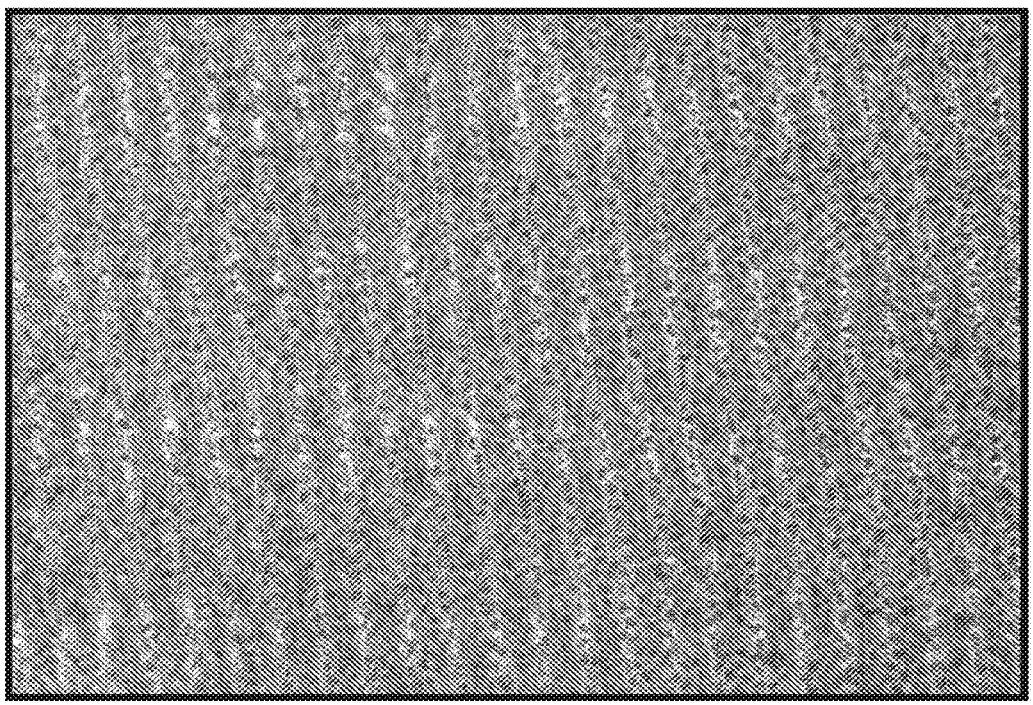
FIG. 27 Morphology of passage 1 (p1) hESC-RPE cells generated under xeno-free and defined differentiation conditions, and passaged onto hrLN521 in xeno-free and defined RPEC Culture Medium.

Characterisation of hESC lines grown under xeno-free and defined conditions demonstrates that ability of hrLN521 to support the pluripotency of hESCs, in the presence of xeno-free, defined culture medium (mTesR™2) (FIG. 25). Early and robust differentiation of hESCs to immature hESC-RPECs, under xeno-free and defined conditions demonstrates uniformity and robustness of the methods (FIG. 26) and quality of cultures (FIG. 27).

Figure 28:
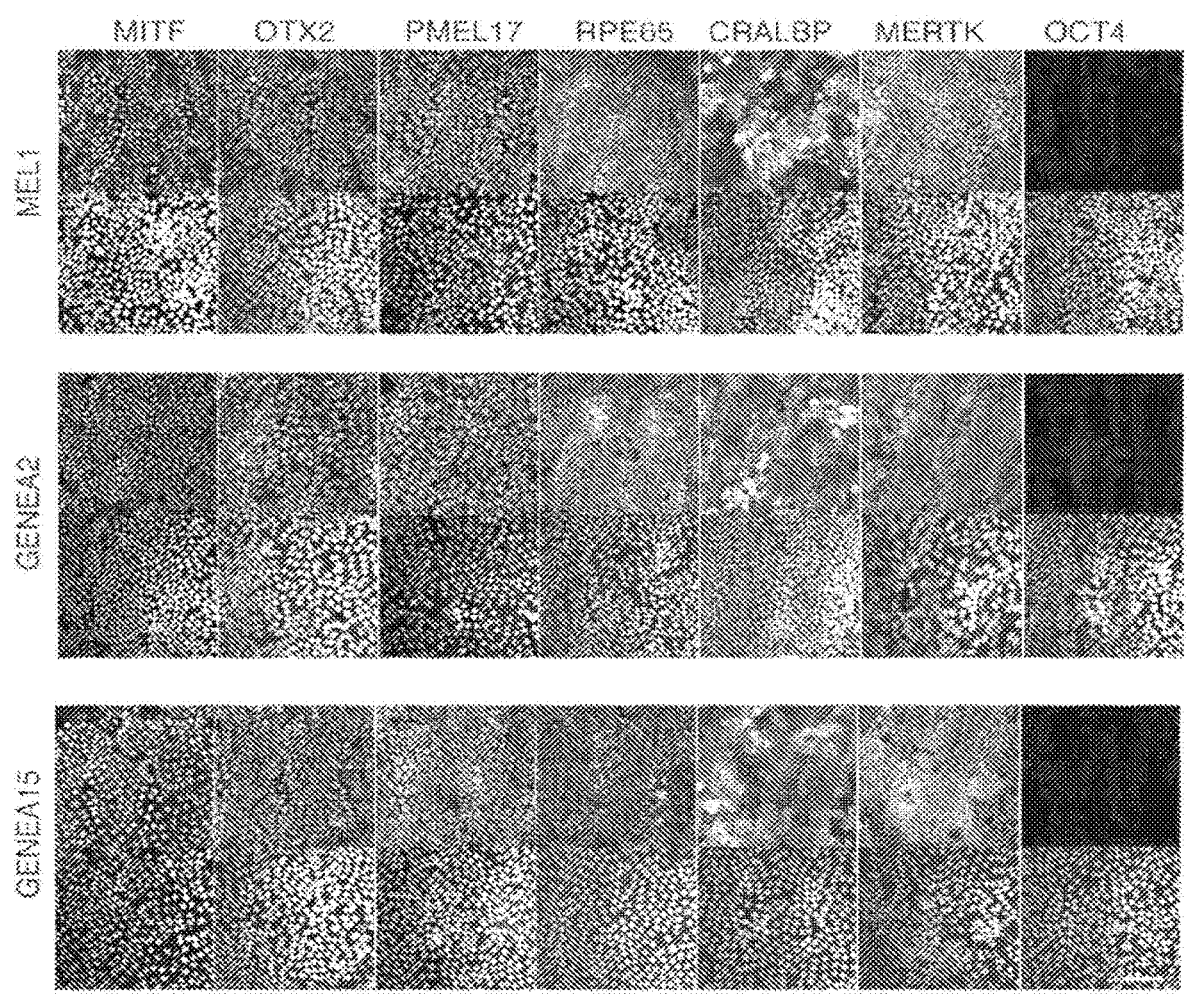
FIG. 28 Immunochemical analyses of hESC-RPE cells derived from Mel1-hESCs, Genea2-hESCs, and Genea15-hESCs, under defined and xeno-free differentiation conditions, after one passage and re-plating on the xeno-free substrate LN521, results in cultures that express key early and mature RPE markers in a highly homogeneous manner, within 30 days of the initiation of differentiation.

Xeno-free and defined differentiation of hESC-RPECs generates highly homogenous cultures that express critical markers of RPE cell identity and function, within one month from the onset of differentiation (FIGS. 28 & 29).

Using an alternative differentiation strategy, hESC-EFPCs cultured in neural retinal induction medium, followed by photoreceptor differentiation medium generate highly pure cultures of photoreceptors that express rhodopsin and recoverin, but not Pmel17. The differentiation method, like that of the RPEC is fast, efficient, xeno-free and defined, and robust and reproducible across stem cell lines (FIG. 30).

What is claimed is:

1. A method for differentiating human pluripotent stem cells (PSCs) to eye field progenitor cells (EFPCs) comprising:
   (a) culturing human PSCs in the form of a high-density monolayer in a primary differentiation medium so as to generate a monolayer of anterior neuroectodermal cells (ANECs);
   (b) disassociating the monolayer of ANECs into essentially single cells;
   (c) forming the single cells into anterior neural ectodermal bodies (ANEBs); and
   (d) culturing the ANEBs in the primary differentiation medium so as to convert the ANECs to EFPCs, and
   (e) differentiating the EFPCs to retinal pigment epithelial cells (RPECs) in a secondary differentiation medium.

2. The method of claim 1, wherein the secondary differentiation medium comprises a small molecule agonist of the Wingless-related integration site (WNT) and Suppressor of Mothers against Decapentaplegic 2 homolog 2 (SMAD2) signaling pathways.

3. The method of claim 2, wherein the small molecule agonist of the WNT signaling pathway is CHIR99021 and the small molecule agonist of the SMAD2 signaling pathway is inducer of definitive endoderm 1 (IDE-1) or inducer of definitive endoderm 2 (IDE-2).

4. The method of claim 2, wherein the primary differentiation medium comprises nicotinamide, and wherein the secondary differentiation medium is free of nicotinamide.

5. The method of claim 2, wherein the method results in at least 80% RPEC cells after 14 days from initiation of primary differentiation.

6. The method of claim 2, further comprising maturing the RPECs in culture by plating the RPEC cells on a xeno-free matrix at a density between 100,000 and 300,000 cells/cm$^2$ in a maturation medium.

7. The method of claim 6, wherein the maturation medium comprises any one or more of CHIR99021, IDE-1, IDE-2, forskolin or rolipram.

8. The method of claim 2, wherein differentiating the EFPCs to RPECs is completed in a timeframe between 2 and 8 days.

9. The method of claim 1, wherein the human PSCs are selected from the group consisting of: primed and naïve human embryonic stem cells (hESCs) and primed and naïve human-induced pluripotent stem cells (hIPSCs).

10. The method of claim 1, wherein the human PSCs are cultured under feeder-free and xeno-free culture conditions.

11. The method of claim 1, wherein prior to step (a) the human PSCs are dissociated to essentially single cells, replated on a substrate and cultured to form the high-density monolayer.

12. The method of claim 11, wherein the human PSCs are replated on the substrate in a range between about 30% and about 90% confluence.

13. The method of claim 1, wherein the primary differentiation medium comprises a bone morphogenic protein (BMP) pathway inhibitor, a transforming growth factor β (TGF-β) inhibitor, a WNT pathway inhibitor, a sonic hedgehog (SHH) pathway activator and nicotinamide.

14. The method of claim 13, wherein the BMP pathway inhibitor is LDN193189, the TGF-β inhibitor is SB431542, the WNT pathway inhibitor is CKI-7 and the SHH pathway activator is purmorphamine.

15. The method of claim 1, wherein step (a) comprises culturing the human PSCs for a period of 2 to 6 days.

16. The method of claim 1, wherein the EFPCs are obtained in a timeframe between 3 and 9 days from initiation of primary differentiation.

17. The method of claim 1, wherein the ANEBs are in the form of 3D cell aggregates which comprise a plurality of ANECs.

18. The method of claim 17, wherein the ANEBs comprise between 200 and 3000 ANECs per ANEB.

19. The method of claim 1, wherein step (d) is performed for at least 12 hrs.

20. The method of claim 1, wherein step (d) comprises culturing the ANEBs in suspension.

* * * * *